(12) United States Patent
Smallheer et al.

(10) Patent No.: US 7,157,470 B2
(45) Date of Patent: *Jan. 2, 2007

(54) SULFONYLAMINOVALEROLACTAMS AND DERIVATIVES THEREOF AS FACTOR XA INHIBITORS

(75) Inventors: Joanne M. Smallheer, Yardley, PA (US); Donald J. Pinto, Kennett Square, PA (US); Shuaige Wang, West Chester, PA (US); Jennifer X. Qiao, Princeton, NJ (US); Wei Han, Yardley, PA (US); Zilun Hu, Thornton, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 627 days.

This patent is subject to a terminal disclaimer.

(21) Appl. No.: 10/429,461

(22) Filed: May 5, 2003

(65) Prior Publication Data

US 2004/0006062 A1    Jan. 8, 2004

Related U.S. Application Data

(60) Provisional application No. 60/378,313, filed on May 6, 2002.

(51) Int. Cl.
| | |
|---|---|
| *A61K 31/45* | (2006.01) |
| *A61K 31/433* | (2006.01) |
| *A61K 31/4196* | (2006.01) |
| *A61K 31/405* | (2006.01) |
| *A61K 31/381* | (2006.01) |
| *C07D 211/76* | (2006.01) |
| *C07D 285/12* | (2006.01) |
| *C07D 249/12* | (2006.01) |
| *C07D 209/04* | (2006.01) |
| *C07D 409/00* | (2006.01) |

(52) U.S. Cl. .............. 514/318; 514/363; 514/384; 514/415; 514/444; 546/193; 548/262.6; 548/136; 548/469; 549/59

(58) Field of Classification Search .............. 549/51, 549/59; 546/194; 514/318, 363, 384, 415, 514/444; 516/193; 518/136, 262.6, 469
See application file for complete search history.

(56) References Cited

U.S. PATENT DOCUMENTS

| | | | |
|---|---|---|---|
| 5,032,602 A | 7/1991 | Fey et al. | |
| 5,998,447 A | 12/1999 | Stilz et al. | |
| 6,710,058 B1 * | 3/2004 | Jacobson et al. | 514/319 |
| 2005/0096309 A1 * | 5/2005 | Han et al. | 514/212.08 |

FOREIGN PATENT DOCUMENTS

| | | |
|---|---|---|
| EP | 0 454 444 | 10/1991 |
| EP | 0 522 606 | 1/1993 |
| EP | 0 908 764 | 4/1999 |
| WO | WO 95/14012 | 5/1995 |
| WO | WO 97/36900 | 10/1997 |
| WO | WO 99/31506 | 6/1999 |
| WO | WO 99/31507 | 6/1999 |
| WO | WO 99/32477 | 7/1999 |
| WO | WO 99/42455 | 8/1999 |
| WO | WO 00/69826 | 11/2000 |
| WO | WO 00/69832 | 11/2000 |
| WO | WO 00/69833 | 11/2000 |
| WO | WO 00/69834 | 11/2000 |
| WO | WO 03/053925 | 7/2003 |

OTHER PUBLICATIONS

McMurry, John "Organic Chemistry—Fourth Edition" Brooks/Cole Publishing Company, 1996, p. 694.*

* cited by examiner

*Primary Examiner*—Kamal A. Saeed
*Assistant Examiner*—Joseph R. Kosack
(74) *Attorney, Agent, or Firm*—Jing G. Sun; David H. Vance

(57) ABSTRACT

The present application describes sulfonylaminovalerolactams and derivatives thereof of Formula I:

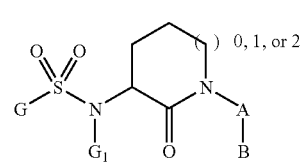

or pharmaceutically acceptable salt forms thereof, wherein ring G is a mono- or bicyclic carbocycle or heterocycle. Compounds of the present invention are useful as inhibitors of trypsin-like serine proteases, specifically factor Xa.

24 Claims, No Drawings

SULFONYLAMINOVALEROLACTAMS AND DERIVATIVES THEREOF AS FACTOR XA INHIBITORS

CROSS REFERENCE TO RELATED APPLICATIONS

This application claims the priority benefits of U.S. Provisional Application No. 60/378,313, filed May 6, 2002, all of which is fully incorporated herein by reference.

FIELD OF THE INVENTION

This invention relates generally to sulfonylaminovalerolactams and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

U.S. Pat. No. 5,032,602 shows 2-pyridones of the following formula.

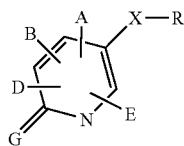

These compounds are inhibitors of HMG-CoA reductase. These compounds are not described as being useful for inhibiting factor Xa and are not considered to be part of the present invention.

WO97/36900 describes inhibitors of farnesyl-protein transferase of the formula.

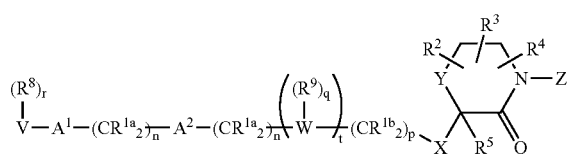

WO97/36900 does not consider inhibition of factor Xa however. The compounds of WO97/36900 are not considered to be part of the present invention.

WO99/31506 and WO99/31507 describe solution phase syntheses of lactams of the formula.

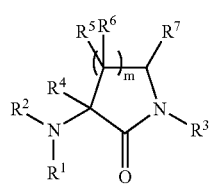

The lactams described in WO99/31506 and WO99/31507 are not considered to be part of the present invention.

WO95/14012 illustrates protease inhibitors of the formula.

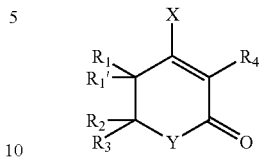

This formula represents pyrones when Y is unsubstituted or substituted nitrogen. However, the compounds of WO95/14012 are not considered to be part of the present invention.

EP 0,908,764 depicts photographic developers of the formula below.

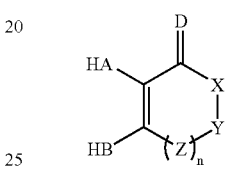

Careful selection of variables can lead one to pyrones. But, the compounds of EP 0,908,764 are not considered to be part of the present invention.

EP 0,454,444 describes glutarimide derivatives of the following formula.

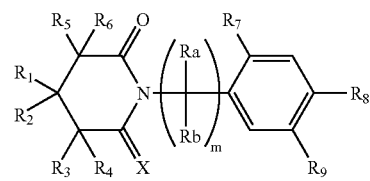

X can be O, $R_1$ can be an alkyl, alkoxy, or halo-substituted benzyl, and $R_9$ can be a cyclic moiety. These compounds are indicated to be herbicides. The compounds of EP 0,454,444 are not considered to be part of the present invention.

WO99/42455 illustrates antiviral agents of the formula.

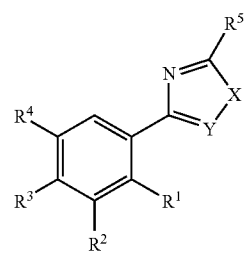

$R^1$ can potentially be a cyclic amide substituted by an aryl amine. The ring containing X and Y is a 5 or 6-membered heteroaromatic ring. The compounds shown in WO99/42455 are not considered to be part of the present invention.

U.S. Pat. No. 5,998,447 shows heterocycles of the following formula.

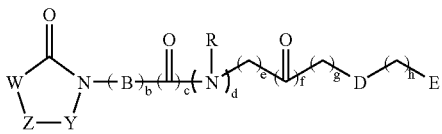

B can be phenylene; W can be substituted phenylalkylene; c, d, e, f, g, and h can all be 0; and, E can be tetrazole. These compounds are inhibitors of leucocyte adhesion and/or antagonists of VLA-4. Tetrazole substituted compounds of this sort are not considered to be part of the present invention.

EP 0,522,606 depicts pyridine derivatives of the following formula.

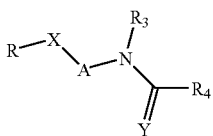

R can be substituted pyridine, X can be O, A is a carbon atom that can be part of a ring (i.e., a 1,1-substituted ring), Y can be O, and $R_3$ and $R_4$ can combine for form a cyclic lactam containing an substituted aralkyl. Compounds of this sort are not considered to be part of the present invention.

WO00/69826, WO00/69832, WO00/69833, and WO00/69834 relate to coagulation cascade inhibitors that are 1,3-disubsituted pyridones of the formula shown below, or aza-substituted derivatives.

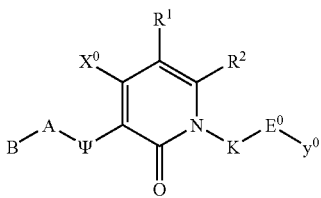

B and $Y^0$ are preferably cyclic moieties. A, $\Psi$, K, and $E^0$ are preferably linkers. Pyridones and aza-pyridones of this sort are not considered to be part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel sulfonylaminovalerolactams and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides novel compounds for use in therapy.

The present invention provides the use of novel compounds for the manufacture of a medicament for the treatment of a thromboembolic disorder.

These and other objects, which will become apparent during the following detailed description, have been achieved by the inventors' discovery that sulfonylaminovalerolactams of Formula I:

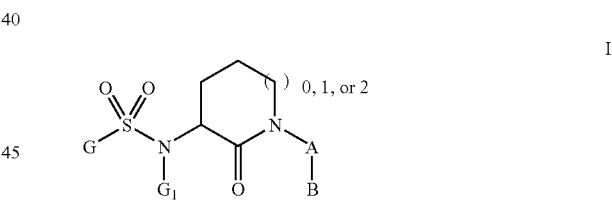

wherein G, $G_1$, A and B are defined below, or pharmaceutically acceptable salt or prodrug forms thereof, are effective factor Xa inhibitors.

DETAILED DESCRIPTION OF PREFERRED EMBODIMENTS

[1] Thus, in an embodiment, the present invention provides a novel compound of formula Ia, Ib, or Ic:

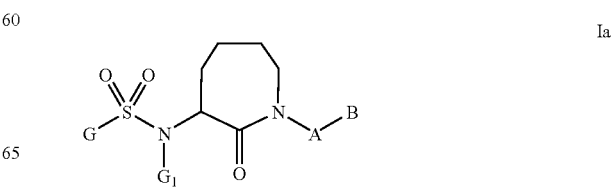

-continued

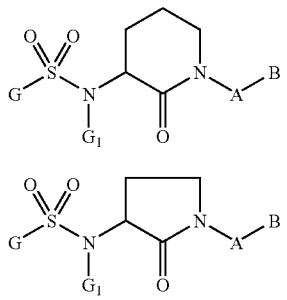

or a stereoisomer or pharmaceutically acceptable salt thereof, wherein;

the central lactam ring is substituted with 0–2 $R^{1a}$;

G is a group of formula IIa or IIb:

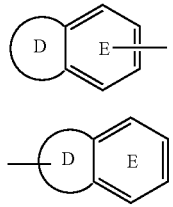

ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent, ring E is selected from phenyl, phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

$G_1$ is selected from H, $(CR^3R^{3a})_{1-2}C(O)R^2$, $(CR^3R^{3a})_{1-2}NR^2R^{2a}$, $(CR^3R^{3a})_{1-2}OR^2$, $(CR^3R^{3a})_{1-2}S(O)_pR^2$, $(CR^3R^{3a})_{1-2}NR^2C(O)R^2$, $(CR^3R^{3a})_{1-2}NR^2C(O)NR^2R^{2a}$, $(CR^3R^{3a})_{1-2}NR^2C(O)OR^2$, $(CR^3R^{3a})_{1-2}S(O)_2NR^2R^{2a}$, $(CR^3R^{3a})_{1-2}NR^2S(O)_2NR^2R^{2a}$, $(CR^3R^{3a})_{1-2}OC(O)R^2$, $(CR^3R^{3a})_{1-2}C(O)OR^2$, $(CR^3R^{3a})_{1-2}C(O)NR^2R^{2a}$, $(CR^3R^{3a})_{1-2}C(O)NR^2(CR^3R^{3a})(CR^3R^{3a})_{1-2}OR^2$, $(CR^3R^{3a})_{1-2}C(O)NR^2(CR^3R^{3a})(CR^3R^{3a})_{1-2}NR^2R^{2a}$, $(CR^3R^{3a})C(O)NR^2(CR^3R^{3a})_{1-2}C(O)NR^2R^{2a}$, $(CR^3R^{3a})C(O)NR^2(CR^3R^{3a})_{1-2}C(O)OR^2$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $(CR^3R^{3a})_{0-4}$—$C_{3-10}$ carbocycle substituted with 0–3 $R^{1a}$, and $(CR^3R^{3a})_{0-4}$-5-12 membered heterocycle consisting of: carbon atoms and 1–4 heteroatoms selected from the group consisting of N, O, and $S(O)_p$ and substituted with 0–3 $R^{1a}$;

A is selected from:
  $C_{3-10}$ carbocycle substituted with 0–2 $R^4$, and
  5–12 membered heterocycle consisting of: carbon atoms and 1–4 heteroatoms selected from the group consisting of N, O, and $S(O)_p$ and substituted with 0–2 $R^4$;

B is selected from $X$—$Y$—$R^{4a}$, $N(B^1)C(O)C(R^3R^{3g})_{1-4}NB^2B^3$, and

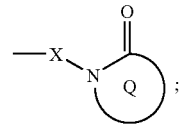

provided that the central lactam ring and B are attached to different atoms on A and that the A-X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

alternatively, $NB^2B^3$ is a 3–8 membered heterocycle consisting of: the shown N, carbon atoms, and 0–3 additional heteroatoms selected from the group consisting of N, O, and $S(O)_p$ and substituted with 0–2 $R^5$;

ring Q is a 4–7 membered lactam consisting of, in addition to the amide group shown, carbon atoms and 0–2 heteroatoms selected from $NR^{4c}$, O, S, S(O), and $S(O)_2$, wherein:
  0–2 double bonds are present within the ring and the ring is substituted with 0–2 $R^{4a}$;

alternatively ring Q is a 4–7 membered lactam to which another ring is fused, wherein:

the lactam consists of, in addition to the shown amide group, carbon atoms and 0–2 heteroatoms selected from $NR^{4c}$, O, S, S(O), and $S(O)_2$ and 0–2 double bonds are present within the ring;

the fusion ring is phenyl or a 5–6 membered heteroaromatic consisting of carbon atoms and 0–2 $NR^{4c}$, O, S, S(O), and $S(O)_2$;

ring Q, which includes the lactam ring and the fusion ring, is substituted with 0–3 $R^{4a}$;

X is absent or is selected from —$(CR^2R^{2a})_{1-4}$—, —$CR^2(CR^2R^{2b})(CH_2)_t$—, —C(O)—, —$C(=NR^{1b})$—, —$CR^2(NR^{1b}R^2)$—, —$CR^2(OR^2)$—, —$CR^2(SR^2)$—, —$C(O)CR^2R^{2a}$—, —$CR^2R^{2a}C(O)$, —S(O)—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$S(O)_2NR^2CR^2R^{2a}$—, —$CR^2R^{2a}S(O)_2NR^2$—, —$NR^2S(O)_2$—, —$CR^2R^{2a}NR^2S(O)_2$—, —$NR^2S(O)_2CR^2R^{2a}$—, —$NR^2C(O)$—, —$C(O)NR^2$—, —$NR^2C(O)CR^2R^{2a}$—, —$C(O)NR^2CR^2R^{2a}$—, —$CR^2R^{2a}NR^2C(O)$—, —$CR^2R^{2a}C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

Y is selected from $CY^1Y^2R^{4a}$, a $C_{3-10}$ carbocycle, and 3–10 membered heterocycle, wherein the carobocycle or heterocycle consists of carbon atoms and 0–4 heteroatoms selected from N, O, and $S(O)_p$, the carbocycle or heterocycle further comprises 0–4 double bonds and 0–2 carbonyl groups, and the carbocycle or heterocycle is substituted with 0–2 $R^4$;

$y^1$ and $y^2$ are independently $C_{1-4}$ alkyl substituted with 0–2 $R^4$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—$C(=NR^{1b})NR^3R^{1b}$, $NR^3(CR^3R^{3a})_r$$R^{1c}$, $O(CR^3R^{3a})_r$$R^{1c}$, $(CR^3R^{3a})_r$$SCR^3R^{3a}R^{1c}$, $(CR^3R^{3a})_r$$NR^3(CR^3R^{3a})_r$$R^{1b}$, $(CR^3R^{3a})_r$$C(O)NR^2(CR^3R^{3a})_r$$R^{1b}$, $CO_2(CR^3R^{3a})_r$$R^{1b}$, $O(CR^3R^{3a})_r$$R^{1b}$, $(CR^3R^{3a})_r$$S(CR^3R^{3a})_r$$R^{1b}$, $S(O)_p$$(CR^3R^{3a})_r$$R^{1d}$, $O(CR^3R^{3a})_r$$R^{1d}$, $NR^3(CR^3R^{3a})_r$$R^{1d}$, $OC(O)NR^3(CR^3R^{3a})_r$$R^{1d}$, $NR^3C(O)NR^3(CR^3R^{3a})_r$$R^{1d}$, $NR^3C(O)O(CR^3R^{3a})_r$$R^{1d}$, and $NR^3C(O)(CR^3R^{3a})_r$$R^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2R^2C(O)NR^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0–2 $R^{4b}$ and 5–10 membered heterocycle consisting of carbon atoms and from 1–4 heteroatoms selected from the group consisting of N, O, and $S(O)_p$ and substituted with 0–2 $R^{4b}$, provided that $R^{1d}$ forms other than an N—S bond;

$R^2$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$, s are attached to the same nitrogen atom, then $R^{2d}$ and $R^{2d}$, together with the nitrogen atom to which they are attached, combine to form a 5–10 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, bx;1$(CR^3R^{3a})_rOR^2$, $(CR^3R^{3a})_rF$, $(CR^3R^{3a})_rCl$, $(CR^3R^{3a})_rBr$, $(CR^3R^{3a})_rI$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, —$(CR^3R^{3g})_r$—$C_{5-10}$ membered carbocycle substituted with 0–3 $R^{4c}$, —$(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_rCN$, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$OC(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2NR^{2d}R^{2d}$, $(CR^3R^{3g})_r$—$C(O)NR^{2d}SO_2R^{2d}$, $(CR^3R^{3g})_r$—$NR^{2d}SO_2R^{2d}$, and $(CR^3R^{3g})_r$—$S(O)_pR^{2d}$, provided that $S(O)_rR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-6}$ alkenyl, $C_{2-6}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR_3R^{3a})_rC(O)NR^2SO_2$—$C_{1-4}$ alkyl, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rCH(=NOR^{3d})$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-$CH_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
r1, at each occurrence, is selected from 1, 2, 3, 4, 5, and 6; and,
t, at each occurrence, is selected from 0, 1, 2, and 3.

[2] In another embodiment, the present invention provides a novel compound, wherein:

the central lactam ring is substituted with 0–1 $R^{1a}$;
G is a group of formula IIa or IIb:

IIa

IIb ring D, including the two atoms of ring E to which it is attached, is a 5–6 membered ring consisting of: carbon atoms and 0–2 heteroatoms selected from the group consisting of N, O, and $S(O)_p$;
ring D is substituted with 0–2 R and there are 0–3 ring double bonds;
E is selected from phenyl, pyridyl, pyrimidyl, pyrazinyl, and pyridazinyl, and is substituted with 1–2 R;
alternatively, ring D is absent, and ring E is selected from phenyl, pyridyl, pyrimidyl, and thienyl, and ring E is substituted with 1–2 R;
alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and has 0–3 ring double bonds;
R is selected from H, $C_{1-4}$ alkyl, F, Cl, OH, $OCH_3$, $OCH_2CH_3$, $OCH(CH_3)_2$, CN, $C(=NH)NH_2$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, and $OCF_3$;
alternatively, when 2 R groups are attached to adjacent atoms, they combine to form methylenedioxy or ethylenedioxy;
$G_1$ is selected from H, $(CR^3R^{3a})C(O)R^2$, $(CR^3R^{3a})NR^2R^{2a}$, $(CR^3R^{3a})OR^2$, $(CR^3R^{3a})S(O)_pR^2$, $(CR^3R^{3a})NR^2C(O)R^2$, $(CR^3R^{3a})NR^2C(O)NR^2R^{2a}$, $(CR^3R^{3a})NR^2C(O)OR^2$, $(CR^3R^{3a})S(O)_2NR^2R^{2a}$, $(CR^3R^{3a})NR^2S(O)_2NR^2R^{2a}$, $(CR^3R^{3a})OC(O)R^2$, $(CR^3R^{3a})C(O)OR^2$, $(CR^3R^{3a})C(O)NR^2R^{2a}$, $(CR^3R^{3a})C(O)NR^2(CR^3R^{3a})(CR^3R^{3a})OR^2$, $(CR^3R^{3a})C(O)NR^2(CR^3R^{3a})(CR^3R^{3a})(CR^3R^{3a})OR^2$, $(CR^3R^{3a})C(O)NR^2(CR^3R^{3a})(CR^3R^{3a})NR^2R^{2a}$, $(CR^3R^{3a})C(O)NR^2(CR^3R^{3a})(CR^3R^{3a})(CR^3R^{3a})NR^2R^{2a}$, $(CR^3R^{3a})C(O)NR^2(CR^3R^{3a})C(O)NR^2R^{2a}$, $(CR^3R^{3a})C(O)NR^2(CR^3R^{3a})(CR^3R^{3a})C(O)NR^2R^{2a}$, $(CR^3R^{3a})C(O)NR^2(CR^3R^{3a})C(O)NR^2(CR^3R^{3a})C(O)OR^2$, $(CR^3R^{3a})C(O)NR^2(CR^3R^{3a})C(O)NR^2(CR^3R^{3a})C(O)OR^2$, $C_{1-6}$ alkyl substituted with 0–1 $R^{1a}$, $C_{2-6}$ alkenyl substituted with 0–1 $R^{1a}$, $C_{2-6}$ alkynyl substituted with 0–1 $R^{1a}$, $(CR^3R^{3a})_{0-4}$—$C_{3-10}$ carbocycle substituted with 0–1 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–1 $R^{1a}$;

A is selected from:
$C_{5-10}$ carbocycle substituted with 0–2 $R^4$, and
5–10 membered heterocycle consisting of: carbon atoms and 1–4 heteroatoms selected from the group consisting of N, O, and $S(O)_p$ and substituted with 0–2 $R^4$;
provided that A is other than a dihydro-benzopyran;
B is selected from $N(B^1)C(O)C(R^3R^{3g})NB^2B^3$, $N(B^1)C(O)C(R^3R^{3g})C(R^3R^{3g})NB^2B^3$, provided that the central lactam ring and B are attached to different atoms on A and that the A-X—N moiety forms other than a N—N—N group;
$B^1$ is selected from H, $CH_3$, $CH_2CH_3$, $CH_2CH2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;
$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;
$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;
ring Q is a 4–7 membered lactam consisting of, in addition to the amide group shown, carbon atoms and 0–2 heteroatoms selected from $NR^{4c}$, O, S, S(O), and $S(O)_2$, wherein:
0–2 double bonds are present within the ring and the ring is substituted with 0–2 $R^{4a}$;
alternatively, ring Q is a 4–7 membered lactam to which another ring is fused, wherein:
the lactam consists of, in addition to the shown amide group, carbon atoms and 0–2 heteroatoms selected from $NR^{4c}$, O, S, S(O), and $S(O)_2$ and 0–1 double bonds are present within the ring;
the fusion ring is phenyl or a 5–6 membered heteroaromatic consisting of carbon atoms and 0–2 $NR^{4c}$, O, and S;
ring Q, which includes the lactam ring and the fusion ring, is substituted with 0–3 $R^{4a}$;

ring $Q^1$ is selected from $CY^1Y^2$, a $C_{3-7}$ monocyclic carbocycle, and a 3–7 membered monocyclic heterocycle, wherein the carbocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

X is absent or is selected from —$(CR^2R^{2a})_{1-4}$—, —C(O)—, —C(O)$CR^2R^{2a}$—, —$CR^2R^{2a}$C(O), —$S(O)_2$—, —$S(O)_2CR^2R^{2a}$—, —$CR^2R^{2a}S(O)_2$—, —$S(O)_2NR^2$—, —$NR^2S(O)_2$—, —$NR^2C(O)$—, —C(O)$NR^2$—, $NR^2$, —$NR^2CR^2R^{2a}$—, —$CR^2R^{2a}NR^2$—, O, —$OCR^2R^{2a}$—, and —$CR^2R^{2a}O$—;

$Y^1$ and $Y^2$ are independently $C_{1-3}$ alkyl substituted with 0–1 $R^4$;

$R^{1a}$, at each occurrence, is selected from H, —$(CR^3R^{3a})_r$—$R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—C(=$NR^{1b}$)$NR^3R^{1b}$, $NR^3(CR^3R^{3a})_rR^{1c}$, $O(CR^3R^{3a})_rR^{1c}$, $(CR^3R^{3a})_rSCR^3R^{3a}R^{1c}$, $(CR^3R^{3a})_rNR^3(CR^3R^{3a})_rR^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $(CR^3R^{3a})_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, a $C_{5-6}$ carbocyclic-$CH_2$ group substituted with 0–2 $R^{4b}$, a 5–6 membered heterocycle consisting of: carbon atoms and 1–4 heteroatoms selected from the group consisting of N, O, and $S(O)_p$ and substituted with 0–2 $R^{4b}$, and a 5–6 membered heterocycle-$CH_2$ group consisting of: carbon atoms and 1–4 heteroatoms selected from the group consisting of N, O, and $S(O)_p$ and substituted with 0–2 $R^{4b}$ $R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^5$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2R^{2a}$, $S(O)_pR^{5a}$, $NR^2SO_2$—$C_{1-4}$ alkyl, $NR^2SO_2R^5$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-3}$ alkenyl, $C_{2-3}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$ 5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^{5a}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—$C(O)$ bond;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

[3] In another embodiment, the present invention provides a novel compound, wherein the compound is of formula Ib or Ic:

G is selected from the group:

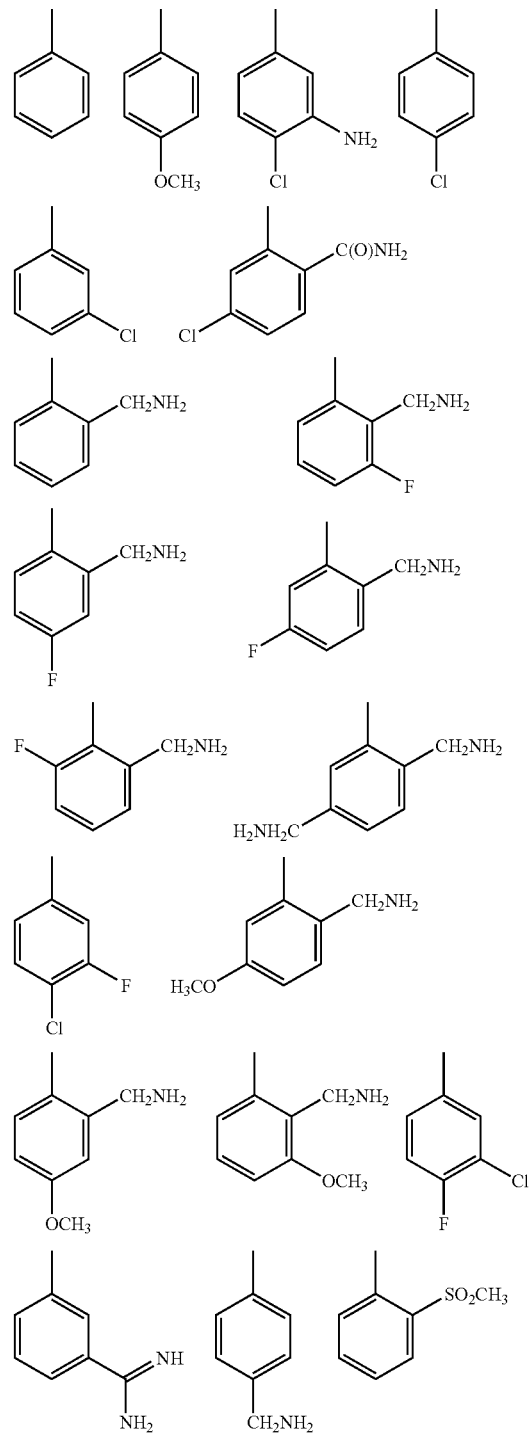

-continued
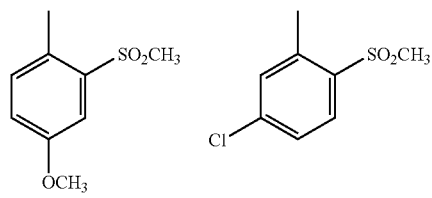
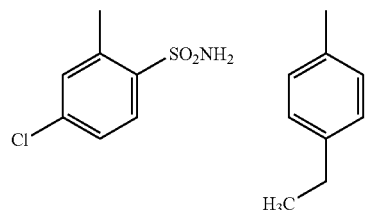
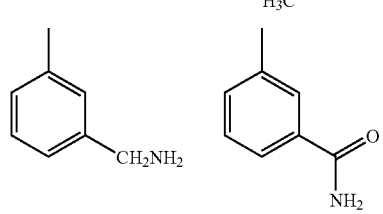
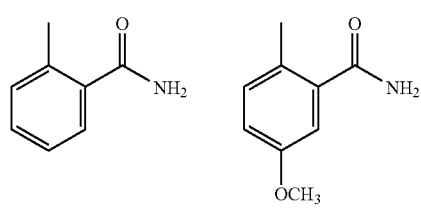
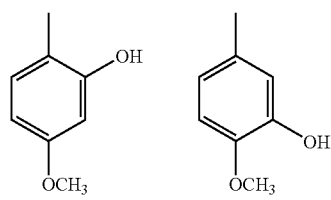
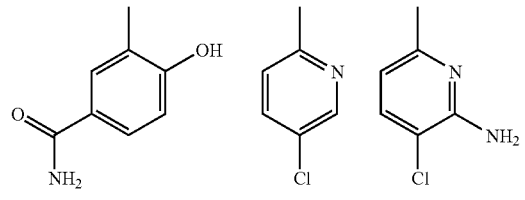
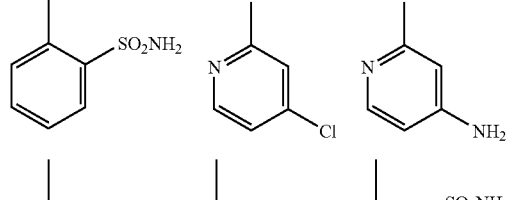
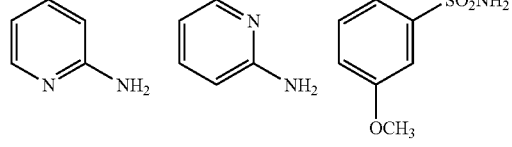
-continued
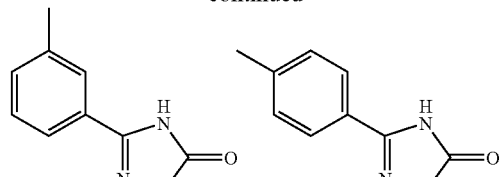
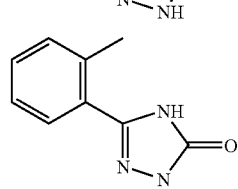
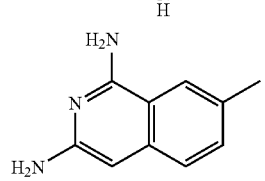
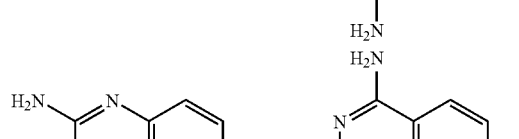
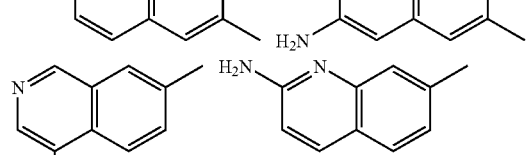
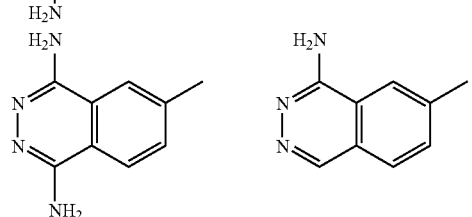
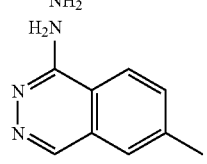
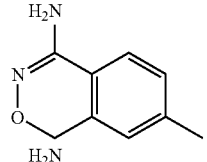
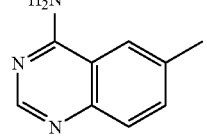
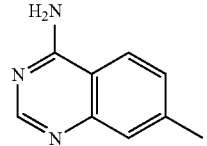
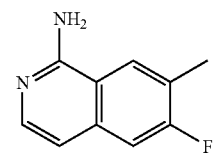

-continued
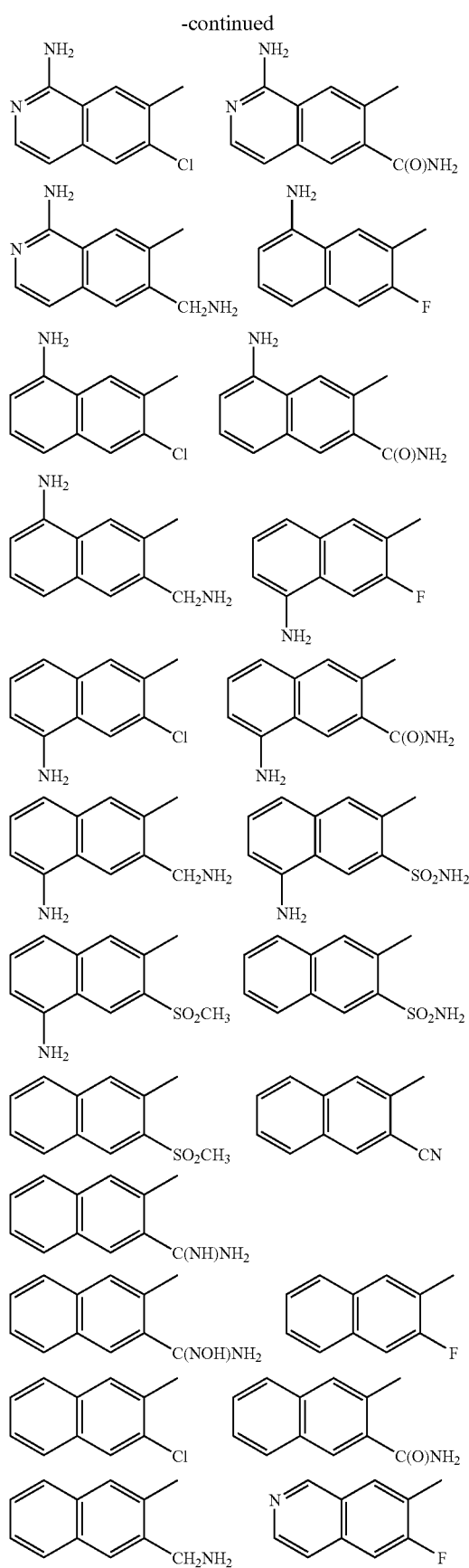
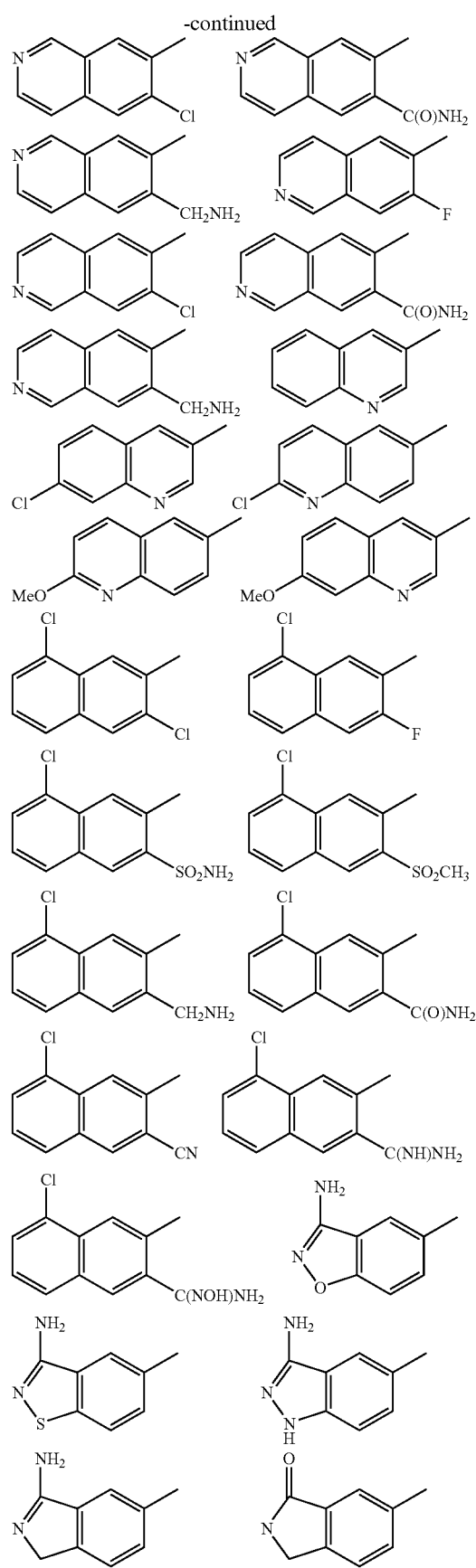

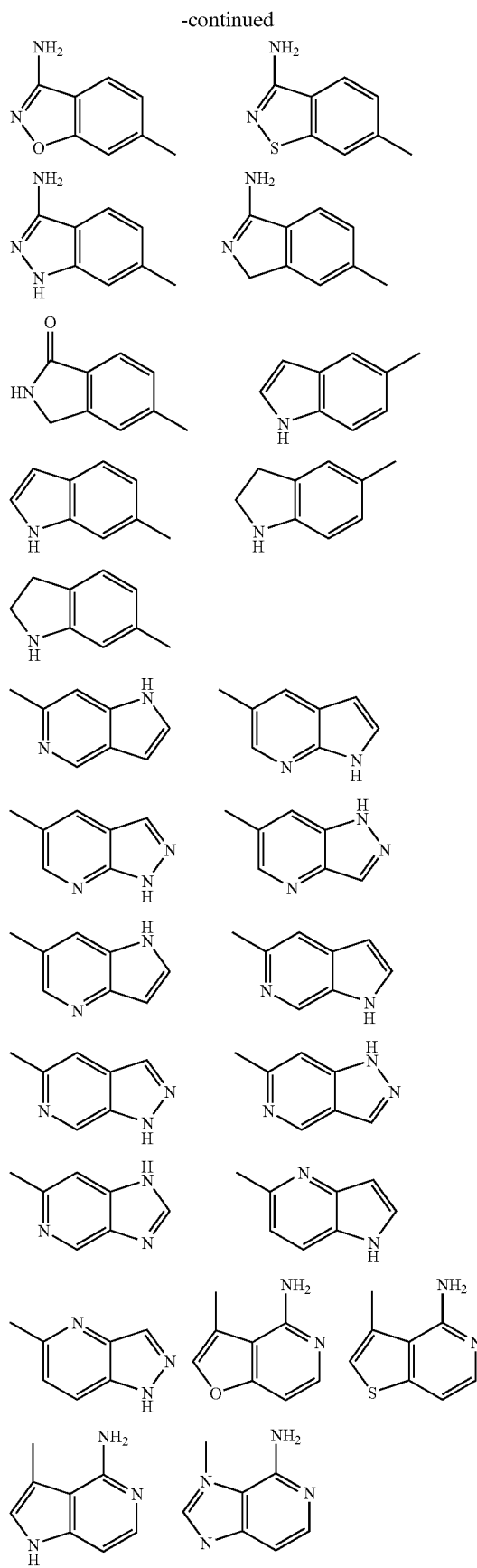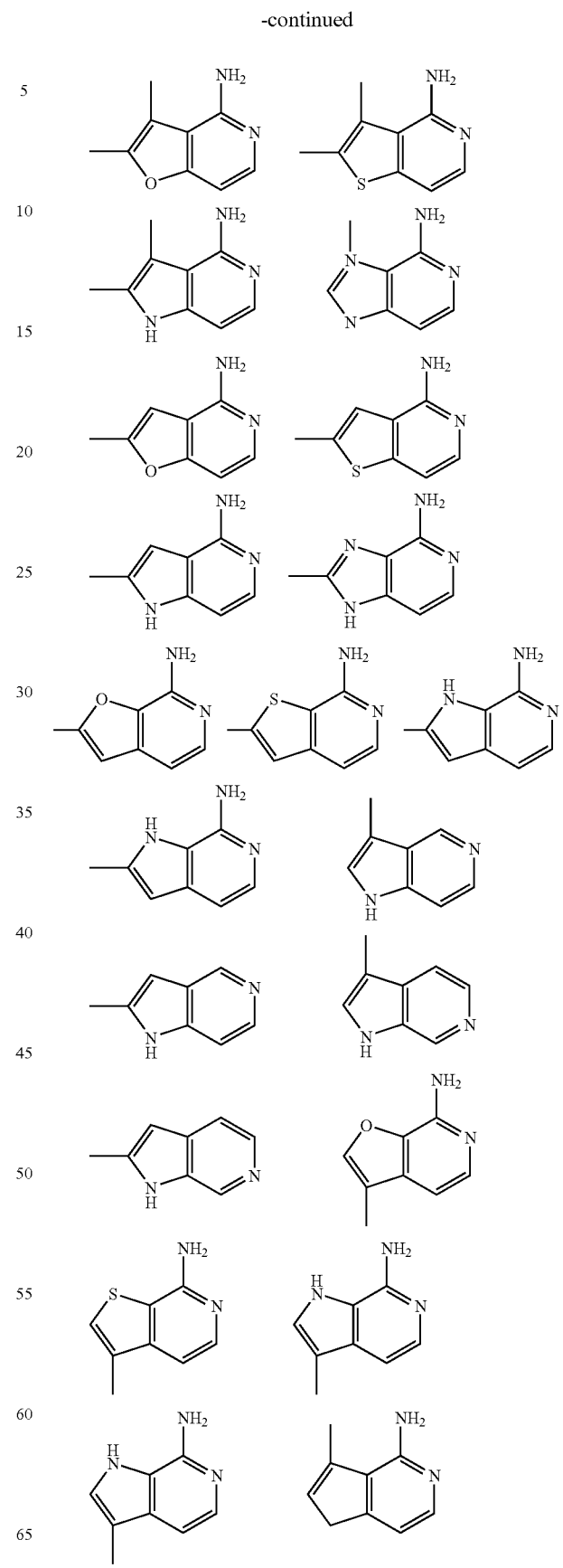

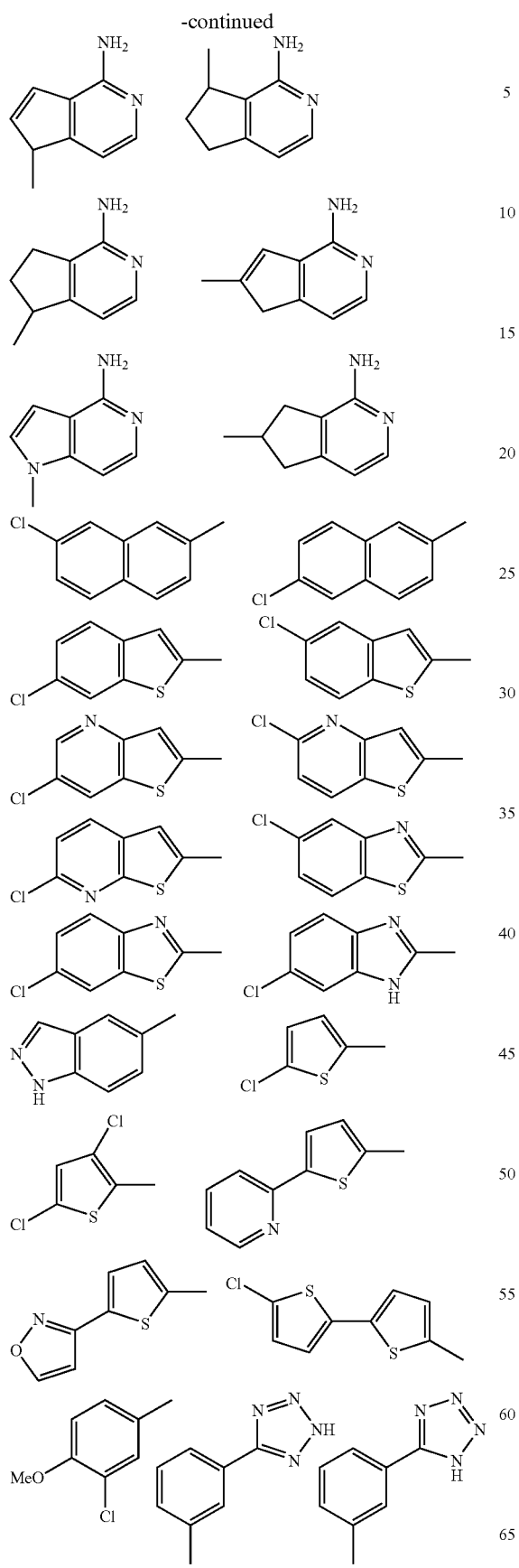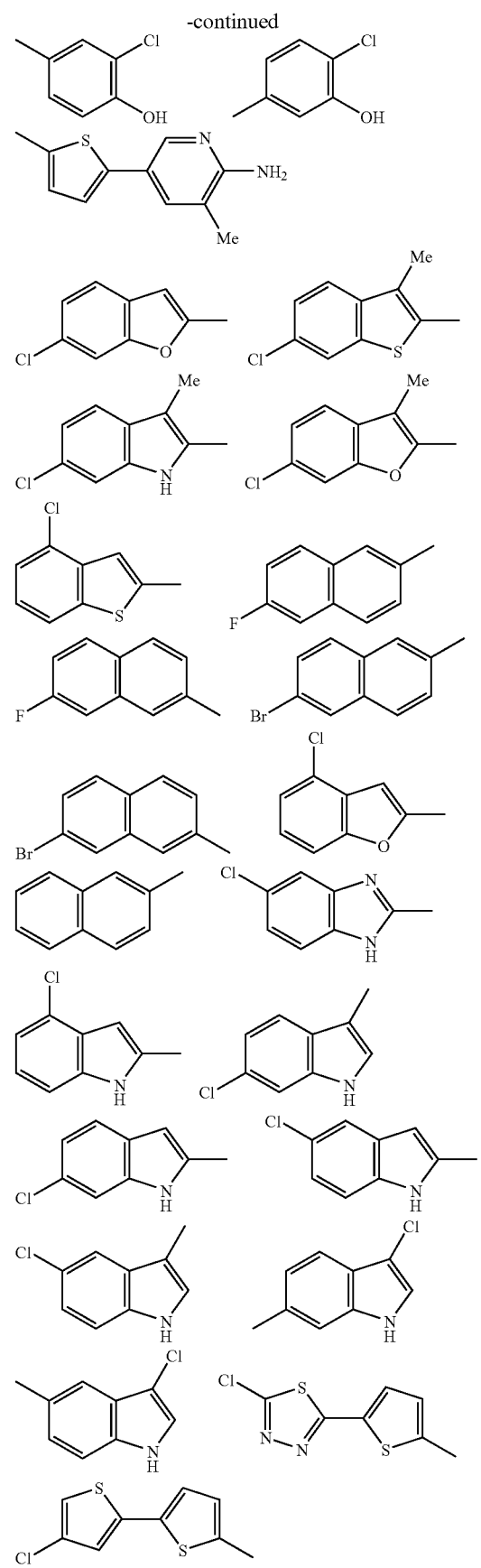

-continued

[chemical structures]

G₁ is selected from H, C₁₋₆ alkyl substituted with 0–1 R¹ᵃ, CH₂C(O)OR², CH₂C(O)NR²R²ᵃ, CH₂C(O)NR²CH₂CH₂OR², CH₂C(O)NR²CH₂CH₂NR²R²ᵃ, CH₂C(O)NR²CH₂C(O)NR²R²ᵃ, CH₂C(O)NR²CH₂CH₂C(O)NR²R²ᵃ, CH₂C(O)NR²CH₂C(O)OR², and CH₂C(O)NR²CH₂CH₂C(O)OR²;

A is selected from one of the following carbocyclic and heterocyclic groups which are substituted with 0–2 R⁴;
  cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B¹ is selected from H, CH₃, CH₂CH₃, CH₂CH₂CH₃, CH(CH₃)₂, —(CH₂)₀₋₁—C₅₋₆ carbocycle substituted with 0–2 R⁴ᵇ, and —(CH₂)₀₋₁-5–6 membered heterocycle consisting of: carbon atoms and 1–4 heteroatoms selected from the group consisting of N, O, and S(O)ₚ and substituted with 0–2 R⁴ᵇ;

B² is selected from H, CH₃, CH₂CH₃, CH₂CH₂CH₃, CH(CH₃)₂, C(O)R²ᵉ, C(O)NR²ᵈR²ᵈ, SO₂NR²ᵈR²ᵈ, and S(O)ₚR⁵ᵃ;

B³ is selected from H, C₁₋₆ alkyl substituted with 0–1 R⁴ᶜ, —(CH₂)₀₋₁-3–6 membered carbocycle substituted with 0–1 R⁵, and a —(CH₂)₀₋₁-5–6 membered heterocycle consisting of: carbon atoms and 1–4 heteroatoms selected from the group consisting of N, O, and S(O)ₚ and substituted with 0–1 R⁵;

ring Q is a 5–7 membered lactam consisting of, in addition to the amide group shown, carbon atoms and 0–2 heteroatoms selected from NR⁴ᶜ, O, S, S(O), and S(O)₂, wherein:
  0–2 double bonds are present within the ring and the ring is substituted with 0–2 R⁴ᵃ;

alternatively, ring Q is a 5–7 membered lactam to which another ring is fused, wherein:
  the lactam consists of, in addition to the shown amide group, carbon atoms and 0–2 heteroatoms selected from NR⁴ᶜ, O, S, S(O), and S(O)₂ and 0–1 double bonds are present within the ring;
  the fusion ring is phenyl or a 5–6 membered heteroaromatic consisting of carbon atoms and 0–2 NR⁴ᶜ, O, and S;
  ring Q, which includes the lactam ring and the fusion ring, is substituted with 0–3 R⁴ᵃ;

ring Q¹ is selected from CY¹Y², a C₃₋₆ monocyclic carbocycle, and 5–6 membered monocyclic heterocycle, wherein the carobocycle or heterocycle consists of carbon atoms and 0–2 heteroatoms selected from N, O, and S(O)p, the carbocycle or heterocycle further comprises 0–1 double bonds and 0–1 carbonyl groups, and the carbocycle or heterocycle is substituted with 0–2 R⁴;

X is absent or is selected from —(CR²R²ᵃ)₁₋₂—, —C(O)—, —S(O)₂—, —S(O)₂NR²—, —NR²S(O)₂—, —NR²C(O)—, —C(O)NR²—, NR², —NR²CR²R²ᵃ—, —CR²R²ᵃNR²—, O, —OCR²R²ᵃ—, and —CR²R²ᵃO—;

Y¹ and Y² are independently C₁₋₂ alkyl substituted with 0–1 R⁴;

R¹ᵃ, at each occurrence, is selected from H, —(CH₂)ᵣ—R¹ᵇ, —(CH₂)ᵣ—O—(CH₂)ᵣ—R¹ᵇ, —(CH₂)ᵣ—C(=NR¹ᵇ)NR³R¹ᵇ, NR³(CR³R³ᵃ)ᵣR¹ᶜ, O(CR³R³ᵃ)ᵣR¹ᶜ, (CH₂)ᵣNR³(CH₂)ᵣR¹ᵇ, (CH₂)ᵣC(O)NR²(CH₂)ᵣR¹ᵇ, CO₂(CH₂)ᵣR¹ᵇ, O(CH₂)ᵣR¹ᵇ, S(O)ₚ(CH₂)ᵣR¹ᵈ, O(CH₂)ᵣR¹ᵈ, NR³(CH₂)ᵣR¹ᵈ, OC(O)NR³(CH₂)ᵣR¹ᵈ, NR³C(O)NR³(CH₂)ᵣR¹ᵈ, NR³C(O)O(CH₂)ᵣR¹ᵈ, and NR³C(O)(CH₂)ᵣR¹ᵈ, provided that R¹ᵃ forms other than an N-halo, N—S, O—O, or N—CN bond;

alternatively, when two R¹ᵃ groups are attached to the same carbon atom, together with the carbon atom to which they are attached they form a 3–6 membered carbocyclic or heterocyclic ring consisting of: carbon atoms and 0–4 heteroatoms selected from the group consisting of N, O, and S(O)ₚ, this ring being substituted with 0–2 R⁴ and 0–3 ring double bonds;

R¹ᵇ is selected from H, CH₃, CH₂CH₃, F, Cl, Br, —CN, —CHO, CF₃, (CH₂)ᵣOR², NR²R²ᵃ, C(O)R²ᵇ, CO₂R²ᵇ, OC(O)R², CO₂R²ᵃ, S(O)ₚR², NR²(CH₂)ᵣOR², NR²C(O)R²ᵇ, NR²C(O)NR²R²ᵃ, C(O)NR²R²ᵃ, SO₂NR²R²ᵃ, NR²SO₂NR²R²ᵃ, NR²SO₂R², C(O)NR²SO₂R², SO₂NR²C(O)R², C₃₋₁₀ carbocycle substituted with 0–2 R⁴, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–2 $R^{4b}$, a benzyl substituted with 0–2 $R^{4b}$, a 5–6 membered heterocycle-$CH_2$ group wherein said heterocycle consists of: carbon atoms and 1–4 heteroatoms selected from the group consisting of N, O, and $S(O)_p$ and substituted with 0–2 $R^{4b}$, and a 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, benzyl, phenyl substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(→O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2R^{2d}$, and $(CR^3R^{3g})_r$—$S(O)_pR^{2d}$, provided that $S(O)^pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{2-3}$ alkenyl, $C_{2-3}$ alkynyl, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(→O)R^2R^{2a}$, $(CR^3R^{3a})N(→O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[4] In another embodiment, the present invention provides a novel compound, wherein:

G is selected from the group:

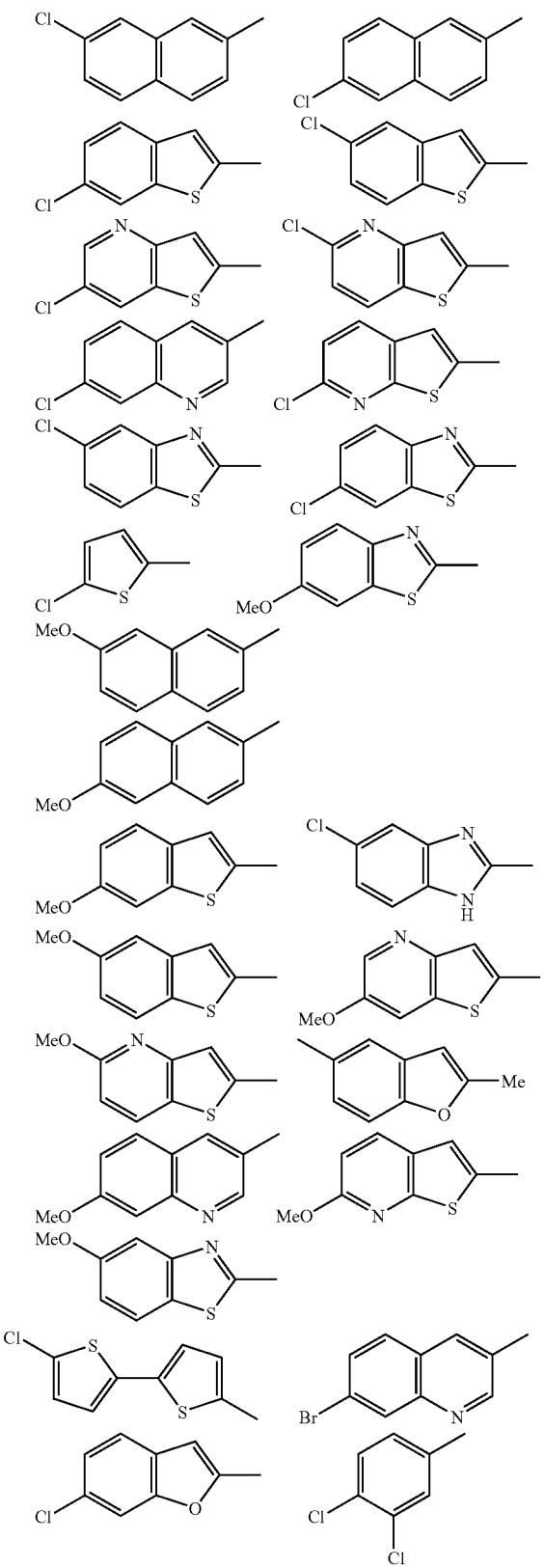

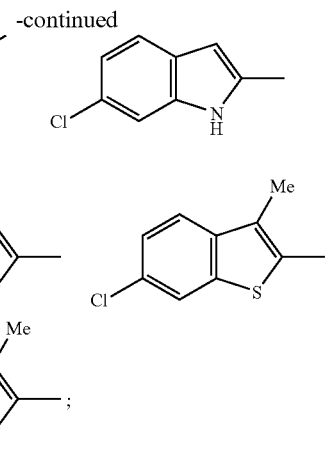

$G_1$ is selected from H, $C_{1-4}$ alkyl substituted with 0–1 $R^{1a}$, $CH_2C(O)OR^2$, $CH_2C(O)NR^2R^{2a}$, $CH_2C(O)NHCH_2CH_2OR^2$, and $CH_2C(O)NHCH_2CH_2NR^2R^{2a}$, $CH_2C(O)OR^2$, $CH_2C(O)NR^2R^{2a}$, $CH_2C(O)N(CH_3)CH_2CH_2OR^2$, $CH_2C(O)N(CH_3)CH_2CH_2NR^2R^{2a}$, $CH_2C(O)NR^2CH_2C(O)NR^2R^{2a}$, $CH_2C(O)NR^2CH_2CH_2C(O)NR^2R^{2a}$, $CH_2C(O)NR^2CH_2C(O)OR^2$, and $CH_2C(O)NR^2CH_2CH_2C(O)OR^2$;

A is selected from one of the following carbocyclic and heterocyclic groups which are substituted with 0–2 $R^4$; cyclohexyl, phenyl, piperidinyl, piperazinyl, pyridyl, pyrimidyl, thienyl, pyrrolyl, pyrrolidinyl, oxazolyl, isoxazolyl, thiazolyl, isothiazolyl, pyrazolyl, and imidazolyl;

B is selected from $N(B^1)C(O)C(R^3R^{3g})NB^2B^3$,

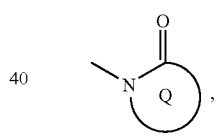

and

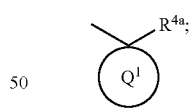

provided that the central lactam ring and B are attached to different atoms on A;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

ring Q is a 6–7 membered lactam consisting of, in addition to the amide group shown, carbon atoms and 0–1 heteroatoms selected from $NR^{4c}$, O, S, S(O), and $S(O)_2$, wherein:
  0–2 double bonds are present within the ring and the ring is substituted with 0–2 $R^{4a}$;
alternatively, ring Q is a 5–7 membered lactam to which another ring is fused, wherein:
  the lactam consists of, in addition to the shown amide group, carbon atoms and 0–1 heteroatoms selected from $NR^{4c}$, O, S, S(O), and $S(O)_2$ and 0–1 double bonds are present within the ring;
  the fusion ring is phenyl;
  ring Q, which includes the lactam ring and the fusion ring, is substituted with 0–2$R^{4a}$;
ring $Q^1$ is selected from $C(CH_3)_2$, $C(CH_2CH_3)_2$, cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and, when Y is a ring, Y is substituted with 0–1 $R^4$;
$R^{1a}$ is selected from H, $R^{1b}$, $C(CH_3)_2R^{1b}$, $CH(CH_3)R^{1b}$, $CH_2R^{1b}$, $CH_2CH_2R^{1b}$, $CH_2OCH_2CH_2R^{1b}$, $OCH_2CH_2R^{1b}$, $(CH_2)_rNR^3CH_2CH_2R^{1b}$, $NR^3(CR^3R^{3a})_tR^{1c}$, $O(CR^3R^{3a})_tR^{1c}$, $(CH_2)_rC(O)NR^2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;
alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–2 ring double bonds;
$R^{1b}$ is selected from H, $CH_3$, $CH_2CH_3$, F, Cl, Br, —CN, —CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-6}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;
$R^{2a}$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, and benzyl;
alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;
$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;
$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;
$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;
$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;
$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;
$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$C(O)NR^{2d}R^{2d}$, $(CR^3R^3g)_r$—$NR^{2d}C(O)R^{2e}$, $(CR^3R^{3g})_r$—$C(O)R^{2e}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;
$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;
$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

R[5], at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 R[6], naphthyl substituted with 0–2 R[6], and benzyl substituted with 0–2 R[6]; and, R[6], at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[5] In another embodiment, the present invention provides a novel, wherein:

G is selected from:

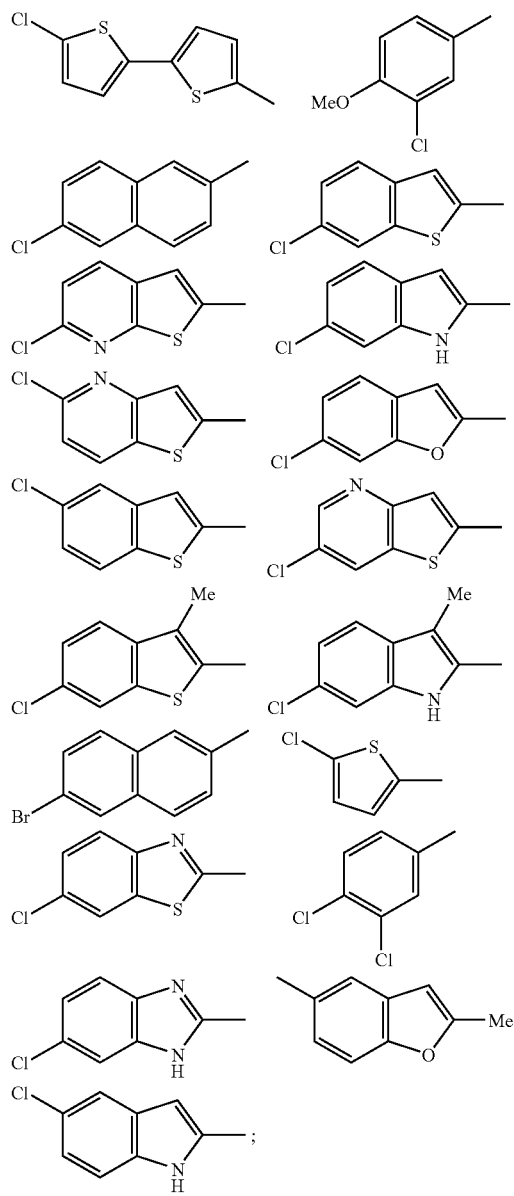

A is selected from one of the following carbocyclic and heterocyclic groups which are substituted with 0–2 R[4]:
cyclohexyl, phenyl, pyridyl, and pyrimidyl;

B is selected from the group:

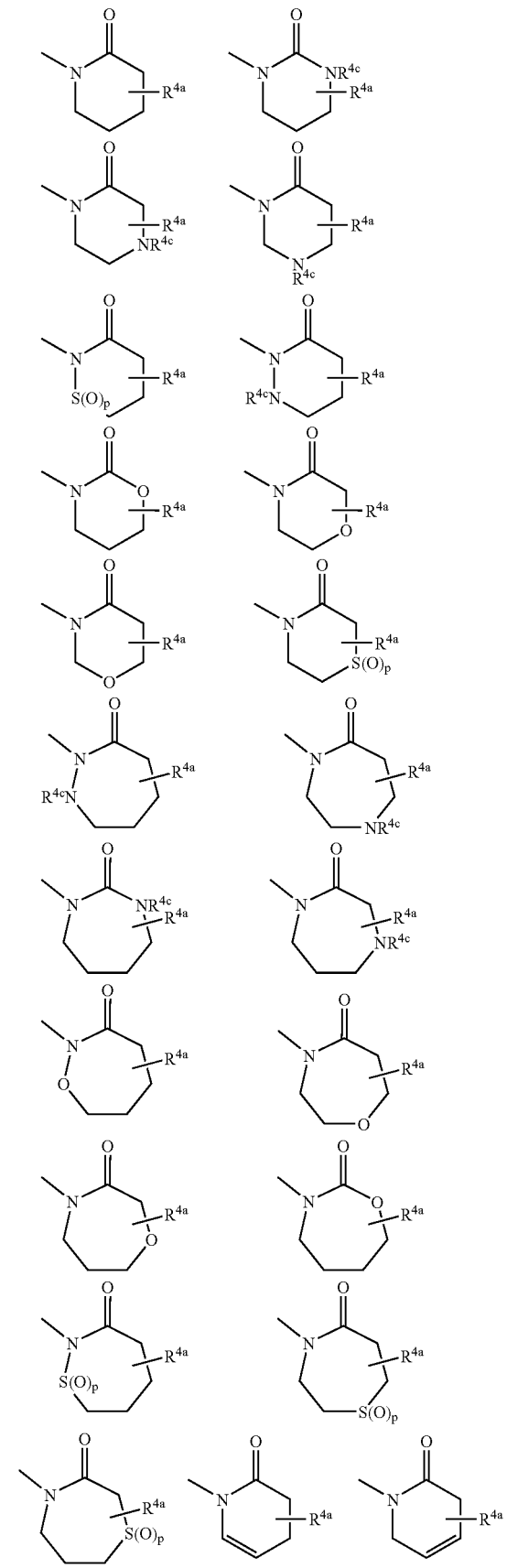

-continued

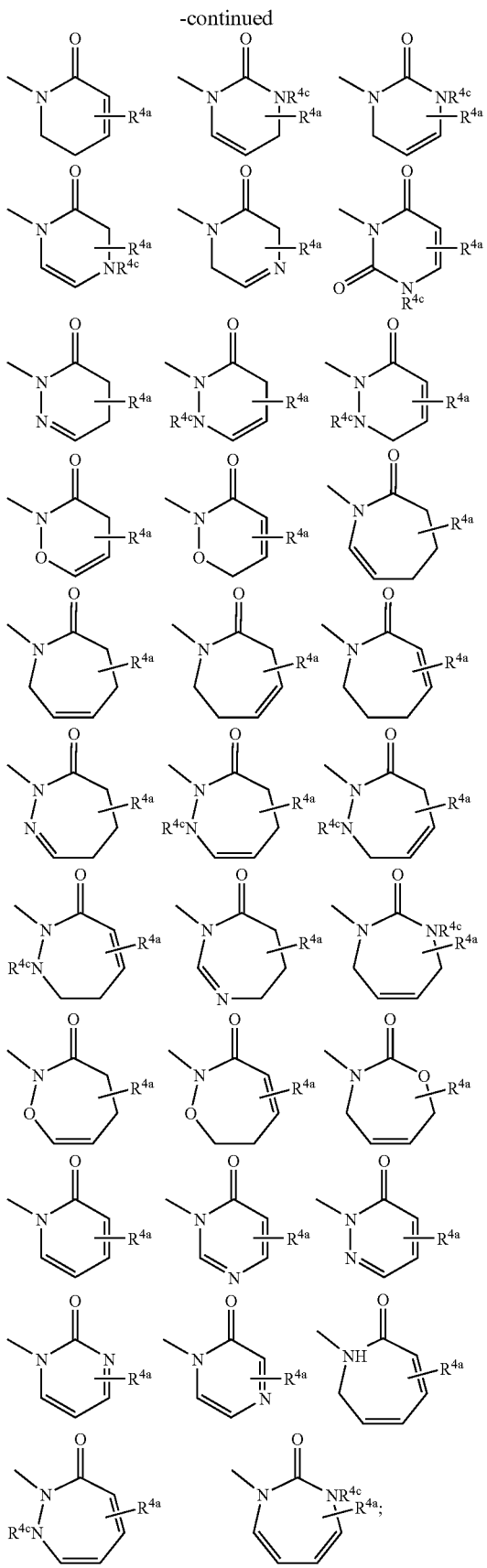

alternatively, B is selected from $N(B^1)C(O)C(R^3R^{3g})NB^2B^3$ and

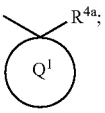

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, and $CH_2$-cyclopropyl;

ring $Q^1$ is selected from $C(CH_3)_2$, $C(CH_2CH_3)_2$, cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

$R^{1a}$ is selected from H, $CH_3$, $CH_2CH_3$, $CH_2CH_2CH_3$, $CH_2(CH_3)_2$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $NHCOCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, $NHSO_2NHCH_3$, $NHSO_2N(CH_3)_2$, $NHCO_2R^{2a}$, $NHC(O)NHR^{2a}$, $CH_2OCH_2CH_2NR^2R^{2a}$, $C(O)NR^2R^{2a}$, $CH_2CH_2OR^2$, $CH_2C(O)NR^2CH_2CH_2OR^2$, $C(O)NHCH_2CH_2NR^2R^{2a}$, $CH_2C(O)NHCH_2CH_2NR^2R^{2a}$, $C(O)NCH_3CH_2CH_2NR^2R^{2a}$, $CH_2C(O)NCH_3CH_2CH_2NR^2R^{2a}$, $CH_2NHCH_2CH_2NR^2R^{2a}$, $CH_2N(CH_3)CH_2CH_2NR^2R^{2a}$, phenyl substituted with 0–2 $R^{4b}$, —$CH_2$-phenyl substituted with 0–2 $R^{4b}$, 5–10 membered aromatic heterocycle consisting of carbon atoms and from 1–4 heteroatoms selected from the group consisting of N, O, and $S(O)_p$ and substituted with 0–2 $R^{4b}$, and —$CH_2$-5–10 membered aromatic heterocycle consisting of carbon atoms and from 1–4 heteroatoms selected from the group consisting of N, O, and $S(O)_p$ and substituted with 0–2 $R^{4b}$, provided that $R^{1a}$ forms other than an N-halo, N—S, O—O, or N—CN bond;

$R^2$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–1 $R^{4b}$, benzyl substituted with 0–1 $R^{4b}$, 5 membered aromatic heterocycle-$CH_2$ group wherein the heterocycle consists of: carbon atoms and 1–4 heteroatoms selected from the group consisting of N, O, and $S(O)_p$ and substituted with 0–1 $R^{4b}$ and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$, $CH_2CH_2OH$, $CH_2CH_2CH_2OH$, $CH_2CH_2NMe_2$, and $CH_2CH_2CH_2NMe_2$, alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $N(\rightarrow O)$ $R^{2d}R^{2d}$, $CH_2N(\rightarrow O)R^{2d}R^{2d}$, $CH_2OR^{2d}$, $C(O)R^{2e}$, $C(O)$ $NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —($CH_2$)-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or S(O)H; and, $R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^3c$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$; and, $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

[6] In another embodiment, the present invention provides a novel compound, wherein the compound is selected from:

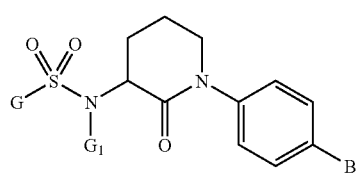

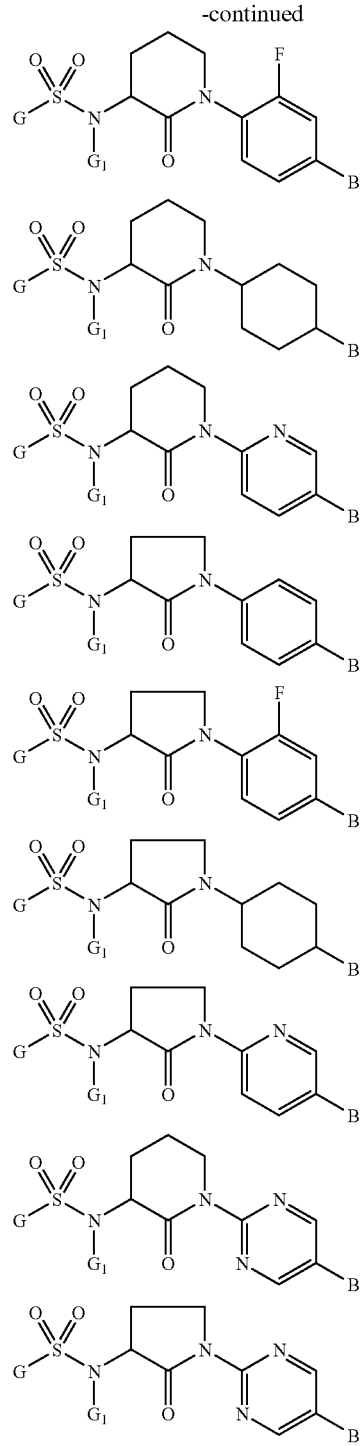

B is selected from:

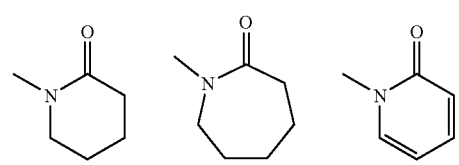

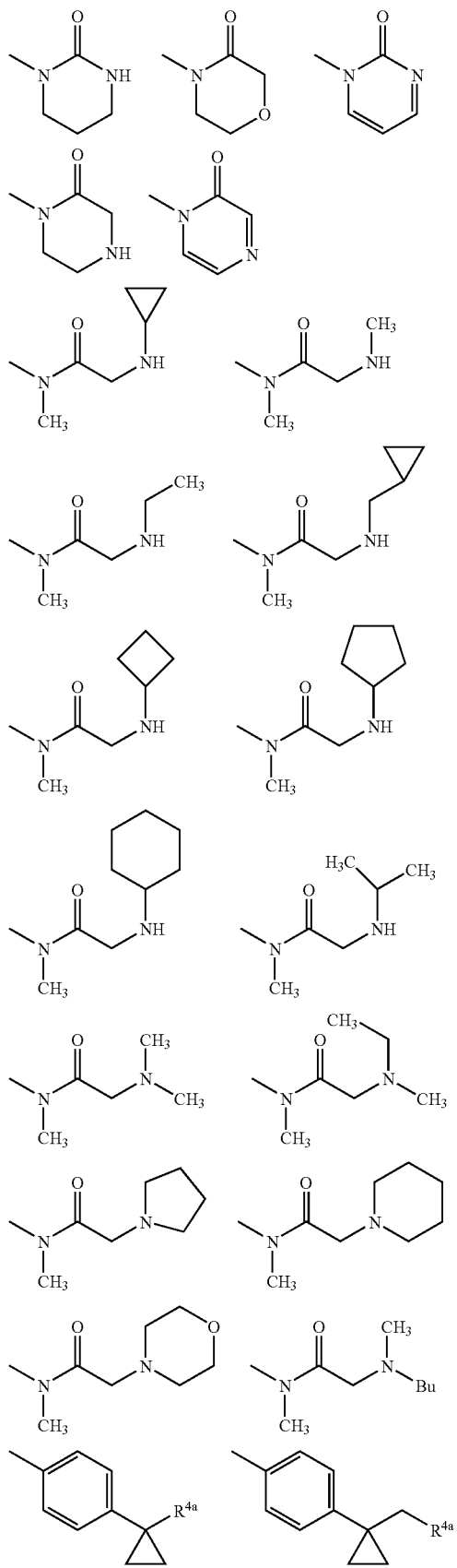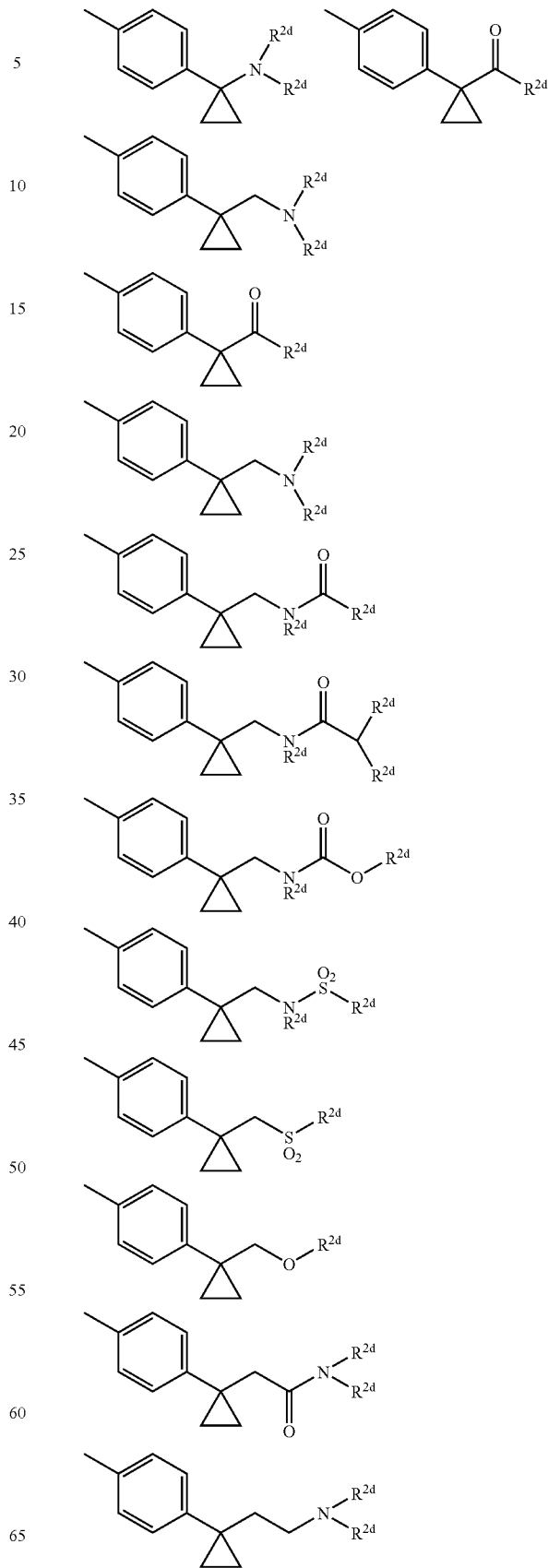

-continued
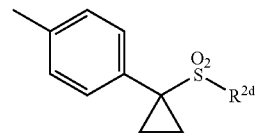
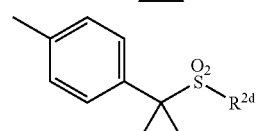
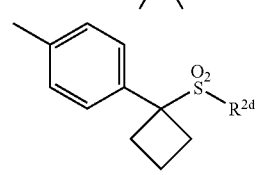
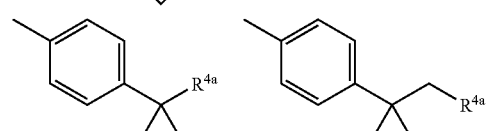
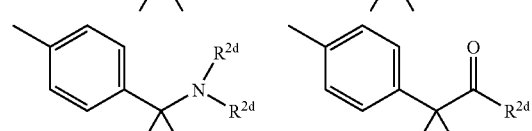
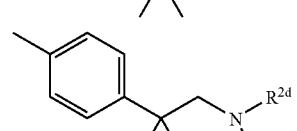
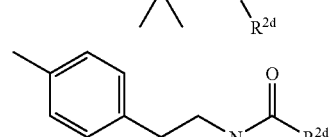
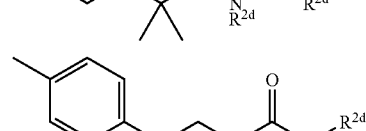
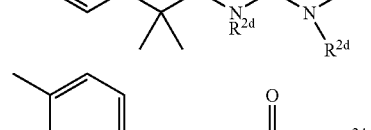
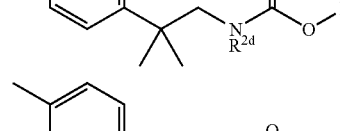
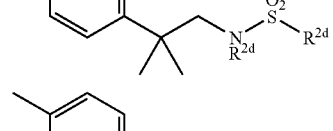
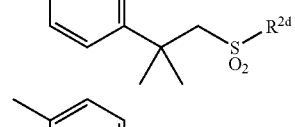
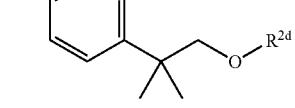
-continued
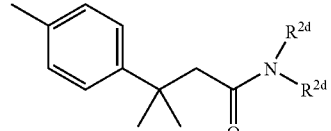
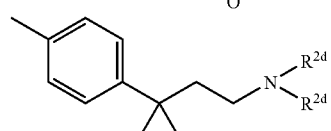
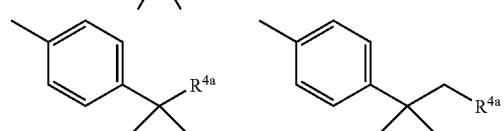
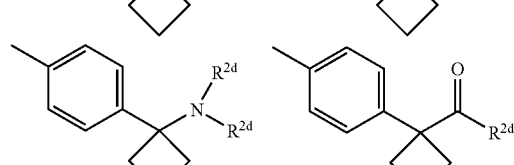
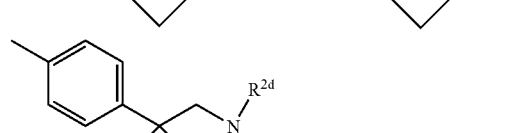
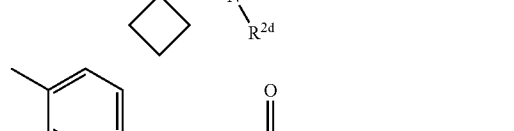
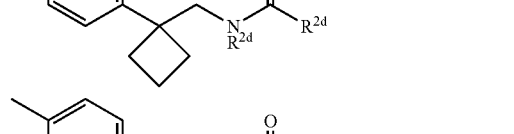
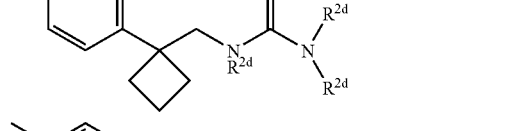
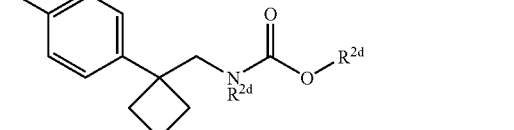
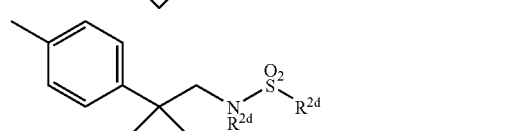
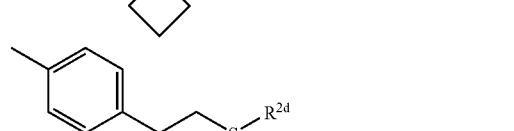
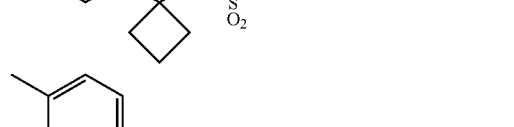

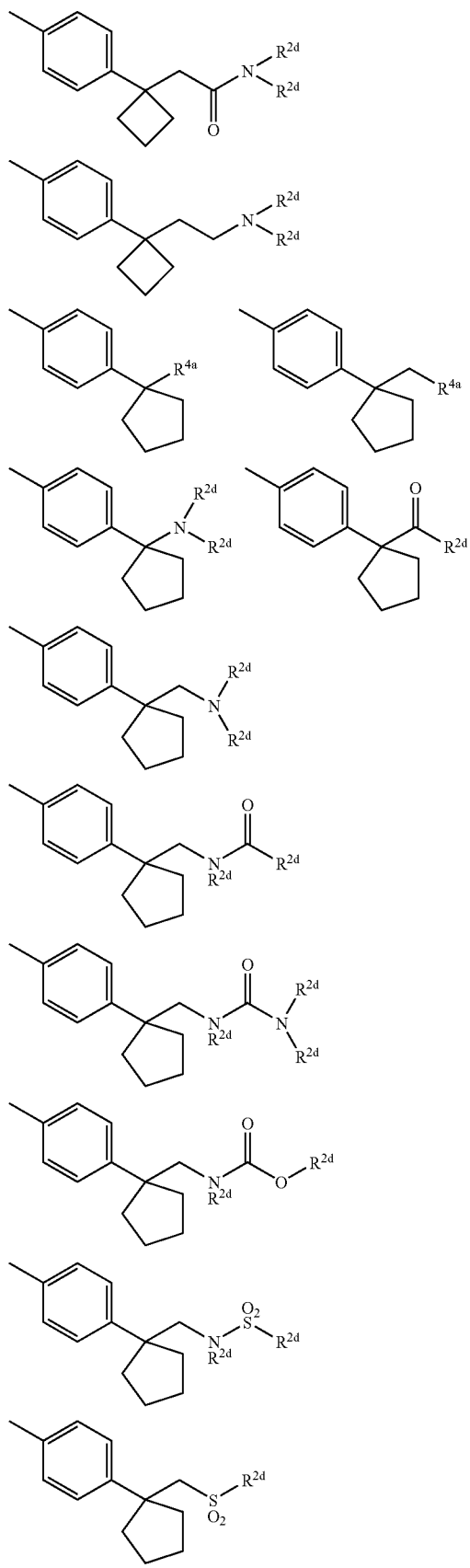
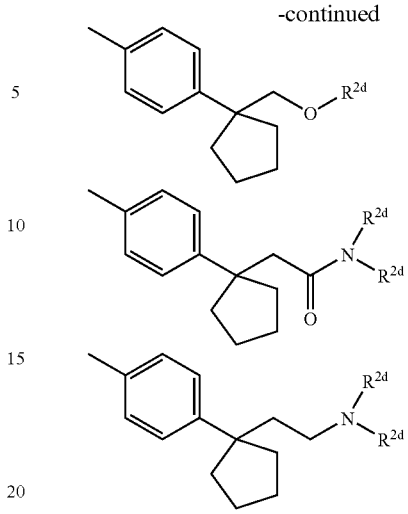

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2CCH$, $CH_2CH_2OH$, $CH_2C(O)NH_2$, cyclopropyl, $CH_2$-cyclopropyl, cyclobutyl, cyclopentyl, and thiazolyl;

$R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and, $R^{4c}$ is selected from =O, OH, $OCH_3$, and $CH_3$.

[7] In another embodiment, the present invention provides a novel compound, wherein the compound is of the formula:

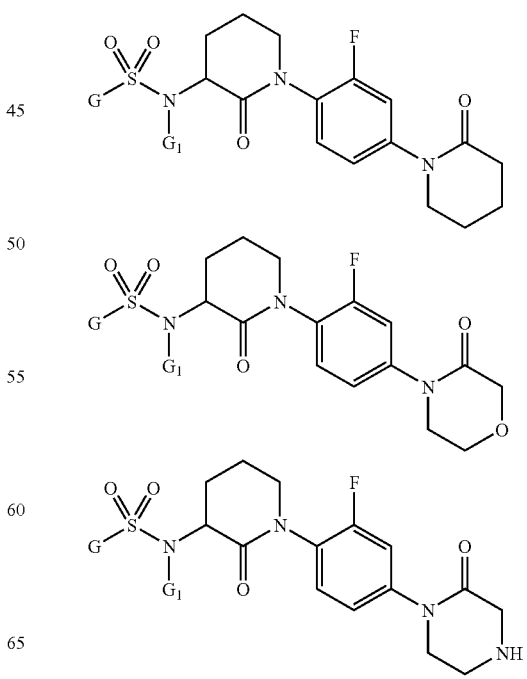

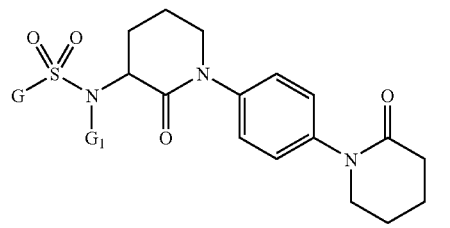
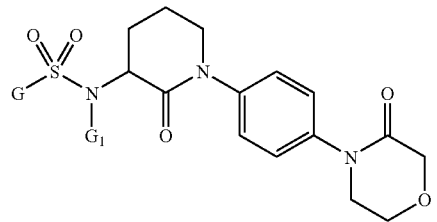
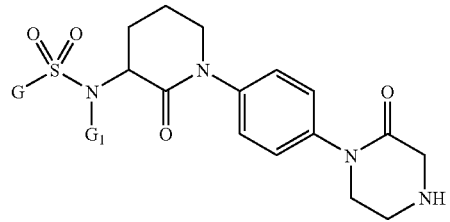
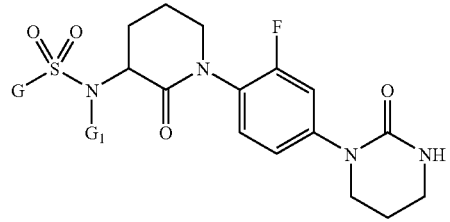
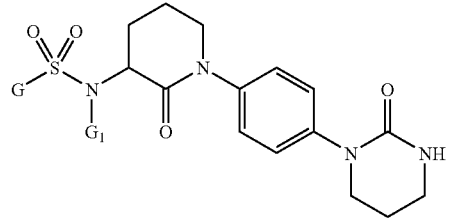
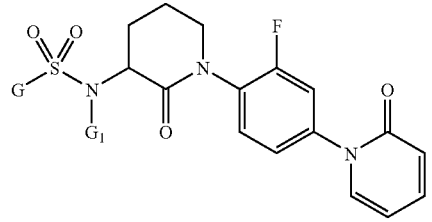
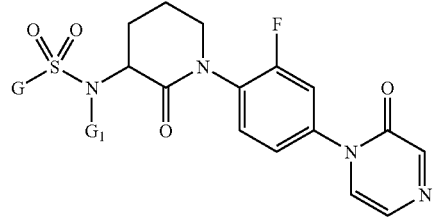
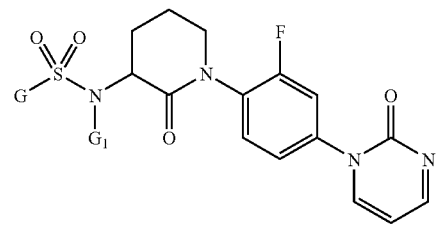
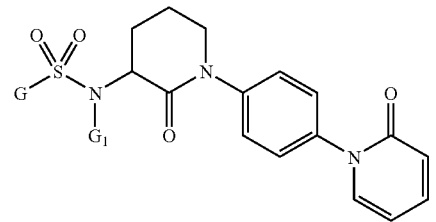
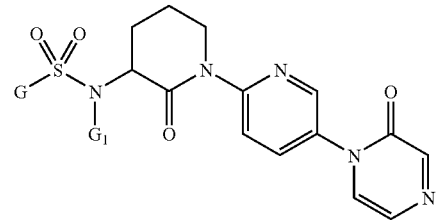
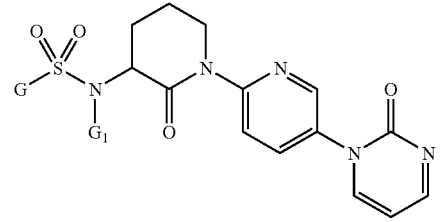
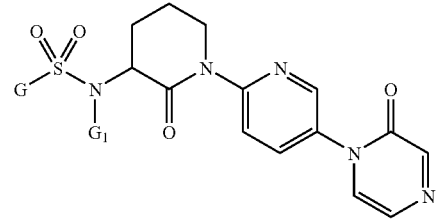
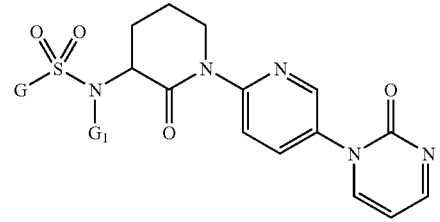
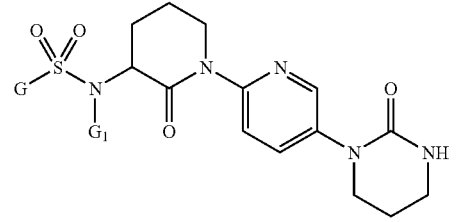

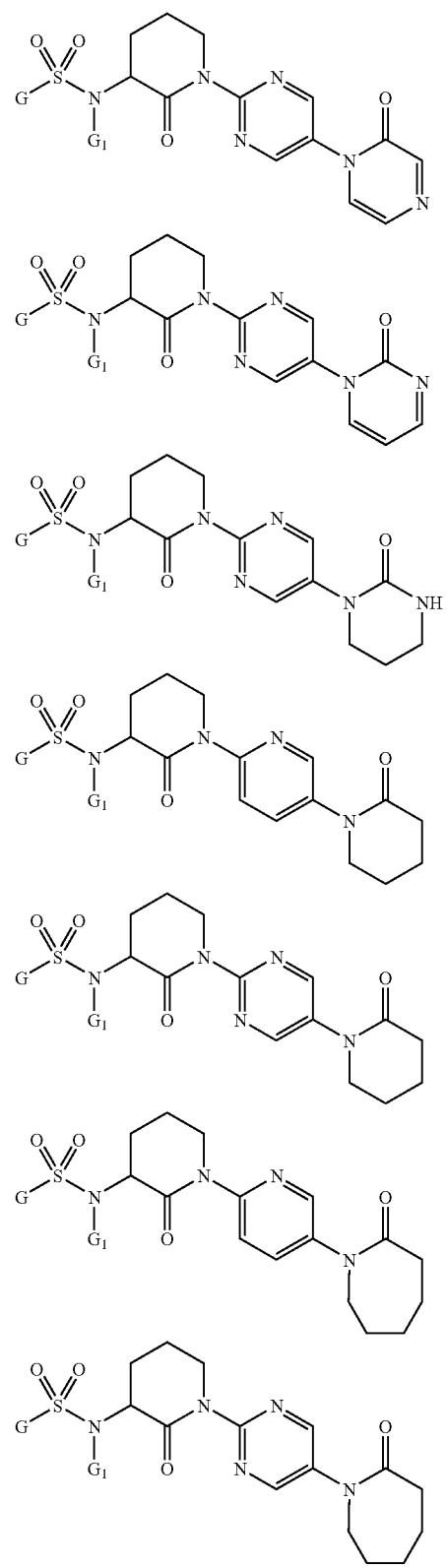
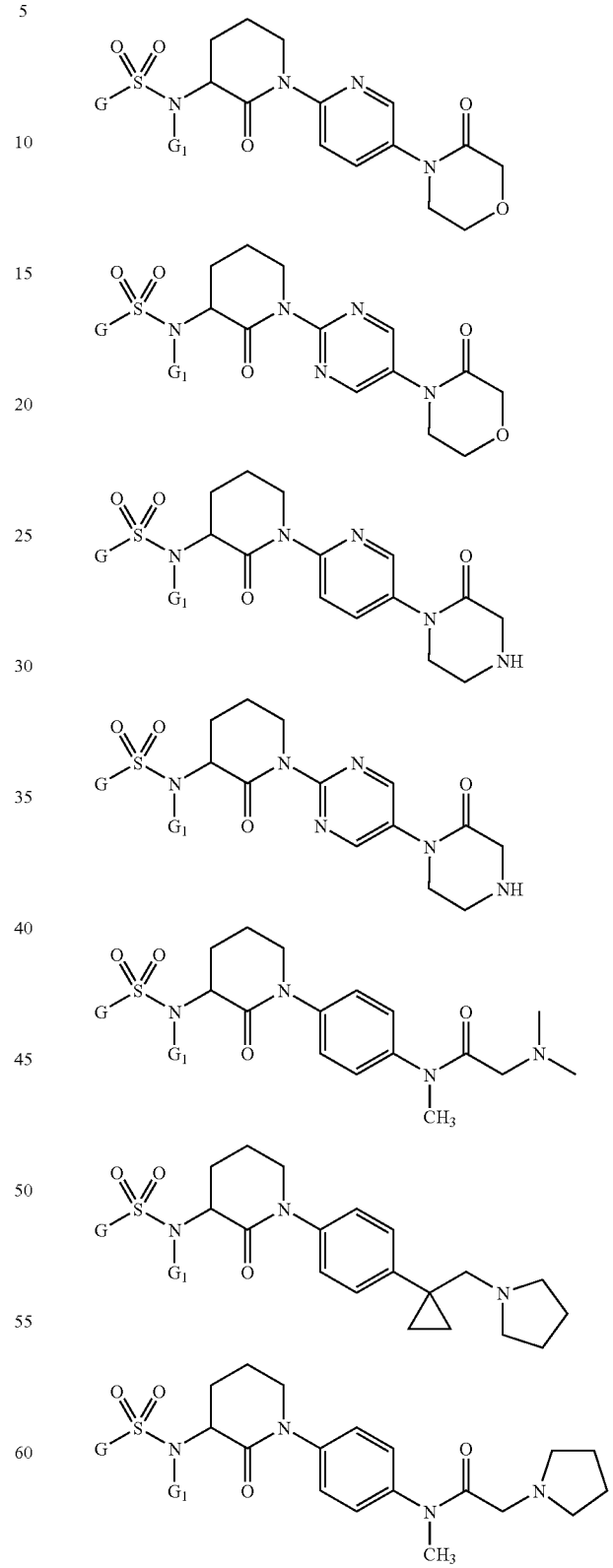

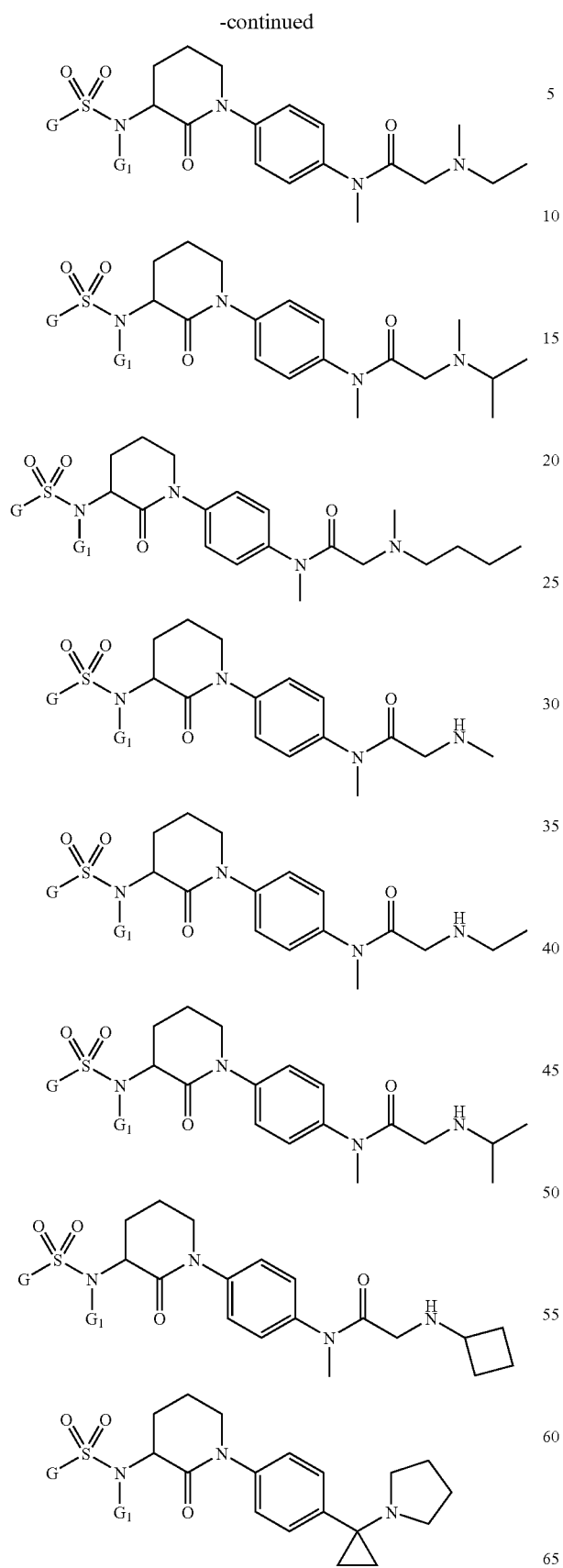
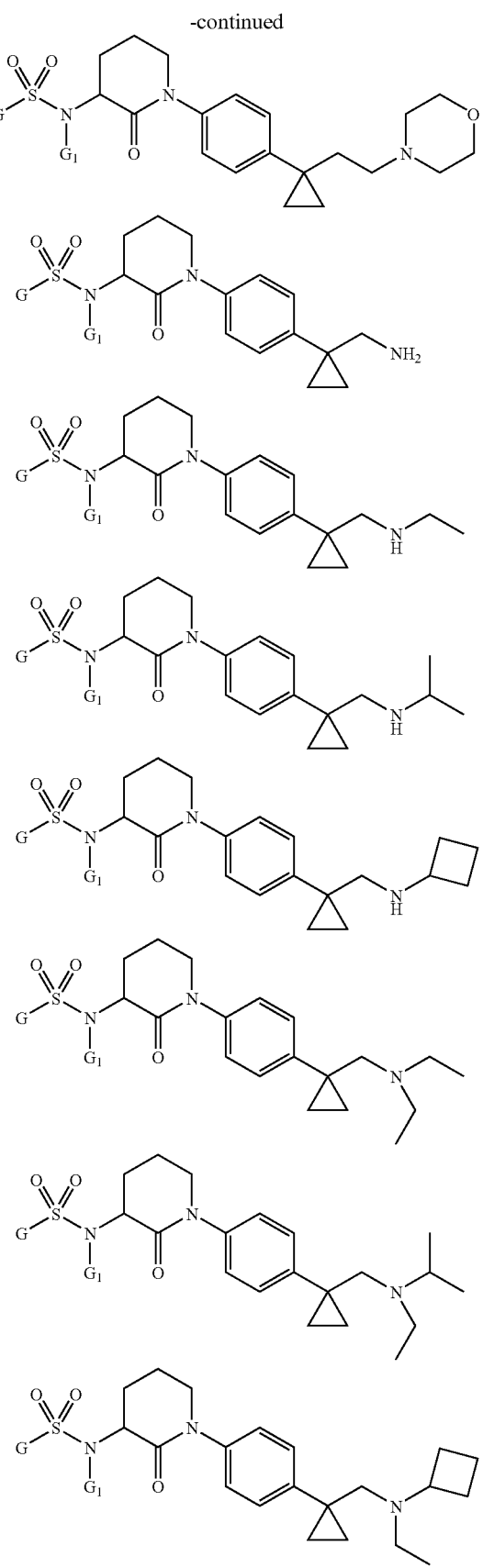

-continued
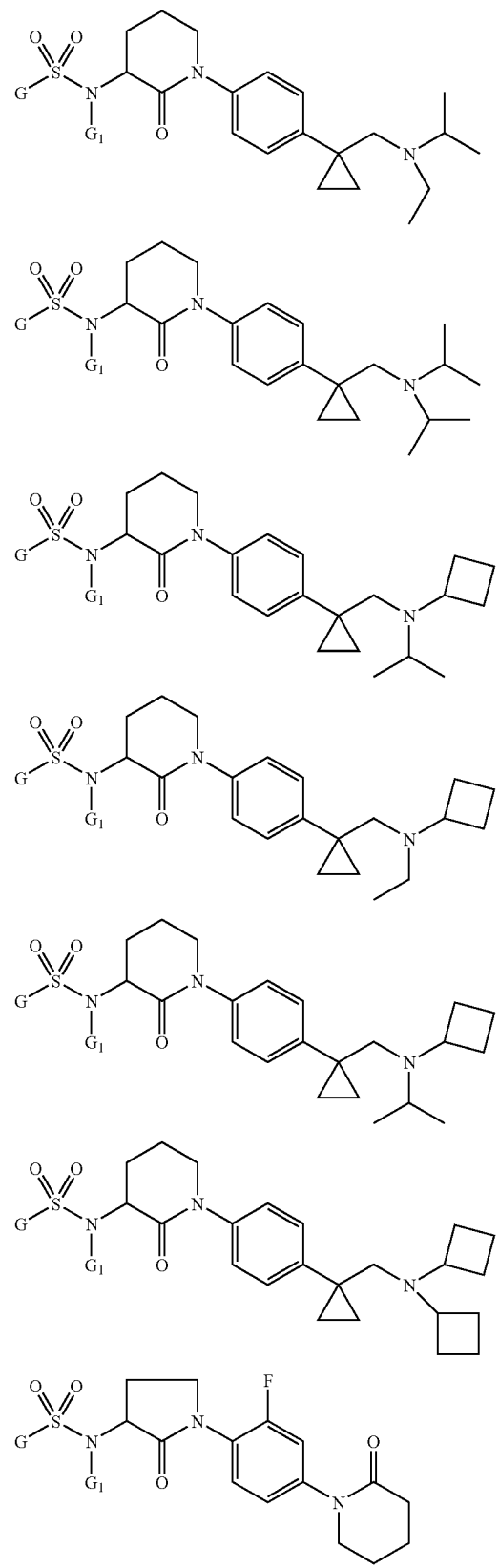
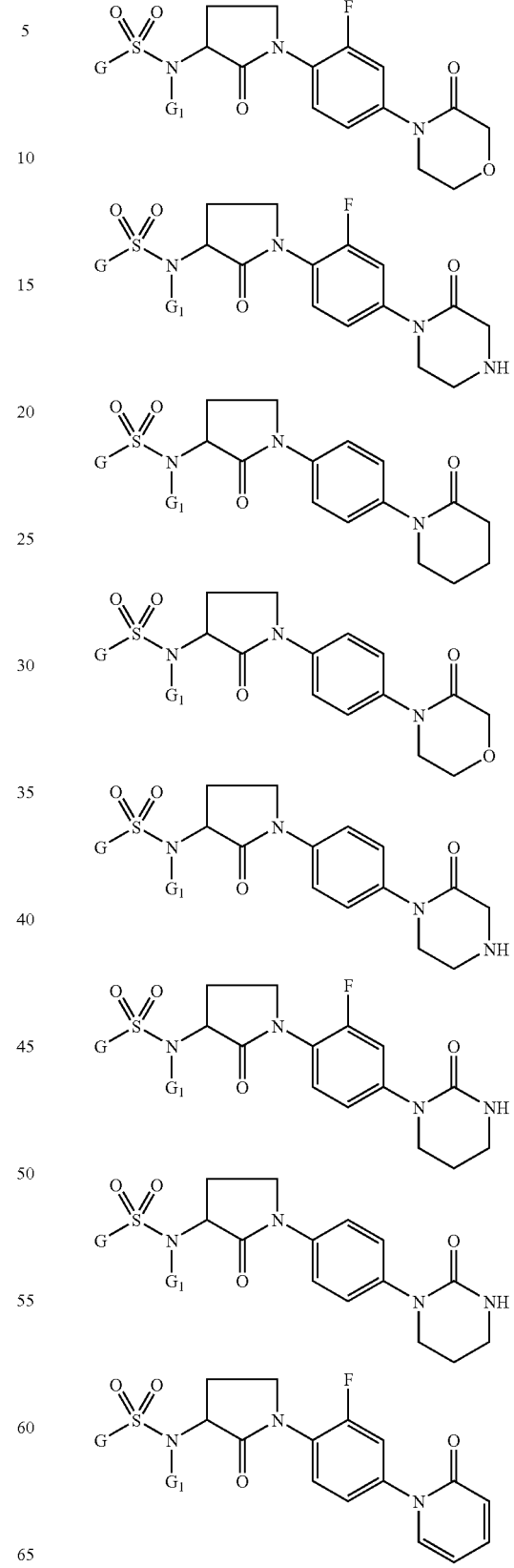

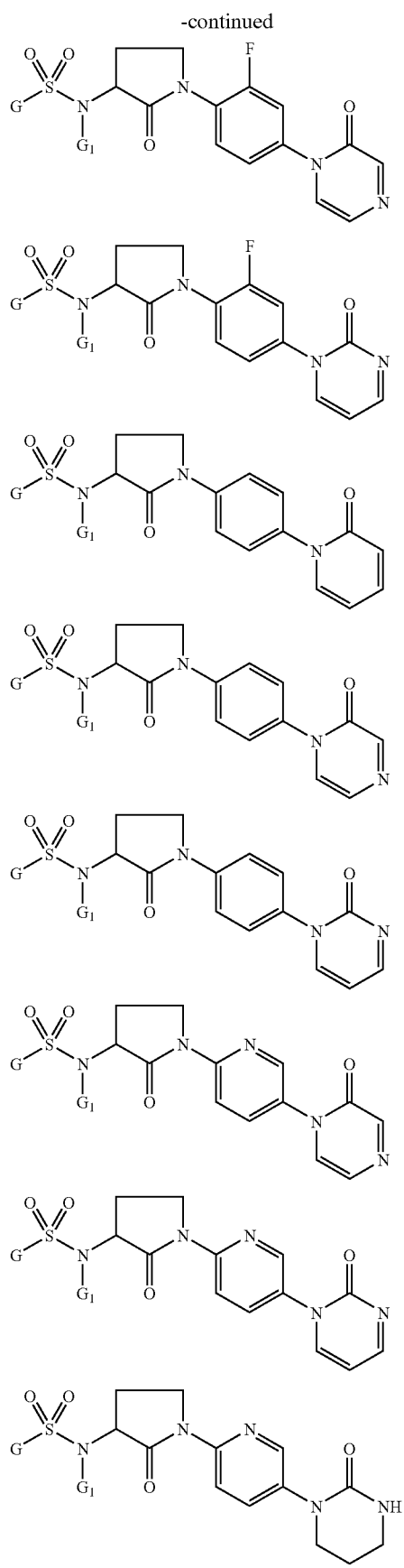
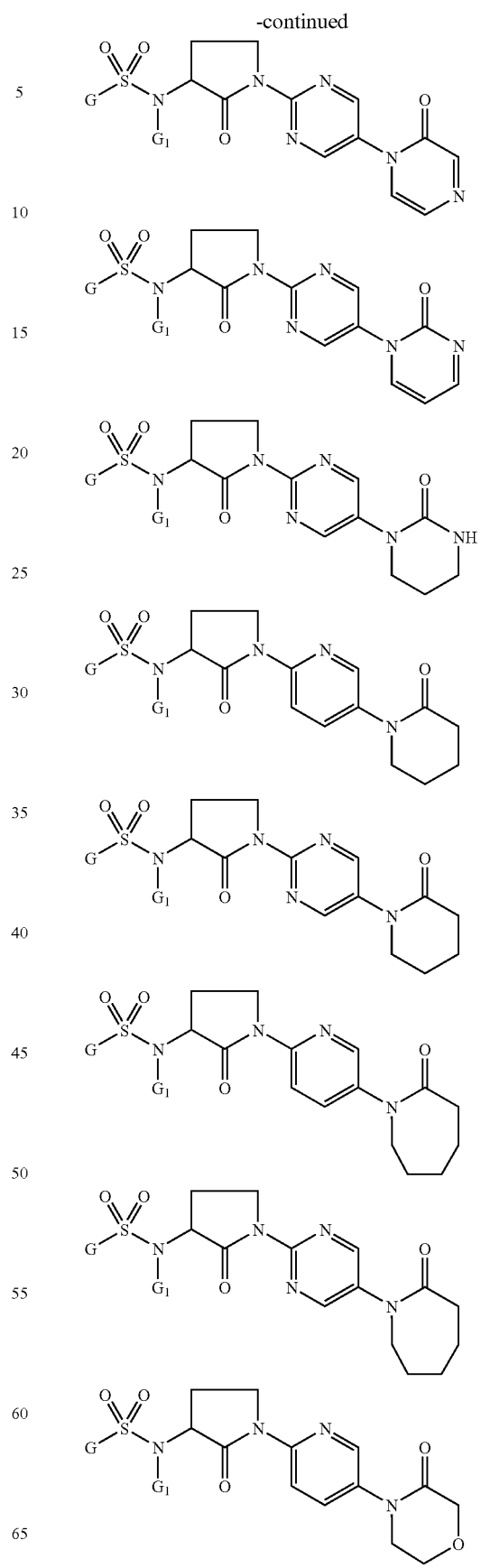

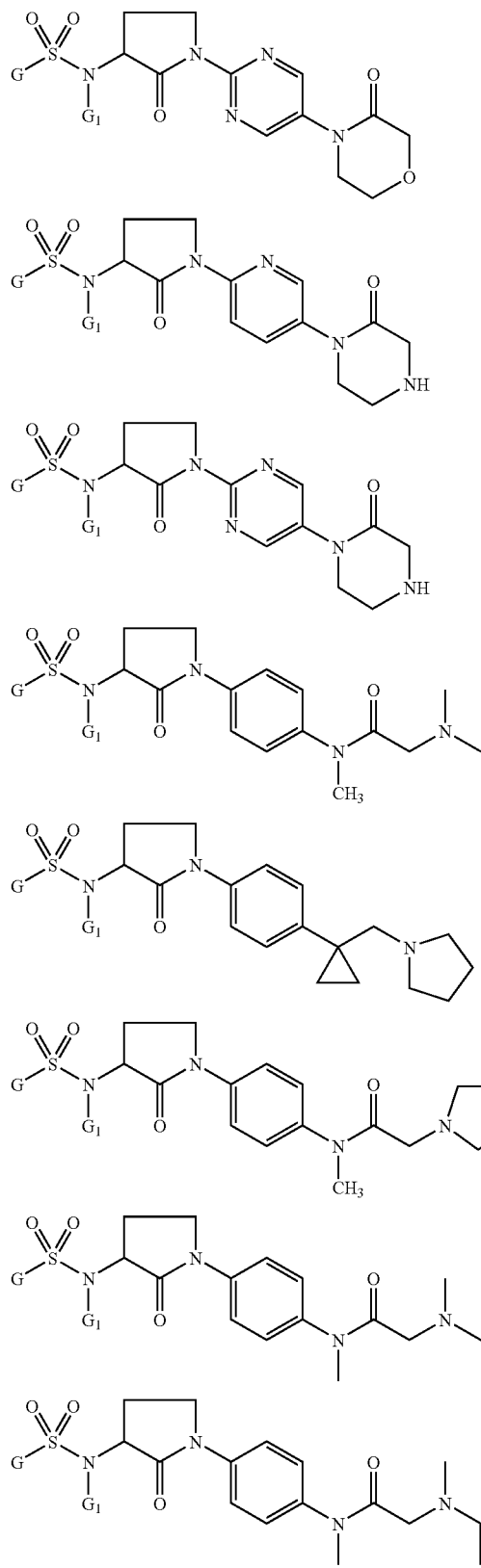
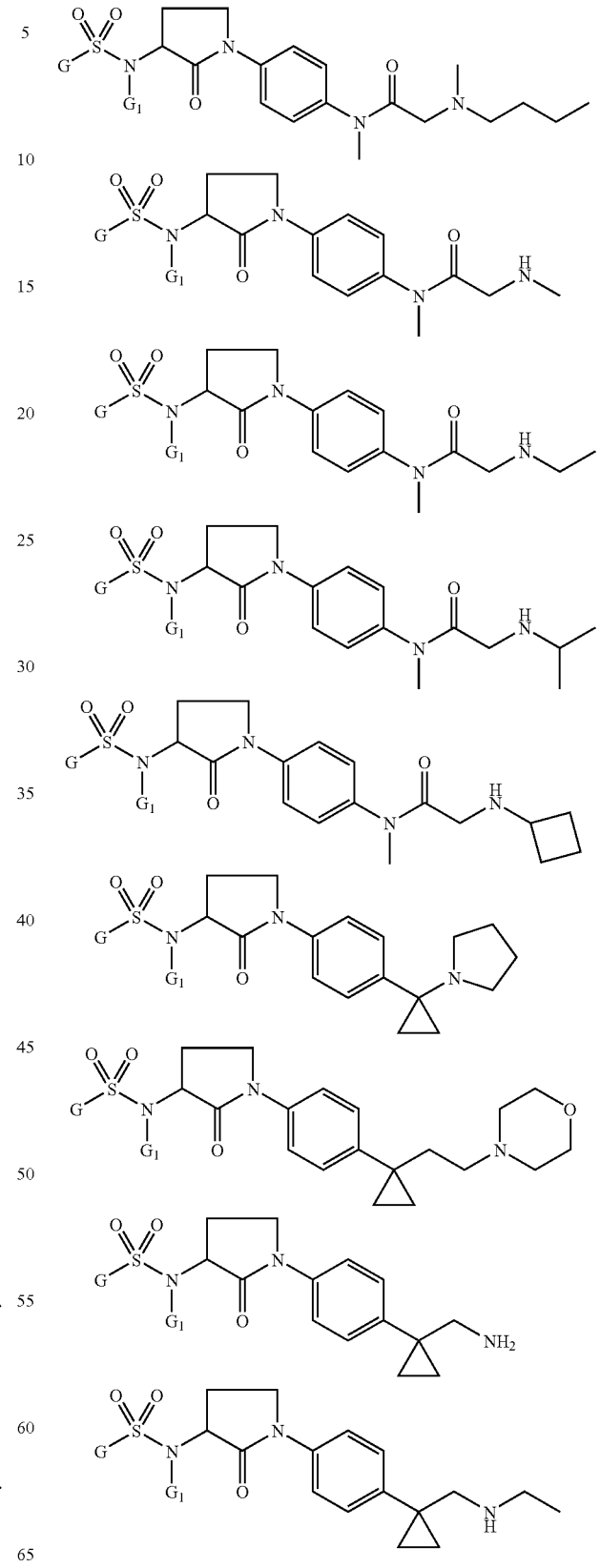

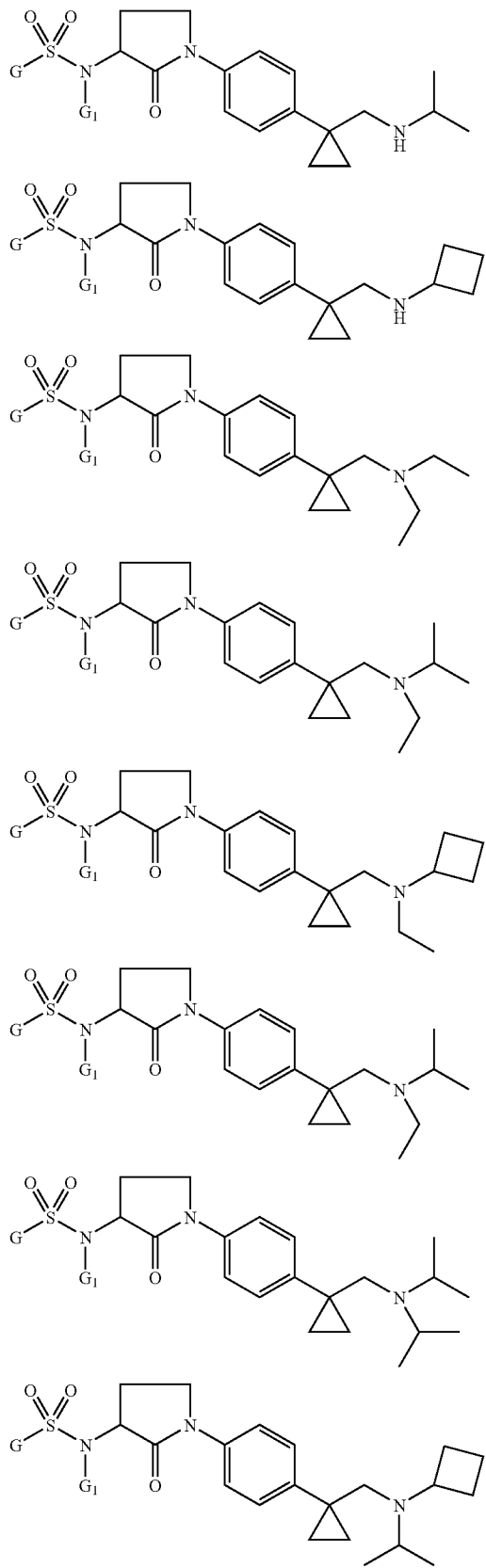
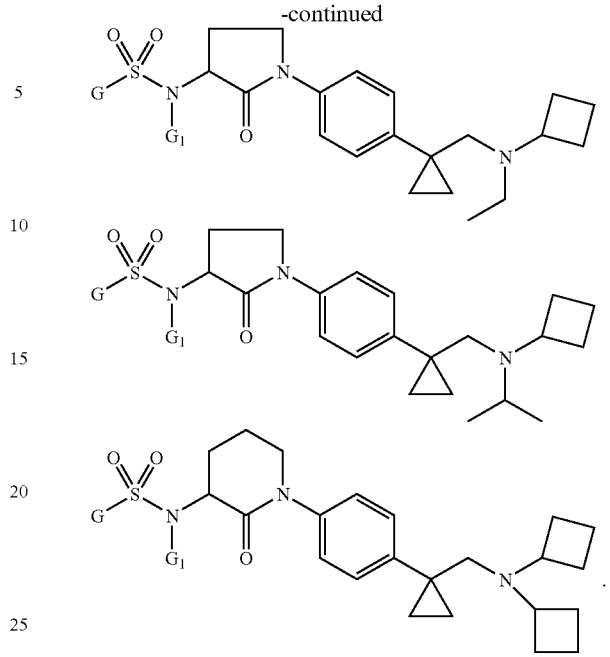

[8] In another, the present invention provides a novel compound, wherein the compound is selected from the group:

a) 6-Chloronaphthalene-2-sulfonic acid{1-[2-fluoro-4-(2-oxo-piperidin-1-yl)-phenyl]-2-oxopiperidin-3-yl}-amide;

b) 6-Chloronaphthalene-2-sulfonic acid{1-[2-fluoro-4-(2-oxo-2H-pyridin-1-yl)phenyl]-2-oxopiperidin-3-yl}amide;

c) 6-Chlorothieno[2,3-b]pyridine-2-sulfonic acid{1-[2-fluoro-4-(2-oxo-2H-pyridin-1-yl)phenyl]-2-oxopiperidin-3-yl}amide;

d) 2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

e) (R)-2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

f) (S)-2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

g) 2-((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-N-methylacetamide;

h) 2-((6-Chlorothieno[2,3-b]pyridine-2-sulfonyl)-{1-[2-fluoro-4-(2-oxo-2H-pyridin-1-yl)phenyl]-2-oxo-piperidin-3-yl}-amino)-N-(2-dimethylaminoethyl)-N-methylacetamide;

i) 6-Chloronaphthalene-2-sulfonic acid{1-[4-(2-oxo-2H-pyridin-1-yl)-phenyl]-2-oxo-piperidin-3-yl}amide;

j) 6-Chlorothieno[2,3-b]pyridine-2-sulfonic acid{1-[4-(2-oxo-2H-pyridin-1-yl)phenyl]-2-oxopiperidin-3-yl}amide; and, k) 2-((6-Chloronaphthalene-2-sulfonyl)-{1-[2-fluoro-4-(2-oxo-piperidin-1-yl)-phenyl]-2-oxo-piperidin-3-yl}amino)-N-(2-dimethylaminoethyl)-N-methylacetamide;

l) 2-[(6-Chloronaphthalene-2-sulfonyl)-{1-[2-fluoro-4-(2-oxo-piperidin-1-yl)-phenyl]-2-oxopiperidin-3-yl]-amino}-N-methyl-N-(1-methylpiperidin-4-yl)-acetamide;

m) 6-Chloro-naphthalene-2-sulfonic acid)-{1-[2-fluoro-4-(2-oxo-piperidin-1-yl)-phenyl]-2-oxo-piperidin-3-yl]-[2-(4-methyl-piperazin-1-yl)-2-oxo-ethyl]-amide n) 6-Chloronaphthalene-2-sulfonic acid)-{1-[2-fluoro-4-(2-oxo-piperidin-1-yl)-phenyl]-2-oxopiperidin-3-yl]-(2-morpholin-4-yl-2-oxoethyl)amide;

o) 2-{(6-Chlorothieno[2,3-b]pyridine-2-sulfonyl)-[1-[2-fluoro-4-(2-oxo-piperidin-1-yl)-phenyl]-2-oxopiperidin-3-yl]-amino}-N-methyl-N-(1-methylpiperidin-4-yl)-acetamide;

p) 6-Chlorothieno[2,3-b]pyridine-2-sulfonic acid)-{1-[2-fluoro-4-(2-oxo-piperidin-1-yl)-phenyl]-2-oxo-piperidin-3-yl]-[2-(4-methyl-piperazin-1-yl)-2-oxo-ethyl]-amide;

q) 6-Chlorothieno[2,3-b]pyridine-2-sulfonic acid)-{1-[2-fluoro-4-(2-oxo-piperidin-1-yl)-phenyl]-2-oxopiperidin-3-yl]-(2-morpholin-4-yl-2-oxoethyl)amide; and r) 2-((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-N,N-dimethylacetamide;

s) N-{4-[3-(6-Chloro-naphthalene-2-sulfonylamino)-2-oxo-piperidin-1-yl]-phenyl}-2-dimethylamino-N-methyl-acetamide;

t) N-{4-[3-(6-Chloro-naphthalene-2-sulfonylamino)-2-oxo-piperidin-1-yl]-phenyl}-N-methyl-2-pyrrolidin-1-yl-acetamide;

u) N-{4-[3-(6-Chloro-naphthalene-2-sulfonylamino)-2-oxo-piperidin-1-yl]-phenyl}-2-dimethylamino-N-methylacetamide;

v) N-{4-[3-(6-Chloro-thieno[2,3-b]pyridine-2-sulfonylamino)-2-oxo-piperidin-1-yl]-phenyl}-2-dimethylamino-N-methyl-acetamide;

w) 6-Chloro-naphthalene-2-sulfonic acid methyl-{2-oxo-1-[4-(2-oxo-2H-pyridin-1-yl)-phenyl]-piperidin-3-yl}-amide;

x) 6-Chloro-thieno[2,3-b]pyridine-2-sulfonic acid methyl-{2-oxo-1-[4-(2-oxo-2H-pyridin-1-yl)-phenyl]-piperidin-3-yl}-amide;

y) 6-Chloro-naphthalene-2-sulfonic acid ethyl-{2-oxo-1-[4-(2-oxo-2H-pyridin-1-yl)-phenyl]-piperidin-3-yl}-amide;

z) 6-Chloro-thieno[2,3-b]pyridine-2-sulfonic acid ethyl-{2-oxo-1-[4-(2-oxo-2H-pyridin-1-yl)-phenyl]-piperidin-3-yl}-amide;

aa) 2-((6-Chloro-thieno[2,3-b]pyridine-2-sulfonyl)-{2-oxo-1-[4-(2-oxo-2H-pyridin-1-yl)-phenyl]-piperidin-3-yl}-amino)-acetamide;

bb) 6-Chloro-naphthalene-2-sulfonic acid cyanomethyl-{2-oxo-1-[4-(2-oxo-2H-pyridin-1-yl)-phenyl]-piperidin-3-yl}-amide;

cc) 6-Chloro-naphthalene-2-sulfonic acid {2-oxo-1-[4-(2-oxo-2H-pyridin-1-yl)-phenyl]-piperidin-3-yl}-thiazol-4-ylmethyl-amide;

dd) 6-Chloro-naphthalene-2-sulfonic acid {2-oxo-1-[4-(2-oxo-2H-pyridin-1-yl)-phenyl]-piperidin-3-yl}-pyridin-3-ylmethyl-amide;

ee) 6-Chloro-naphthalene-2-sulfonic acid {2-oxo-1-[4-(2-oxo-2H-pyridin-1-yl)-phenyl]-piperidin-3-yl}-pyridin-2-ylmethyl-amide;

ff) 6-Chloro-naphthalene-2-sulfonic acid {2-oxo-1-[4-(2-oxo-2H-pyridin-1-yl)-phenyl]-piperidin-3-yl}-pyridin-4-ylmethyl-amide;

gg) 2-((6-Chloro-naphthalene-2-sulfonyl)-{2-oxo-1-[4-(2-oxo-2H-pyridin-1-yl)-phenyl]-piperidin-3-yl}-amino)-N-methyl-acetamide;

hh) 2-((6-Chloro-naphthalene-2-sulfonyl)-{2-oxo-1-[4-(2-oxo-2H-pyridin-1-yl)-phenyl]-piperidin-3-yl}-amino)-acetamide;

ii) 6-Chloro-naphthalene-2-sulfonic acid (2-methyl-thiazol-4-ylmethyl)-{2-oxo-1-[4-(2-oxo-2H-pyridin-1-yl)-phenyl]-piperidin-3-yl}-amide;

jj) 4-Methoxy-N-{2-oxo-1-[4-(2-oxo-2H-pyridin-1-yl)-phenyl]-piperidin-3-yl}-benzenesulfonamide;

kk) 5-Chloro-thiophene-2-sulfonic acid {2-oxo-1-[4-(2-oxo-2H-pyridin-1-yl)-phenyl]-piperidin-3-yl}-amide;

ll) 3-Chloro-N-{2-oxo-1-[4-(2-oxo-2H-pyridin-1-yl)-phenyl]-piperidin-3-yl}-benzenesulfonamide;

mm) ((4-Methoxy-benzenesulfonyl)-{2-oxo-1-[4-(2-oxo-2H-pyridin-1-yl)-phenyl]-piperidin-3-yl}-amino)-acetic acid methyl ester;

nn) ((5-Chloro-thiophene-2-sulfonyl)-{2-oxo-1-[4-(2-oxo-2H-pyridin-1-yl)-phenyl]-piperidin-3-yl}-amino)-acetic acid methyl ester;

oo) 2-((4-Methoxy-benzenesulfonyl)-{2-oxo-1-[4-(2-oxo-2H-pyridin-1-yl)-phenyl]-piperidin-3-yl}-amino)-acetamide;

pp) ((6-Chloro-naphthalene-2-sulfonyl)-{2-oxo-1-[4-(2-oxo-2H-pyridin-1-yl)-phenyl]-piperidin-3-yl}-amino)-acetic acid tert-butyl ester;

qq) 2-((5-Chloro-thiophene-2-sulfonyl)-{2-oxo-1-[4-(2-oxo-2H-pyridin-1-yl)-phenyl]-piperidin-3-yl}-amino)-acetamide;

rr) ((6-Chloro-naphthalene-2-sulfonyl)-{2-oxo-1-[4-(2-oxo-2H-pyridin-1-yl)-phenyl]-piperidin-3-yl}-amino)-acetic acid;

ss) 5-Chloro-thieno[3,2-b]pyridine-2-sulfonic acid {2-oxo-1-[4-(2-oxo-2H-pyridin-1-yl)-phenyl]-piperidin-3-yl}-amide;

tt) 5'-Chloro-[2,2']bithiophenyl-5-sulfonic acid {2-oxo-1-[4-(2-oxo-2H-pyridin-1-yl)-phenyl]-piperidin-3-yl}-amide;

uu) 2-((6-Chloro-naphthalene-2-sulfonyl)-{2-oxo-1-[4-(2-oxo-2H-pyridin-1-yl)-phenyl]-piperidin-3-yl}-amino)-N-(2-hydroxy-ethyl)-acetamide;

vv) N-Carbamoylmethyl-2-((6-chloro-naphthalene-2-sulfonyl)-{2-oxo-1-[4-(2-oxo-2H-pyridin-1-yl)-phenyl]-piperidin-3-yl}-amino)-acetamide;

ww) 6-Chloro-naphthalene-2-sulfonic acid {2-oxo-1-[4-(2-oxo-piperidin-1-yl)-phenyl]-pyrrolidin-3-yl}-amide;

xx) 6-Chloro-naphthalene-2-sulfonic acid {2-oxo-1-[4-(2-oxo-2H-pyridin-1-yl)-phenyl]-pyrrolidin-3-yl}-amide;

yy) 6-Chloro-naphthalene-2-sulfonic acid {2-oxo-1-[4-(1-pyrrolidin-1-ylmethyl-cyclopropyl)-phenyl]-piperidin-3-yl}-amide;

zz) 6-Chloro-thieno[2,3-b]pyridine-2-sulfonic acid {2-oxo-1-[4-(1-pyrrolidin-1-ylmethyl-cyclopropyl)-phenyl]-piperidin-3-yl}-amide;

aaa) ((5'-Chloro-[2,2']bithiophenyl-5-sulfonyl)-{2-oxo-1-[4-(2-oxo-2H-pyridin-1-yl)-phenyl]-piperidin-3-yl}-amino)-acetic acid methyl ester bbb) ((5-Chloro-thieno[3,2-b]pyridine-2-sulfonyl)-{2-oxo-1-[4-(2-oxo-2H-pyridin-1-yl)-phenyl]-piperidin-3-yl}-amino)-acetic acid methyl ester ccc) 2-((6-Chloro-naphthalene-2-sulfonyl)-{2-oxo-1-[4-(2-oxo-2H-pyridin-1-yl)-phenyl]-piperidin-3-yl}-amino)-acetic acid methyl ester ddd) 2-((6-Chlorothieno[2,3-b]pyridine-2-sulfonyl)-{2-oxo-1-[4-(2-oxo-2H-pyridin-1-yl)-phenyl]-piperidin-3-yl}-amino)-acetic acid methyl ester or a pharmaceutically acceptable salt form thereof.

[9] In another embodiment, the present invention provides a novel compound, wherein the compound is selected from the group:

a) 2-{(6-Chloronaphthalene-2-sulfonyl)-[1-(3-fluoro-2'-methanesulfonylbiphenyl-4-yl)-2-oxopiperidin-3-yl]-amino}-N-methyl-N-(1-methylpiperidin-4-yl)-acetamide;

b) 6-Chloro-naphthalene-2-sulfonic acid [1-(3-fluoro-2'-methanesulfonyl-biphenyl-4-yl)-2-oxo-piperidin-3-yl]-[2-(4-methyl-piperazin-1-yl)-2-oxo-ethyl]-amide;

c) 6-Chloronaphthalene-2-sulfonic acid [1-(3-fluoro-2'-methanesulfonylbiphenyl-4-yl)-2-oxopiperidin-3-yl]-(2-morpholin-4-yl-2-oxoethyl)amide;

d) 2-{(6-Chloronaphthalene-2-sulfonyl)-[1-(3-fluoro-2'-methanesulfonylbiphenyl-4-yl)-2-oxopiperidin-3-yl]-amino}-N-(2-hydroxyethyl)-N-methylacetamide;

e) 6-Chloro-naphthalene-2-sulfonic acid [1-(3-fluoro-2'-methanesulfonylbiphenyl-4-yl)-2-oxopiperidin-3-yl]-(3-hydroxy-propyl)amide;

f) 6-Chloronaphthalene-2-sulfonic acid {1-[4-(2-dimethylaminomethylimidazol-1-yl)-2-fluorophenyl]-2-oxopiperidin-3-yl}amide;

g) 6-chlorothieno[2,3-b]pyridine-2-sulfonic acid {1-[4-(2-dimethylaminomethylimidazol-1-yl)-2-fluorophenyl]-2-oxopiperidin-3-yl}amide;

h) 5-chlorothieno[3,2-b]pyridine-2-sulfonic acid {1-[4-(2-dimethylaminomethylimidazol-1-yl)-2-fluorophenyl]-2-oxopiperidin-3-yl}amide;

i) 5-chlorobenzothienyl-2-sulfonic acid {1-[4-(2-dimethylaminomethylimidazol-1-yl)-2-fluorophenyl]-2-oxopiperidin-3-yl}amide;

j) 6-Chlorothieno[2,3-b]pyridine-2-sulfonic acid {1-[4-(2-methylaminomethylimidazol-1-yl)-2-fluoro-phenyl]-2-oxo-piperidin-3-yl}amide; and k) ((6-Chlorothieno[2,3-b]pyridine-2-sulfonyl)-{1-[2-fluoro-4-(2-methylaminomethylimidazol-1-yl)phenyl]-2-oxo-piperidin-3-yl}amino)acetic acid methyl ester;

or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container; wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a compound of the present invention for use in therapy.

In another embodiment, the present invention provides the use of a compound of the present invention as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxinidolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Compounds of this invention can be prepared as shown in Scheme 1, wherein an appropriately substituted 4-iodo or 4-bromoaniline 1a is converted to 3-hydroxyvalerolactam 1b by a four-step sequence. The aniline is reacted with tetrahydrofuryl-2-carbonyl chloride (prepared from the corresponding acid by treatment with oxalylchloride and DMF) in the presence of a base such as triethylamine or N,N-dimethylaminopyridine to provide the amide. Treatment of this amide with boron tribromide provides the ring-opened 5-bromo-2-hydroxyvaleramide. The hydroxyl group is then protected as the corresponding acetate by treatment with acetic anhydride, followed by cyclization to the 3-acetoxy-valerolactam by refluxing with a base such as diisopropylamine in a suitable solvent such as N,N-dimethylacetamide. The acetate is subsequently hydrolyzed by treatment with potassium carbonate in methanol to give the 3-hydroxylactam intermediate 1b. Introduction of the B moiety is accomplished by Ullmann, Goldberg, Buchwald copper catalyzed amidation depending on the nature of B, using methods known to one skilled in the art for these types of couplings (see for example Lindley, *Tetrahedron* 1984, 40, 1433; Yin & Buchwald *Organic Lett.* 2000, 2, 1101; Klapers et al. *JACS*, 2001, 123, 7727; Kiyomor, Madoux & Buchwald, *Tet. Lett.*, 1999, 40, 2657). The resulting hydroxylactam 1c is then converted to the corresponding aminolactam 1d by a three step process. The hydroxyl group is either displaced by bromide, which can be accomplished either by treatment with carbon tetrabromide and triphenylphosphine or by treatment with phosphorous tribromide in a solvent such as methylene chloride, or alternately it is converted to the mesylate by treatment with mesylchloride in the presence of a suitable base such as triethylamine or diisopropylethylamine. Displacement of either the bromide or mesylate with azide is readily accomplished by heating in the presence of sodium azide in a polar solvent such as N,N-dimethylformamide. The azide is then reduced to amine 1d using any of a variety of methods known in the art for the transformation of azides to amines, for example, catalytic hydrogenation over a Pd catalyst, Staudinger reduction with triphenylphosphine or reduction with tin(II)chloride. Reaction of amine 1d with an appropriate sulfonyl chloride provides sulfonamide derivatives 1e, which can be further derivatized by alkylation on the sulfonamide nitrogen via treatment with an alkyl bromide in the presence of a suitable base such as potassium carbonate to provide compounds of this invention of formula 1f.

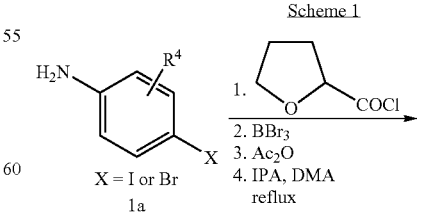

Scheme 1

-continued

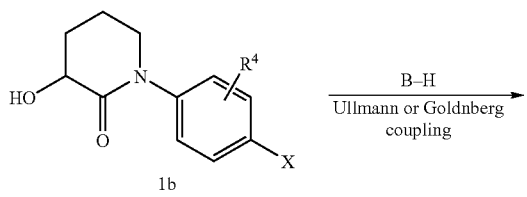
1b

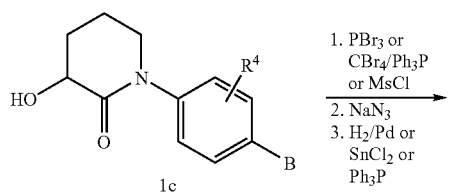
1c

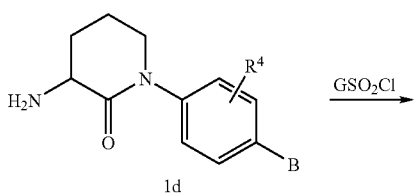
1d

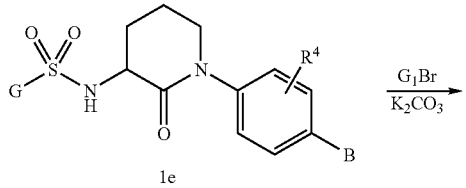
1e

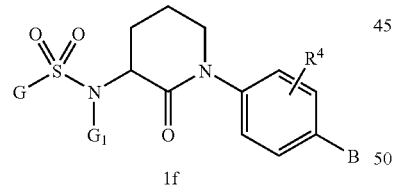
1f formation of amide bonds to provide compounds of formula 2c. Suitable coupling reagents for this reaction include carbodiimide reagents, Castro's reagent, 1,1-carbonyldiimidazole, mixed anhydride coupling methods, etc.

Scheme 2

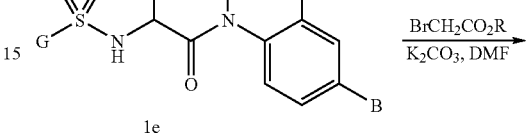
1e

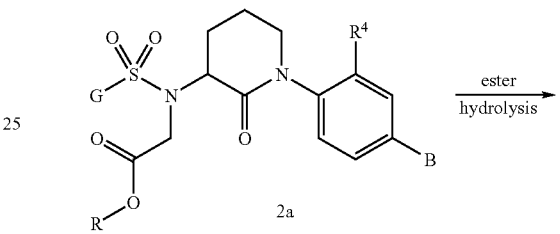
2a

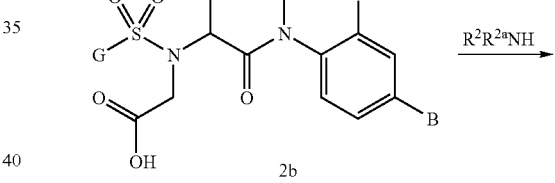
2b

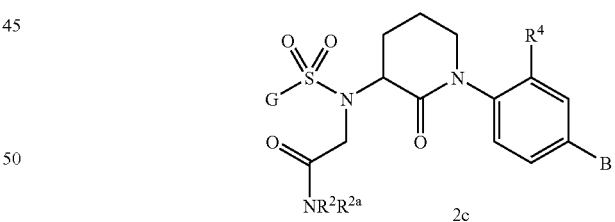
2c

Compounds of this invention with $R^3$ groups specifically derived from an acetic acid substituent are prepared as outlined in Scheme 2. Treatment of sulfonamide derivatives, 1e, with an ester of 2-bromoacetic acid, for example t-butyl or methyl bromoacetate, in the presence of a base such as potassium carbonate in a polar solvent such as DMF provides alkylated compounds 2a. Hydrolysis of the ester either by saponification, in the case of a methyl or ethyl ester, or by treatment with TFA, in the case of the t-butyl ester, provides acid 2b which can be reacted with an appropriate amine under various conditions known in the literature for Alternately, the fully elaborated A-B moiety can be prepared as the aniline intermediate, which can then undergo conversion to aminovalerolactams of formula 1d using the methods described above. Thus, the starting 4-iodoaniline is amidated via Ullmann or Buchwald methodology as illustrated in Scheme 3 to provide 3a or 3b which can be subsequently converted to the corresponding 3-aminovalerolactams and on to the sulfonamide targets following the steps shown in Schemes 1 and 2 above.

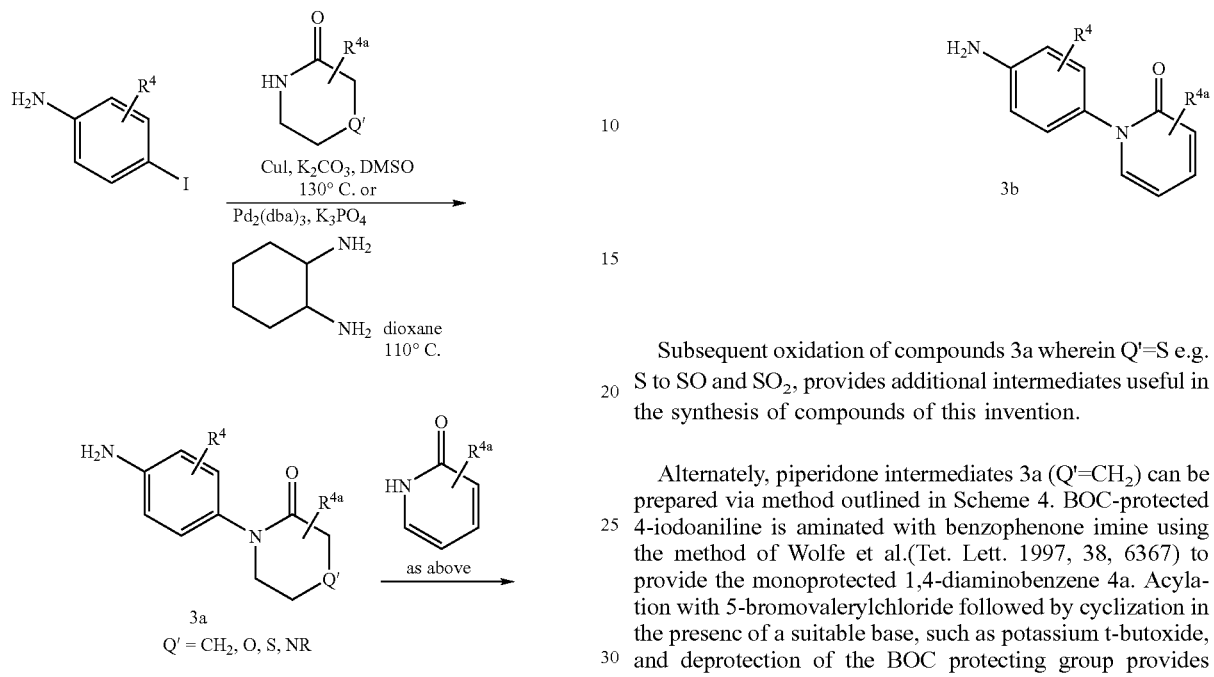

Subsequent oxidation of compounds 3a wherein Q'=S e.g. S to SO and SO$_2$, provides additional intermediates useful in the synthesis of compounds of this invention.

Alternately, piperidone intermediates 3a (Q'=CH$_2$) can be prepared via method outlined in Scheme 4. BOC-protected 4-iodoaniline is aminated with benzophenone imine using the method of Wolfe et al.(Tet. Lett. 1997, 38, 6367) to provide the monoprotected 1,4-diaminobenzene 4a. Acylation with 5-bromovalerylchloride followed by cyclization in the presenc of a suitable base, such as potassium t-butoxide, and deprotection of the BOC protecting group provides aniline 4b.

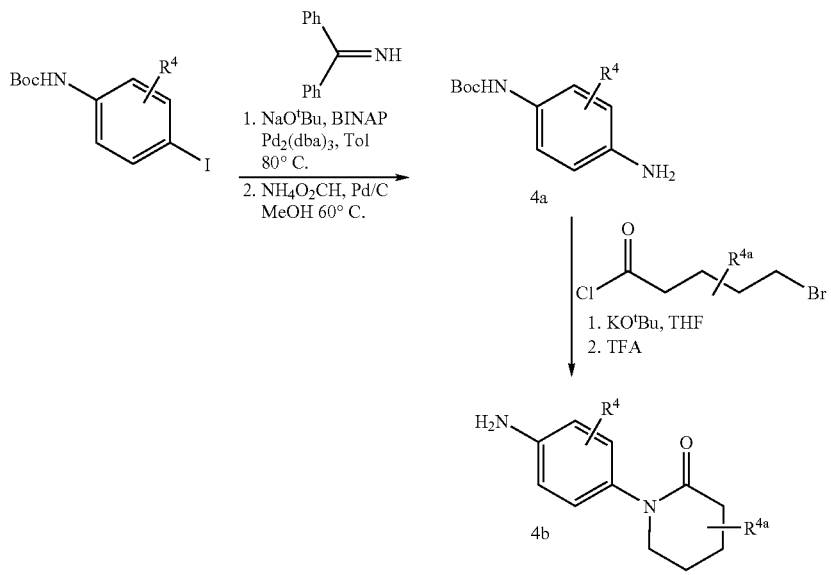

Similarly, the Ullmann coupling methodology can also be applied to prepare urea analogs 5a as shown in scheme 5.

Scheme 5

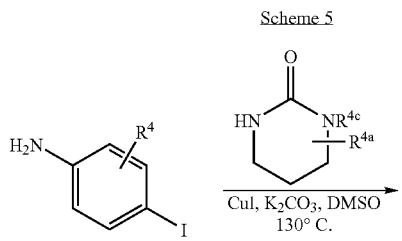

-continued

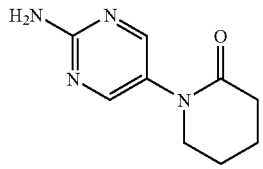

4d

Compounds of this invention wherein A is a non-aromatic carbocycle can be prepared from intermediate amine compounds shown in scheme 6 via procedures known to those skilled in the art.

Scheme 6

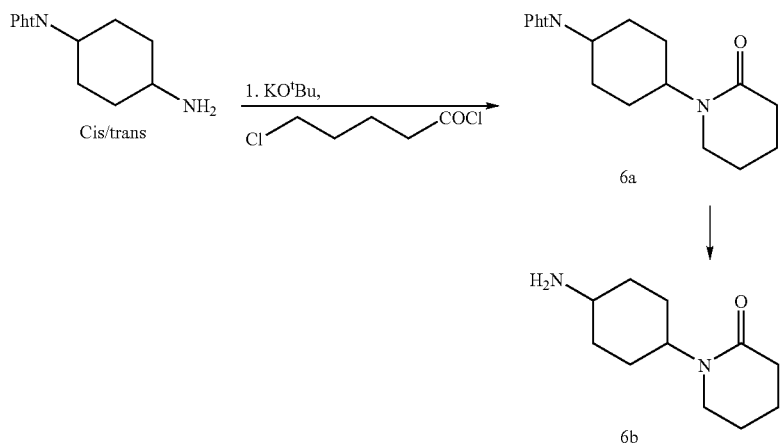

-continued

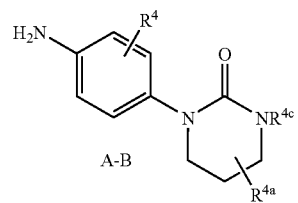

A-B

Substitution of 5-bromo-2-aminopyridine or 5-bromo-2-aminopyrimidine for the 4-iodoanilines in the above Schemes provides additonal intermediates 4c and 4d useful in Scheme 1 for the synthesis of compounds of the present invention whrein A is a pyridyl or pyrimidinyl moiety.

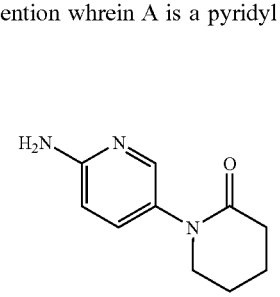

4c

Compounds of this invention wherein B is amino acid derivatives can be prepared by following Scheme 7. Thus, 8a can be converted to 8b via protection, methylation, and deprotection. Acylation of the analine followed by amination of the terminal chloride can provide 8d. Coupling of 8d with the lactam intermediate as described previously can give compound 8e, which can be transformed to desired compound 8f upon deprotection and sulfonation.

Scheme 7

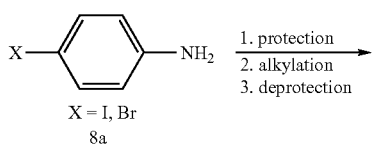

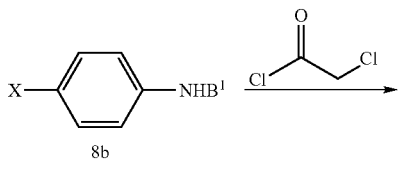

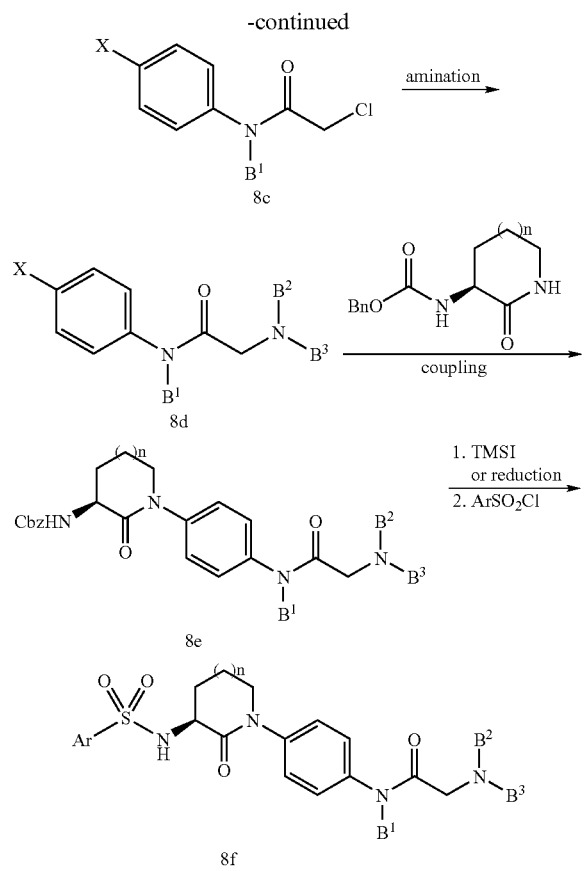

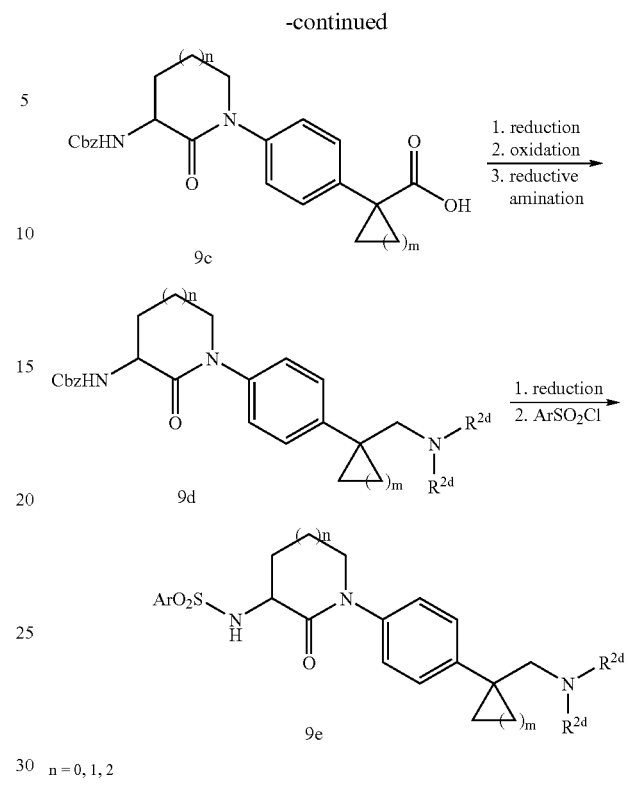

Alternatively, the pyrrolidinone derivatives can be obtained as described in Scheme 9.

Compounds of this invention wherein B is an 1,1-disubstituted cycloalkyl derivative can be prepared as described in Scheme 8. Halogenation of 9a can provide the corresponding 9b, which under Ullmann condition can be converted to 9c. Reduction of the carboxylic acid group followed by oxidation can give the corresponding aldehyde, which under reductive amination condition can be transformed to 9d. Deprotection and sulfonation provides the desired compound of this invention 9e.

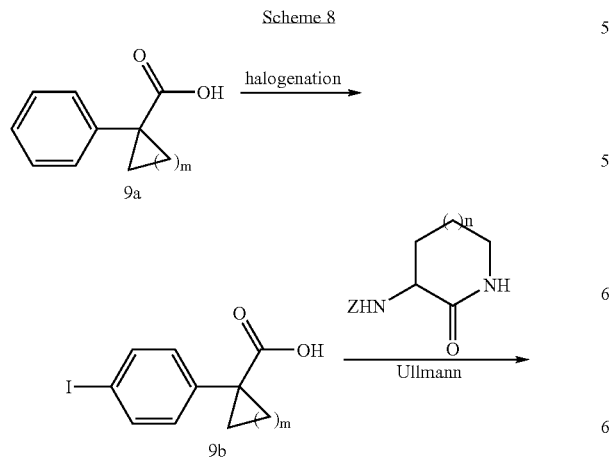

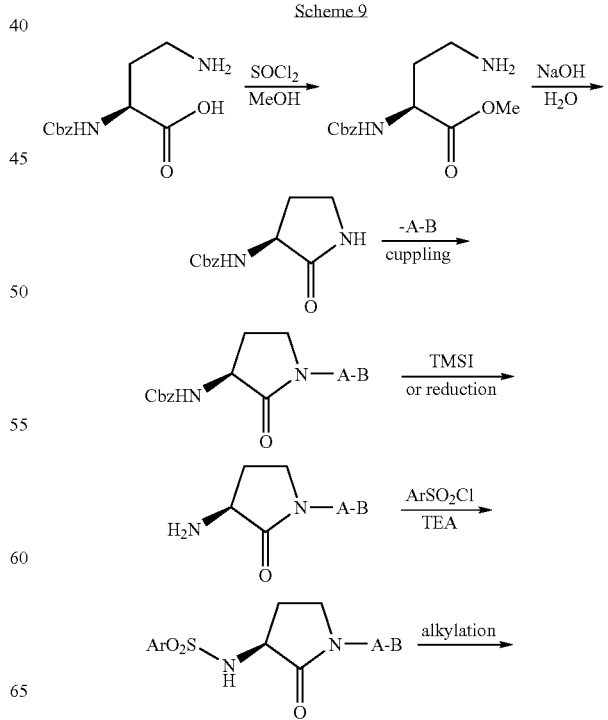

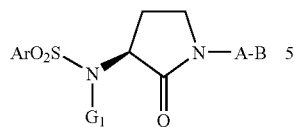
5

One stereoisomer of a compound of Formula I may display superior activity compared with the other. Thus, the following stereochemistries are considered to be a part of the present invention.

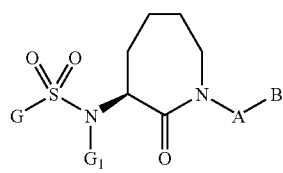 IIIa

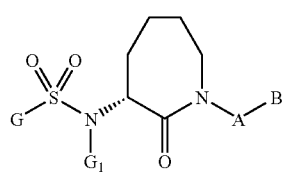 IIIb

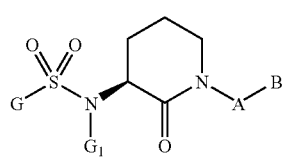 IIIc

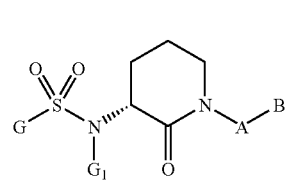 IIId

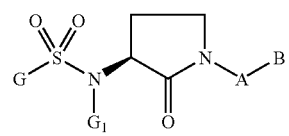 IIIe

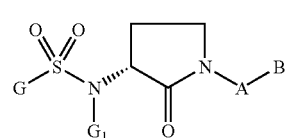 IIIf

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605.

Alternately, single stereoisomers can be obtained by chiral synthesis of (R) or (S)-3-aminovalerolactam 7f from (R) or (S)-ornithine derivative 7a as shown in Scheme 10.

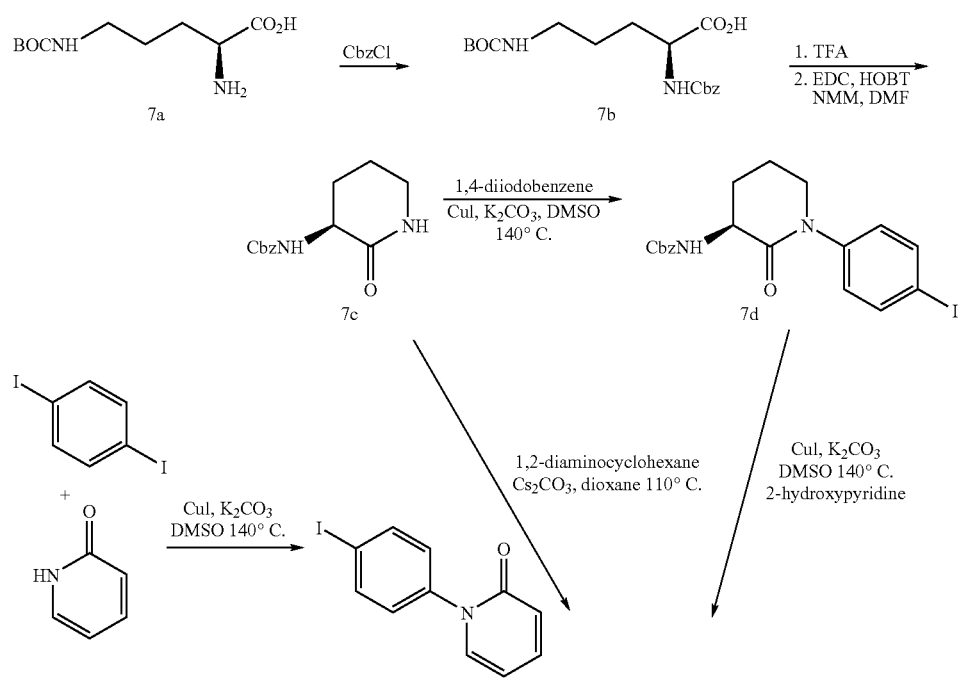

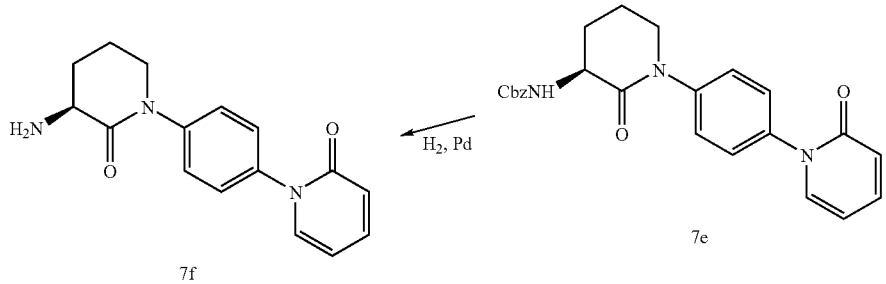

Other features of the invention will become apparent in the course of the following descriptions of exemplary embodiments that are given for illustration of the invention and are not intended to be limiting thereof.

EXAMPLES

Example 1

6-Chloronaphthalene-2-sulfonic acid {1-[2-fluoro-4-(2-oxo-piperidin-1-yl)-phenyl]-2-oxo-piperidin-3-yl}-amide Part A. Tetrahydro-furan-2-carboxylic acid (2-fluoro-4-iodophenyl)amide: Tetrahydro-2-furoic acid (4.9 g, 42.19 mmol) was dissolved in $CH_2Cl_2$ (250 mL), and oxalyl chloride (1.5 eq.) was added, followed by dropwise addition of DMF (0.5 mL). The resulting mixture was stirred at room temperature for 18 h. The solvent was removed in vacuo and the residue dried under vacuum, then dissolved in 250 mL $CH_2Cl_2$. To this solution was added 2-fluoro-4-iodoaniline (10 g, 42.19 mmol) and DMAP (12.9 g, 105.48 mmol), and the mixture was stirred at room temperature for 18 h. The solvent was removed and the crude product was purified by chromatography on silica gel (4:1/Hexane:EtOAc) to give the amide (13.4 g, 96%) as a solid. MS (API$^+$) m/z 335.9 [(M+H)$^+$ 15], 376.9 [(M+H+AcCN)$^+$ 100].

Part B. Acetic acid 1-(2-fluoro-4-iodophenyl)-2-oxo-piperidin-3-yl ester: Boron tribromide (3.78 mmol, 7.8 mL of a 1M solution in $CH_2Cl_2$) was added to a solution of the compound of Ex. 1, Part A (2.53 g, 7.55 mmol) in 40 mL $CH_2Cl_2$. The mixture was stirred at room temperature for 1.5 h and then evaporated to dryness in vacuo. The crude bromide was dissolved in heptane (100 mL) and $Ac_2O$ (1.54 g, 15.1 mmol) was added, after which the mixture was heated to reflux for 4 h. The reaction was cooled and concentrated, then quenched with 200 mL water, and extracted with EtOAc. The combined extracts were washed with $H_2O$, brine, dried over $MgSO_4$, filtered and concentrated to give a semi-solid mass (3.7 g). MS (ES$^-$) m/z 456.1; 458.1 [(M−H)$^-$ 80]. This product was dissolved in DMA (100 mL), and treated with diisopropylamine (2.3 g, 22.65 mmol), and the resulting mixture was heated to reflux for 18 h. The reaction was cooled to room temperature and quenched with 500 mL water, then extracted with EtOAc, washed with brine and dried over $MgSO_4$. After filtration and concentration, the crude was purified by chromatography on silica get (4:1/Hexane:EtOAc) to give the the desired acetoxylactam (2.7 g, 96%) MS (ES) m/z 441.0 [(M+Na+AcCN)$^+$ 100].

Part C. 1-(2-Fluoro-4-iodophenyl)-3-hydroxy-piperidin-2-one: The compound of Ex. 1, Part B (6.1 g, 16.18 mmol) was dissolved in a mixture of MeOH:$H_2O$ (50:3 mL) and $K_2CO_3$ (5.6 g, 40.45 mmol) was added. The resulting mixture was stirred at room temperature for 18 h. The solvent was removed in vacuo, water was added followed by extraction with EtOAc. The combined extracts were washed with brine, dried over $MgSO_4$, filtered and concentrated to give (5.3 g, 98%) the alcohol as a white solid. MS (ES) m/z 336.2 [(M+H)$^+$ 100].

Part D. 3-(t-Butyldimethylsilanyloxy)-1-(2-fluoro-4-iodophenyl)piperidin-2-one: A solution of the compound of Ex. 1, Part C (1 g, 2.98 mmol) and imidazole (0.9 g, 13.12 mmol) in 10 mL DMF was treated with t-butyldimethylsilyl chloride (1 g, 6.56 mmol), and the mixture was heated at 40° C. for 18 h. The reaction mixture was cooled to room temperature and diluted with 200 mL water, extracted into EtOAc, washed with water, brine and dried over $MgSO_4$, followed by filtration and concentration to give the silyl ether (1.5 g, >99%) MS (API$^+$) m/z 450.1 [(M+H)$^+$ 100].

Part E. 1-[3-fluoro-4-(3-hydroxy-2-oxopiperidin-1-yl)phenyl]piperidin-2-one: A mixture of the compound of Ex. 1, Part D, (0.5 g, 1.11 mmol), valerolactam (0.2 g, 2.22 mmol), $K_3PO_4$ (0.47 g, 2.22 mmol), 1,2-cyclohexyldiamine (13 mg, 0.11 mmol), and CuI (21 mg, 0.11 mmol) in 1 mL Dioxane was degassed with $N_2$ and heated at 85° C. for 18 hr. The solvent was removed in vacuo and 50 mL EtOAc was added. The mixture was filtered through a pad of Celite, concentrated and purified by prep C18 HPLC to give the deprotected product (0.12 g, 26%). MS (ES) m/z 307.3 [(M+H)$^+$ 100].

Part F. 1-[4-(3-bromo-2-oxopiperidin-1-yl)-3-fluorophenyl]piperidin-2-one: The compound of Ex. 1, Part E (0.12 g, 0.39 mmol) was dissolved in 10 mL $CH_2Cl_2$ and treated with $PBr_3$ (0.21 g, 0.78 mmol). The mixture was stirred at room temperature for 18 h then quenched with ice water, extracted into $CH_2Cl_2$, washed with brine, and dried over $MgSO_4$. After filtration and concentration, the crude product was purified by chromatography on silica gel (2% MeOH in $CH_2Cl_2$) to give the bromide (89 mg, 62%). MS (ESI) m/z 369.2 [(M+H)$^+$ 90].

Part G. 1-[4-(3-amino-2-oxopiperidin-1-yl)-3-fluorophenyl] piperidin-2-one: The compound of Ex. 1, Part F (89 mg, 0.24 mmol) was dissolved in 1 mL DMF and NaN$_3$ (47 mg, 0.73 mmol) was added. The resulting mixture was heated at 50° C. for 3 h. Solvent was removed in vacuo and the crude azide was dried under vacuum. MS (ESI) m/z 332.2 [(M+H)$^+$ 100]. A solution of the azide in MeOH was added to a suspension of SnCl$_2$ (68 mg, 0.36 mmol) in 2 mL MeOH, and then the mixture was stirred at room temperature for 18 h. The solvent was removed in vacuo and 10 mL 1 N NaOH solution was added, followed by extracted with CHCl$_3$. The combined extracts were washed with(brine and dried over MgSO$_4$. Filtration and concentration gave the crude amine (83 mg, >90%) as a white solid. MS (ESI) m/z 306.3 [(M+H)$^+$ 100].

Part H. 6-Chloronaphthalene-2-sulfonic acid {1-[2-fluoro-4-(2-oxo-piperidin-1-yl)phenyl]-2-oxo-piperidin-3-yl}amide: The compound of Ex. 1, Part G in a 1:1 mixture of 1M potassium charbonate solution and ethylacetate was treated with 1.2 eq of 6-chloronaphthalene-2-sulfonylchloride, and the resulting mixture stirred for 90 min under N$_2$. The reaction was then diluted with water and extracted #X with ethyl acetate. The combined organic layers were washed with brine and dried over sodium sulfate, filtered and evaporated in vacuo. Purification by flash chromatography provided the title compound. $^1$H NMR (CD$_3$OD) δ 8.49 (s, 1H), 8.02 (m, 2H), 7.93 (m, 2H), 7.57 (m, 1H), 7.25–7.04 (m, 3H), 4.08 (m, 1H), 3.61 (m, 4H), 2.49 (m, 2H), 2.26 (m, 1H), 2.01 (m, 3H), 1.92 (m, 4H). MS (ES) m/z 530.3 [(M+H)$^+$ 100].

Part I. {(6-Chloronaphthalene-2-sulfonyl)-[1-(3-fluoro-2'-methanesulfonylbiphenyl-4-yl)-2-oxo-piperidin-3-yl]amino}-acetic acid: A mixture of the compound of Ex. 1, Part H (0.50 g, 0.85 mmole), t-butyl bromoacetate (147 ul, 1.0 mmole), 1M potassium carbonate (10 mL) and ethyl acetate (10 mL) was stirred under nitrogen for 24 h. The mixture was diluted with water and extracted with ethyl acetate (3×50 mL), washed with brine, dried over sodium sulfate and concentrated. The crude ester was taken up in methylene chloride and 3 mL of TFA was added. This mixture was stirred for 2 h at room temperature then concentrated and dried under vacuum to give the desired product. (0.24 g, 44% yield). $^1$H (CDCl$_3$) δ 8.47 (s, 1H), 8.22–8.19 (d, 1H, J=1.5 Hz), 7.91 (s, 4H), 7.66–7.55 (m, 3H), 7.34–7.31 (d, 1H, J=1.5 Hz), 7.26–7.21 (m, 3H), 3.82–3.79 (m, 1H), 3.66–3.52 (m, 2H), 2.71 (s, 3H), 2.63 (m, 1H), 2.03–1.98 (m, 2H). MS (ESI+) m/z 645.3 (M+1)$^+$.

Part J. 2-{(6-Chloronaphthalene-2-sulfonyl)-[1-(3-fluoro-2'-methanesulfonylbiphenyl-4-yl)-2-oxo-piperidin-3-yl]-amino}-N-(2-dimethylaminoethyl)-N-methylacetamide, trifluoroacetate: A solution of the compound of Ex. 1, Part H (25 mg, 0.004 mmole),N,N,N'-trimethylethylenediamine (6.0 mg, 0.006 mmole), and 4-methylmorpholine (11 ul) and DMF (1 mL) was treated with Castro's Reagent (26 mg, 0.006 mmole), and the resulting mixture was stirred under nitrogen for an additional 48 h. The crude mixture was evaporated in vacuo and purified by prep LC/MS to provide the title compound (18 mg, 64%). $^1$H (75% CD$_3$OD:25% C$_6$D$_6$) δ 8.58 (s, 1H), 8.14–8.12 (d, 1H, J=5.78 Hz.), 7.99–7.98 (d, 1H, J=11.5 Hz), 7.92–7.90 (d,1H,J=11.5 Hz), 7.86–7.85 (m, 2H), 7.58–7.55 (m, 1H), 7.52–7.48 (m, 2H), 7.20–7.15 (m,3H), 4.77–4.76 (m,1H), 4.23–4.11 (dd, 2H, J=20.2,J=37.1), 3.69–3.61 (m, 2H), 3.47–3.42 (m, 1H), 3.37–3.35 (m, 1H), 3.30–3.12 (m, 2H), 3.05 (s, 1H), 2.79 (s, 9H), 2.27–2.25 (m, 1H), 2.14 (bs, 1H), 1.91–1.75 (m, 2H). MS (ESI$^+$) 729.0 (M+1)$^+$.

Example 2

6-Chloronaphthalene-2-sulfonic acid {1-[2-fluoro-4-(2-oxo-2H-pyridin-1-yl)phenyl]-2-oxo-piperidin-3-yl}amide Part A: 1-[3-Fluoro-4-(3-hydroxy-2-oxo-piperidin-1-yl)phenyl]-1H-pyridin-2-one: A mixture of the compound of Ex. 1, Part C (1 g, 2.98 mmole), 2-hydroxypyridine (1.4 g, 14.93 mmole), K$_2$CO$_3$ (4.1 g, 29.85 mmole) and CuI (0.28 g, 1.49 mmole) in DMSO (15 mL) was degassed and then heated at 140° C. for 3 h. The reaction was cooled to room temperature and 50 mL of saturated NH$_4$Cl soln. was added. Mixture was extracted with methylene chloride and the combined organic extracts were washed with water and brine then dried over anh. MgSO$_4$, filtered and concentrated in vacua. Crude extract was purified by silica gel chromatography (5% MeOH in CH$_2$Cl$_2$) to provide the product (0.5 g, 56%). MS m/z 303.2 (M+H)$^+$. $^1$H NMR (CDCl$_3$) δ 7.45–7.22 (m, 5H), 6.69 (m, 1H), 6.29 (m, 1H), 4.26 (m, 1H), 3.64 (m, 2H), 2.45 (m, 1H), 2.13 (m, 2H), 1.94 (m, 1H).

Part B. 1-[4-(3-amino-2-oxo-piperidin-1-yl)-3-fluorophenyl]-1H-pyridin-2-one: Phosphorus tribromide (0.9 g, 3.3 mmole) was added to a solution of the compound of Ex. 2, Part A (0.5 g, 1.65 mmole) in 20 mL methylene chloride and the mixture was stirred overnight at room temperature. Reaction was quenched by addition of water and layers separated. Aqueous was reextracted with CH$_2$Cl$_2$ and combined extracts washed with brine, dried over MgSO$_4$, filtered and concentrated in vacuo to give the bromide (0.46 g, 77%) which was used without purification. The bromide was dissolved in DMF (5 mL) and treated with sodium azide (0.33 g, 5.05 mmole). The mixture was heated in a 50° C. oil bath for 3 h. Reaction was cooled to room temperature, poured into water and extracted into EtOAc. Purification on silica gel (2% MeOH in CH$_2$Cl$_2$) provided the azide (0.31 g, 76%). A mixture of the azide and SnCl$_2$ (0.27 g, 1.42 mmole) in methanol (10 mL) was stirred at room temperature overnight. Solvent was removed in vacuo and 30 mL 1N NaOH was added to the residue followed by extraction with chloroform. Extracts were combined, washed with brine, dried and concentrated to dryness in vacuo to provide the amine (0.24 g, 86%). $^1$H NMR (CDCl$_3$) δ 7.41 (m, 2H), 7.37 (m, 2H), 7.24 (m, 1H), 6.67 (m, 1H), 6.27 (m, 1H), 3.67 (m, 3H), 2.35 (m, 1H), 2.05 (m, 2H), 1.95 (m, 1H). MS m/z 302.3 (M+H)$^+$.

Part C. 6-Chloronaphthalene-2-sulfonic acid [1-(2-fluoro-4-pyridin-4-yl-phenyl)-2-oxo-piperidin-3-yl]amide: This compound was prepared from the compound of Ex. 2, Part B and 6-chloronaphthylsulfonyl chloride following the procedure described for Ex. 1, Part H to provide the title compound in 76% yield after prep C18 HPLC. $^1$H NMR (CD$_3$OD) δ 8.50 (s, 1H), 8.00 (m, 2H), 7.94 (s, 2H), 7.57 (m, 3H), 7.38 (m, 2H), 7.20 (m, 1H), 6.59 (m, 1H), 6.45 (m, 1H), 4.15 (m, 1H), 3.60 (m, 2H), 2.25 (m, 1H), 2.01 (m, 3H). MS (ESI$^+$) m/z 526.3 [(M+H)$^+$ 100].

Example 3

6-Chlorothieno[2,3-b]pyridine-2-sulfonic acid {1-[2-fluoro-4-(2-oxo-2H-pyridin-1-yl)phenyl]-2-oxopiperidin-3-yl}amide A mixture of the compound of Ex. 2, Part B (50 mg, 0.17 mmole), 6-chlorothieno[2,3-b]pyridine-2-sulfonylchloride (prepared as described in WO9937304, 53 mg, 0.199 mmole), 2 mL chloroform and 1 mL of a 1M solution of K$_2$CO$_3$ was stirred at room temperature overnight. Additional chloroform was added and the phases were separated. Organic layer was washed with brine and dried over MgSO$_4$, filtered and evaporated. Prep HPLC (C18) of the residue provided the title compound (60 mg, 68%). $^1$H NMR (CD$_3$CN) δ 8.27 (m, 1H), 7.93 (s, 1H), 7.49 (m, 2H), 7.37 (m, 2H), 7.23 (m, 2H), 6.49 (m, 2H), 6.27 (m, 1H), 4.13 (m, 1H), 3.61 (m, 2H), 2.35 (m, 2H), 2.04 (m, 2H). MS (ES) m/z 533.2 [(M+H)$^+$ 100].

Example 4

6-Chloronaphthalene-2-sulfonic acid {1-[4-(2-dimethylaminomethyl-imidazol-1-yl)-2-fluoro-phenyl]-2-oxo-piperidin-3-yl}-amide Part A. 1-[4-(2-Dimethylaminomethyl-imidazol-1-yl)-2-fluoro-phenyl]-3-hydroxy-piperidin-2-one: A mixture of the compound of Ex. 1, Part C (0.5 g, 1.49 mmole), 2-dimethylaminomethylimidazole (0.22 g, 1.79 mmole), K$_2$CO$_3$ (0.6 g, 4.5 mmole) and CuI (0.1 g, 0.746 mmole) in DMSO (10 mL) was degassed and then heated at 140° C. for 3 h. Cooled to room temperature and diluted with saturated NH$_4$Cl solution. Product was extracted into chloroform (3×), washed with brine, dried and evaporated. Flash chromatography on silica gel (2% MeOH in CH$_2$Cl$_2$) provided the product (0.35 g, 71%). $^1$H NMR (CDCl$_3$) δ 7.70 (m, 1H), 7.39 (m, 2H), 7.11 (m, 2H), 4.25 (m, 1H), 3.70 (m, 3H), 3.40 (2, 2H), 2.45 (m, 1H), 2.28 (s, 6H), 2.10 (m, 2H), 1.95 (m, 1H). MS m/z 333.3 (M+H)$^+$.

Part B. 3-amino-1-[4-(2-Dimethylaminomethyl-imidazol-1-yl)-2-fluoro-phenyl]piperidin-2-one: The compound of Ex. 4, Part A was converted in three steps into the corresponding amino compound as described in Part B of Ex. 2 above. MS m/z 332.3 (M+H)$^+$.

Part C. 6-Chloronaphthalene-2-sulfonic acid{1-[4-(2-dimethylaminomethyl-imidazol-1-yl)-2-fluoro-phenyl]-2-oxo-piperidin-3-yl}-amide: The title compound was prepared in 70% yield from the amine in Part B above and 6-chloronaphthylsulfonyl chloride following the procedure described for Ex. 1, Part H. $^1$H NMR (CD$_3$OD) δ 8.49 (x, 1H), 8.03 (m, 2H), 7.95 (s, 2H), 7.58 (m, 1H), 7.40 (m, 3H), 7.22 (m, 2H), 4.36 (s, 2H), 4.15 (m, 1H), 3.60 (m, 2H), 2.82 (s, 6H), 2.25 (m, 1H), 2.06 (m, 3H). MS (ES) m/z 556.4 [(M+H)$^+$ 100].

Similarly prepared from the compound of Ex. 4, Part B and the indicated sulfonyl chlorides were the following compounds in Table 2.

TABLE 2

| Ex. No. | RSO$_2$Cl | R | (M + H)$^+$ |
|---|---|---|---|
| 5 | 6-chlorothieno[2,3-b]pyridine-2-sulfonylchloride | 6-chlorothieno[2,3-b]pyridin-2-yl | 563.2 |
| 6 | 5-chlorothieno[3,2-b]pyridine-2-sulfonylchloride | 5-chlorothieno[3,2-b]pyridin-2-yl | 563.2 |
| 7 | 5-chlorobenzothienyl-2-sulfonylchloride | 5-chlorobenzothien-2-yl | 562.2 |

Example 8

6-Chlorothieno[2,3-b]pyridine-2-sulfonic acid {1-[4-(2-methylaminomethylimidazol-1-yl)-2-fluoro-phenyl]-2-oxo-piperidin-3-yl}amide, trifluoroacetate salt Part A. 1-[2-Fluoro-4-(2-methylaminomethylimidazol-1-yl)-phenyl]-3-hydroxy-piperidin-2-one, trifluoroacetate salt: This compound was prepared according to the procedure of Ex. 4, Part A from the compound of Ex. 1, Part C and 2-(methylaminomethyl)imidazole and isolated as its TFA salt in 44% yield after C18 HPLC. $^1$H NMR δ 7.57 (m, 1H), 7.42 (m, 2H), 7.34 (m, 1H), 7.19 (s, 1H), 4.31 (s, 2H), 4.25 (m, 1H), 3.72 (m, 1H), 3.62 (m, 1H), 2.75 (s, 3H), 2.25 (m, 1H), 2.12 (m, 2H), 1.95 (m, 1H). MS m/z 319.3 (M+H)$^+$.

Part B. 1{1-[3-Fluoro-4-(3-hydroxy-2-oxo-piperidin-1-yl)-phenyl]-1H-imidazol-2-ylmethyl}methylcarbamic acid t-butyl ester: A mixture of the compound of Ex. 18, Part A (0.22 g, 0.51 mmol) and NaHCO$_3$ (0.13 g, 1.53 mmol) in 10 mL MeOH was treated with Boc$_2$O (0.17 g, 0.76 mmol), and the resulting mixture was stirred at room temperature for 18 h. the solvent was removed in vacuo and 50 mL water was added, followed by extraction into CHCl$_3$. The combined extracts were washed with brine, dried over MgSO$_4$, filtered and concentrated to give the BOC protected product (0.19 g, 90%) as a white solid. MS (ES) m/z 419.3 [(M+H)$^+$ 90]; m/z 363.3 [(M+H-tBu)$^+$ 100].

Part C. Methanesulfonic acid 1-(4-{2-[(t-butoxycarbonyl-methylamino)-methyl]-imidazol-1-yl}-2-fluoro-phenyl)-2-oxo-piperidin-3-yl ester: To a solution of the compound of Ex. 8, Part B (0.19 g, 0.45 mmol) in 5 mL CH$_2$Cl$_2$ cooled to 0° C., was added Et$_3$N (69 mg, 0.68 mmol), followed by dropwise addition of methanesulfonyl chloride (57 mg, 0.5 mmol). After addition, the reaction mixture was stirred at 0° C. and slowly allowed to assume room temperature. Stirring at RT was continued for 7 h. Solvent was removed in vacuo and the residue dried under vacuum. Used crude in next step. MS (ES) m/z 497.3 [(M+H)+ 100].

Part D. {1-[4-(3-Azido-2-oxo-piperidin-1-yl)-3-fluorophenyl]-1H-imidazol-2-ylmethyl}-methyl-carbamic acid t-butyl ester: The product from Part C above was dissovled in 2 mL DMF, and NaN$_3$ (0.1 g, 1.61 mmol) was added. The mixture was stirred at room temperature for 18 h. Reaction was diluted with water, extracted with CHCl$_3$, the organic layer was washed with water and brine, then dried over MgSO$_4$, filtered and concentrated to give the azide (0.18, >90% over two steps). MS (ES) m/z 444.3 [(M+H)+ 100].

Part E. {1-[4-(3-Amino-2-oxo-piperidin-1-yl)-3-fluorophenyl]-1H-imidazol-2-ylmethyl}-methylcarbamic acid t-butyl ester: The compound of Ex. 8, Part D (0.18 g, 0.41 mmole) was dissolved in 5 mL MeOH and 20 mg of 5% Pd/C was added. The mixture was kept under 50 psi of H$_2$ on a Parr shaker for 18 h. Catalyst was removed by filtration through a pad of Celite and filtrate concentrated in vacuo to give the amine (0.11 g, 66%) which was used crude in the next step. MS (ES) m/z 418.3 [(M+H)+ 90].

Part F. (1-{4-[3-(6-Chlorothieno[2,3-b]pyridine-2-sulfonylamino)-2-oxo-piperidin-1-yl]-3-fluorophenyl}-1H-imidazol-2-ylmethyl)-methylcarbamic acid t-butyl ester: A mixture of the compound of Ex. 8, Part E (0.11 g, 0.264 mmole), 6-chlorothieno[2,3-b]pyridine-2-sulfonylchloride (85 mg, 0.316 mmole) and Et$_3$N (0.11 mL, 0.79 mmole) in 2 mL CH$_2$Cl$_2$ was stirred at room temperature for 2 h. Water was then added and the phases separated. Aqueous layer was reextracted with CH$_2$Cl$_2$ (3×) and combined extracts washed with brine and dried over MgSO$_4$, filtered and concentrated in vacuo to provide the product (45 mg, 26%). MS 649.3 (M+H)+.

Part G. 6-Chlorothieno[2,3-b]pyridine-2-sulfonic acid {1-[4-(2-methylaminomethylimidazol-1-yl)-2-fluorophenyl]-2-oxo-piperidin-3-yl}amide, trifluoroacetate salt: The compound of Ex. 8, Part F (21 mg, 0.032 mmole) was dissolved in 1 mL CH$_2$Cl$_2$ and treated with 2 mL TFA. This mixture was stirred at room temperature for 3 h, then stripped to dryness and purified by prep LC/MS to provide the title compound as its TFA salt (3.2 mg). $^1$H NMR (CD$_3$OD) δ 8.26 (m, 1H), 7.91 (s, 1H), 7.47 (m, 2H), 7.35 (m, 2H), 7.26 (m, 1H), 7.14 (m, 1H), 4.25 (m, 1H), 4.26 (s, 2H), 3.60 (m, 2H), 2.69 (s, 3H), 2.30 (m, 1H), 2.08 (m, 3H). MS (ES) m/z 549.2 [(M+H)+ 100].

Example 9

((6-Chlorothieno[2,3-b]pyridine-2-sulfonyl)-{1-[2-fluoro-4-(2-methylaminomethylimidazol-1-yl)phenyl]-2-oxo-piperidin-3-yl}amino)acetic acid methyl ester Part A. [[1-(4-{2-[(t-Butoxycarbonylmethylamino)-methyl]-imidazol-1-yl}-2-fluorophenyl)-2-oxo-piperidin-3-yl]-(6-chlorothieno[2,3-b]pyridine-2-sulfonyl)amino]acetic acid methyl ester: A mixture of the compound of Ex. 8, Part F (20 mg, 0.031 mmole), methyl bromoacetate (7.1 mg, 0.046 mmole) and K$_2$CO$_3$ (5.1 mg, 0.04 mmole) in 1 mL DMF was stirred at room temperature overnight. Water was added and mix extracted with chloroform. Organic phase was dried and concentrated. Used crude in next step. MS m/z 721.4 (M+H)+.

Part B. ((6-Chlorothieno[2,3-b]pyridine-2-sulfonyl)-{1-[2-fluoro-4-(2-methylaminomethylimidazol-1-yl)phenyl]-2-oxo-piperidin-3-yl}amino)acetic acid methyl ester: The compound of Part A above was deprotected as described for Ex. 8, Part G to give the title compound after prep LC/MS. $^1$H NMR (CD3OD) δ 8.28 (m, 1H), 7.96 (s, 1H), 7.48 (m, 2H), 7.35 (m, 2H), 7.25 (m, 1H), 7.14 (m, 1H), 4.80 (m, 1H), 4.21 (s, 2H), 4.19 (m, 1H), 3.80 (m, 1H), 3.72 (s, 3H), 3.70 (m, 1H), 3.55 (m, 1H), 2.68 (s, 3H), 2.40 (m, 1H), 2.19 (m, 3H).

Example 10

2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide Part A. ((6-Chloronaphthalene-2-sulfonyl)-{1-[2-fluoro-4-(2-oxo-2H-pyridin-1-yl)phenyl]-2-oxo-piperidin-3-yl}-amino)acetic acid t-butyl ester: The compound of Ex. 2 (37.7 mg, 0.07 mmole) was dissolved in 1 mL of DMF and treated with t-butyl bromoacetate (0.016 mL, 0.108 mmole) and K$_2$CO$_3$ (12 mg, 0.087 mmole). The whole was stirred at room temperature overnight. Reaction was diluted with water and extracted with CHCl$_3$. Extracts were combined, washed with brine, dried and evaporated.

Part B. ((6-Chloronaphthalene-2-sulfonyl)-{1-[2-fluoro-4-(2-oxo-2H-pyridin-1-yl)phenyl]-2-oxo-piperidin-3-yl}-amino)acetic acid: Crude product from Part A was dissolved in a mixture of 1 mL CH$_2$Cl$_2$ and 2 mL TFA and stirred at room temp. for 6 h. Stripped to dryness.

Part C. 2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide: A mixture of crude acid from Part B (39 mg, 0.067 mmole), N,N,N'-trimethylethylenediamine (0.009 mL, 0.07 mmole), triethylamine (0.028 mL, 0.2 mmole) and DMAP (8.1 mg, 0.067 mmole) in 1 mL DMF was treated with Castro's reagent (59.1 mg, 0.134 mmole) and the mixture stirred and heated in 50° C. oil bath overnight. Stripped to dryness and purified by prep LC/MS to provide the title compound as a TFA salt (17.2 mg, 33%). $^1$H NMR (CD3OD) δ 8.56 (s, 1H), 8.03 (m, 2H), 7.97 (s, 2H), 7.61 (m, 3H), 7.57 (m, 1H), 7.36 (m, 1H), 7.24 (m, 1H), 6.61 (m, 1H), 6.45 (m, 1H), 4.78 (m, 1H), 4.22 (m, 2H), 3.75 (m, 2H), 3.53 (m, 2H), 3.24 (m, 2H), 3.17 (s, 3H), 2.85 (s, 3H), 2.77 (s, 3H), 2.25 (m, 1H), 2.10 (M, 3H). MS (ES) m/z 668.2 [(M+H)+ 100].

Examples 11 and 12

(+)-2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide (Example 11) and (−)-2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide (Example 12)

The compound of Ex 10 was separated by chiral HPLC (Column: AD, MeOH:iPrOH:hexane 1:1:1) to provide the two enantiomers. Peak 1 (Ex. 11): $[\alpha]_D$ +20.0° (MeOH). $^1$H NMR (CD3OD) δ 8.55 (s, 1H), 8.01 (m, 2H), 7.96 (m, 2H), 7.59 (m, 3H), 7.46 (m, 1H), 4.26 (m, 1H), 4.15 (m, 1H), 3.67 (m, 2H), 3.59 (m, 2H), 3.13 (s, 3H), 3.03 (m, 2H), 2.65 (s, 6H), 2.25 (m, 1H), 2.05 (m, 3H). MS (ES) m/z 668.4 [(M+H)+ 100].

Peak 2 (Ex. 12): $[\alpha]_D$ −18.2° (MeOH). $^1$H NMR (CD3OD) δ 8.52 (s, 1H), 8.03 (m, 2H), 7.93 (m, 2H), 7.56 (m, 3H), 7.45 (m, 1H), 7.33 (m, 1H), 7.22 (m, 1H), 6.58 (m, 1H), 6.43 (m, 1H), 4.70 (m, 1H), 4.29 (m, 1H), 4.10 (m, 1H), 3.65 (m, 1H), 3.54 (m, 3H), 3.07 (s, 3H), 2.80 (m, 2H), 2.47 (s, 6H), 2.25 (m, 1H), 2.05 (m, 3H). MS (ES) m/z 668.4 [(M+H)⁺ 100].

Example 13

2-((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-N-methyl-acetamide Part A. ((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-acetic acid t-butyl ester: The compound of Ex. 3 was treated with t-butyl bromoacetate in the presence of $K_2CO_3$ using the procedure described for Ex. 10, Part A to provide the desired product in 91% yield. ¹H NMR (CDCl₃) δ 8.06 (m, 1H), 7.87 (s, 1H), 7.34 (m, 4H), 7.24 (m, 2), 6.68 (m, 1H), 6.26 (m, 1H), 4.70 (m, 1H), 4.14 (d, J=18.3 Hz, 1H), 3.65 (d, J=18.3 Hz, 1H), 3.60 (m, 1H), 2.60 (m, 1H), 2.17 (m, 3H), 1.50 (2, 9H). MS m/z 647.3 [(M+H)⁺, 45%], 591.2 [(M+H-tBu)⁺, 100%].

Part B. ((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-acetic acid: Deprotection of the t-butyl ester was carried out with TFA in $CH_2Cl_2$ as previously described to give the acid which was used without purification in the next step.

Part C. 2-((6-Chlorothieno[2,3-b]pyridine-2-sulfonyl)-{1-[2-fluoro-4-(2-oxo-2H-pyridin-1-yl)-phenyl]-2-oxo-piperidin-3-yl}amino)-N-methylacetamide: A mixture of the acid from Part B (30 mg, 0.051 mmole), methylamine hydrochloride (1.73 mg, 0.056 mmole), triethylamine (0.021 mL, 0.153 mmole), and DMAP (6.2 mg, 0.051 mmole) in DMF (1 mL) was treated with Castro's reagent (45 mg, 0.102 mmole) and the whole was stirred at 50° C. for 6 h. Reaction was worked up as described above and product purified by prep LC/MS to provide the title compound. ¹H NMR (CD₃OD) δ 8.33 (m, 1H), 8.01 (s, 1H), 7.62 (m, 2H), 7.53 (m, 2H), 7.30 (m, 1H), 7.29 (m, 1H), 6.62 (m, 1H), 6.47 (m, 1H), 4.70 (m, 1H), 4.08 (m, 1H), 3.75 (m, 2H), 3.60 (m, 1H), 2.64 (m, 3H), 2.38 (m, 2H), 2.15 (m, 2H). MS (ES) m/z 604.2 [(M+H)⁺ 100].

Example 14

2-((6-Chlorothieno[2,3-b]pyridine-2-sulfonyl)-{1-[2-fluoro-4-(2-oxo-2H-pyridin-1-yl)phenyl]-2-oxo-piperidin-3-yl}-amino)-N-(2-dimethylaminoethyl)-N-methylacetamide The compound of Ex. 13, Part B was coupled with N,N,N'-trimethylethylene diamine according to the procedure described for Ex. 8, Part C to provide the title compound after prep LC/MS. ¹H NMR (CD₃OD) δ 8.33 (m, 1H), 8.07 (s, 1H), 7.61 (m, 2H), 7.52 (m, 2H), 7.34 (m, 1H), 7.29 (m, 1H), 6.62 (m, 1H), 6.47 (m, 1H), 4.85 (m, 2H), 4.25 (m, 1H), 4.13 (m, 1H), 3.90 (m, 1H), 3.75 (m, 2H), 3.60 (m, 2H), 3.17 (s, 3H), 2.92 (s, 3H), 2.85 (s, 3H), 2.65 (m, 1H), 2.35 (m, 2H), 2.15 (m. 2H). MS (ES) m/z 675.3 [(M+H)⁺ 100].

Example 15

6-Chloronaphthalene-2-sulfonic acid {1-[4-(2-oxo-2H-pyridin-1-yl)-phenyl]-2-oxo-piperidin-3-yl}-amide Part A. 1-[4-(3-hydroxy-2-oxo-piperidin-1-yl)-phenyl]-1H-pyridin-2-one: A mixture of 1-(4-bromophenyl)-3-hydroxy-piperidin-2-one (2 g, 7.43 mmole), 2-hydroxypyridine (3.5 g, 37.17 mmole), $K_2CO_3$ (10.3 g, 74.35 mmole) and 1,10-phenanthroline (0.67 g, 3.71 mmole) in DMSO (25 mL) was degassed and then CuI (0.7 g, 3.71 mmole) was added. The wholes was heated in a 140° C. oil bath with stirring under $N_2$ for 6 h. Cooled to room temperature and worked up as previously described. Purification by prep HPLC provided the product (0.58 g, 28%). MS m/z 285.2 (M+H)⁺.

Part B. 1-[4-(3-amino-2-oxo-piperidin-1-yl)-phenyl]-1H-pyridin-2-one: The compound of Part A was converted to the corresponding mesylate, followed by displacement with sodium azide and reduction with tin chloride using the procedures of Ex. 17, Part C and Ex. 10, Part D respectively to provide the amine in 65% yield over the three steps. ¹H NMR (CDCl₃) δ 7.40 (m, 6H), 6.67 (m, 1H), 6.26 (m, 1H), 3.70 (m, 2H), 3.55 (m, 1H), 2.35 (m, 1H), 1.75 (m, 1H). MS m/z 284.1 (M+H)⁺.

Part C. 6-Chloronaphthalene-2-sulfonic acid {1-[4-(2-oxo-2H-pyridin-1-yl)-phenyl]-2-oxo-piperidin-3-yl}-amide: The amine was reacted with 6-chloronaphthylsulfonyl chloride according to the procedure of Ex. 1, Part H to provide the title compound after prep LC/MS. ¹H NMR (CDCl₃) δ 8.50 (s, 1H), 8.01 (m, 2H), 7.98 (m, 2H), 7.56 (m, 3H), 7.34 (m, 4H), 6.60 (m, 1H), 6.45 (m, 1H), 4.10 (m, 1H), 3.65 (m, 2H), 2.25 (m, 1H), 2.00 (m, 3H). MS (ES) m/z 507.9 [(M+H)⁺ 100].

Example 16

6-Chlorothieno[2,3-b]pyridine-2-sulfonic acid {1-[4-(2-oxo-2H-pyridin-1-yl)phenyl]-2-oxopiperidin-3-yl}amide The title compound was prepared from the compound of Ex. 15, Part B by treatment with 6-chlorothieno[2,3-b]pyridine-2-sulfonylchloride by the method described in Ex. 3. ¹H NMR (CDCl3) δ 8.30 (m, 1H), 0.97 (s, 1H), 7.58 (m, 2H), 7.78 (m, 1H), 7.38 (m, 4H), 6.60 (m, 1H), 6.45 (m, 1H), 4.20 (m, 1H), 3.70 (m, 2H), 2.30 (m, 1H), 2.05 (m, 3H). MS m/z 514.8 (M+H)⁺.

Example 17

2-((6-Chloronaphthalene-2-sulfonyl)-{1-[2-fluoro-4-(2-oxo-piperidin-1-yl)-phenyl]-2-oxo-piperidin-3-yl}amino)-N-(2-dimethylaminoethyl)-N-methylacetamide The title compound was prepared from the compound of Ex. 1 following the procedures outlined for the preparation of Ex. 10. ¹H NMR (CD₃OD) δ 8.59 (s, 1H), 8.05 (m, 2H), 7.95 (s, 2H), 7.30 (m, 1H), 7.15 (m, 2H), 4.75 (m, 1H), 4.19 (s, 2H), 3.80–3.40 (m, 6H), 3.25 (m, 2H), 3.17 (s, 3H), 2.81 (s, 3H), 2.71 (s, 3H), 2.45 (m, 2H), 2.10 (m, 1H), 2.05 (m, 3H), 1.93 (m, 4H). MS m/z 672.4 (M+H)⁺.

Example 18

N-{4-[3-(6-Chloro-naphthalene-2-sulfonylamino)-2-oxo-piperidin-1-yl]-phenyl}-2-dimethylamino-N-methyl-acetamide

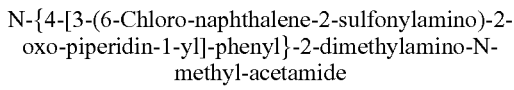

Part A: To a solution of 4-iodoaniline (10.0 g, 45.6 mmol) in dichloromethane (100 mL) were slowly added pyridine (7.4 mL, 91.3 mmol) and TFAA (7.1 mL, 50.22 mmol) at 0° C. The reaction was stirred at 0° C. for one hour. Water (50 mL) was added, and the organic layer was separated. The aqueous layer was further extracted with dichloromethane. The organic layers were combined, washed with water and brine, dried over magnesium sulfate, and filtered. Removal of the solvent gave the desired 2,2,2-trifluoro-N-(4-iodo-phenyl)-acetamide as a white solid.

Part B: The above-obtained amide was dissolved in acetone (80 mL), to which potassium carbonate (15.75 g, 114.1 mmol) and iodomethane (9.6 mL, 114.1 mmol) were added. The reaction was heated to reflux for 2 hours and cooled, and the resulting solid was filtered. The solvent was removed from the filtrate. The residue was dissolved in dichloromethane, washed with water and brine, and dried over sodium sulfate. After filtration and removal of solvent, the solid was further dried in vacuo to give the desired 2,2,2-trifluoro-N-(4-iodo-phenyl)-N-methyl-acetamide as a white solid. MS found: $(M+1)^+=330.05$.

Part C: The product obtained above was dissolved in methanol/water (2:1, 100 mL) and potassium carbonate (15.75 g, 114.1 mmol) was added. The mixture was stirred at rt for 6 hours. Dichloromethane (100 mL) was added, and the organic layer was separated, washed with water and brine, and dried over magnesium. Removal of the solvent gave the desired (4-iodo-phenyl)-methyl-amine as a dark colored, low-melting solid. MS found: $(M+1)^+=234.11$.

Part D: The product obtained above was dissolved in dichloromethane (100 mL), to which DIEA (12 mL) and chloroacetyl chloride (12 mL) were slowly added at 0° C. The reaction was stirred from 0° C. to rt for 4 hours, washed with 1.0 N HCl (2×) and brine, and dried over magnesium sulfate. After solvent removal, the crude product was purified by chromatography using ethyl acetate/hexane as eluent (2:8 to 4:6 ethyl acetate:hexane) to give the desired 2-chloro-N-(4-iodo-phenyl)-N-methyl-acetamide as a brown solid. MS found: $(M+1)^+=310.23$.

Part E: The product from part D (1.54 g, 4.98 mmol) was dissolved in THF/water (20/5 mL) and potassium carbonate (1.00 g, 7.25 mmol) followed by dimethyl amine (2.0 M in THF, 4.0 mL, 8.0 mmol) were added at rt. The mixture was stirred at rt over night. Most of the solvent was removed under reduced pressure. Dichloromethane was added to the residue. The solution was washed with saturated sodium bicarbonate and brine and dried over sodium sulfate, and the solvent was removed. The residue was further dried in vacuo to give the desired 2-dimethylamino-N-(4-iodo-phenyl)-N-methyl-acetamide as a light brown solid. MS found: $(M+1)^+=319.11$.

Part F: An oven-dried flask was charged with the product from part D (450 mg, 1.42 mmol), (2-oxo-piperidin-3-yl)-carbamic acid benzyl ester (333 mg, 1.34 mmol), CuI (27 mg, 0.14 mmol), and potassium phosphate (750 mg, 3.54 mmol). The flask was degassed and refilled with nitrogen. To the mixture was added anhydrous dioxane (10 mL) and trans-1,2-cyclohexanediamine (20 mg). The reaction was stirred at reflux under nitrogen for 10 hours and cooled, and the resulting solid filtered off. The filtrate was purified with HPLC using acetonitrile/water (5:95 to 95:5 gradient) as eluent to give the desired (1-{4-[(2-dimethylamino-acetyl)-methyl-amino]-phenyl}-2-oxo-piperidin-3-yl)-carbamic acid benzyl ester. MS found: $(M+1)^+=439.27$.

Part G: The above-obtained product (60 mg) was dissolved in acetonitrile (5.0 mL) and cooled to 0° C., to which iodotrimethylsilane (0.3 mL) was added. The reaction was stirred from 0° C. to rt for 4 hours. The solvent was removed under reduced pressure, and the desired product N-[4-(3-amino-2-oxo-piperidin-1-yl)-phenyl]-2-dimethylamino-N-methyl-acetamide was separated by HPLC using acetonitrile/water as eluent (5% to 95% gradient). MS found: $(M+1)^+=305.24$.

Part H: The amine from part G (50 mg) was dissolved in dichloromethane (3.0 mL) and 6-chloronaphthene-2-sulfonyl chloride (30 mg) and TEA (0.1 mL) were added. The reaction was stirred at rt for 4 hours. The solvent was removed under reduced pressure, and the residue was purified by HPLC using acetonitrile/water (30% to 95% gradient) as eluent to give the title compound as a white solid. MS found: $(M+1)^+=529.16/531.17$.

Example 19

{[(4-{3-[(6-Chloro-naphthalene-2-sulfonyl)-methoxycarbonylmethyl-amino]-2-oxo-piperidin-1-yl}-phenyl)-methyl-carbamoyl]-methyl}-methoxycarbonylmethyl-dimethyl-ammonium

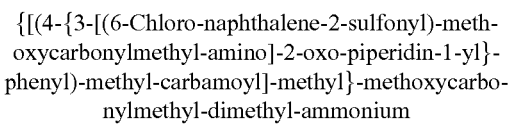

Following a procedure analogous to that described in Example 18, the title compound was obtained. MS found: $(M+1)^+=673.3$.

Example 20

N-{4-[3-(6-Chloro-naphthalene-2-sulfonylamino)-2-oxo-piperidin-1-yl]-phenyl}-N-methyl-2-pyrrolidin-1-yl-acetamide

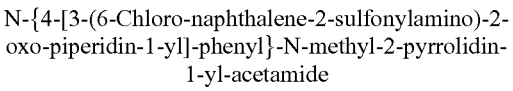

Following a procedure analogous to that described in Example 18, the title compound was obtained. MS found: $(M+1)^+=555.2$.

Example 21

N-{4-[3-(6-Chloro-naphthalene-2-sulfonylamino)-2-oxo-piperidin-1-yl]-phenyl}-2-dimethylamino-N-methylacetamide

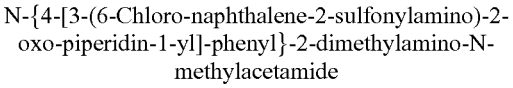

Following a procedure analogous to that described in Example 18, the title compound was obtained. MS found: $(M+1)^+=529.2$.

Example 22

N-{4-[3-(6-Chloro-thieno[2,3-b]pyridine-2-sulfonylamino)-2-oxo-piperidin-1-yl]-phenyl}-2-dimethylamino-N-methyl-acetamide

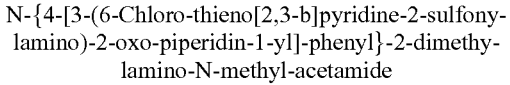

Following a procedure analogous to that described in Example 18, the title compound was obtained. MS found: $(M+1)^+=529.2$.

Example 23

((5-Chloro-thieno[3,2-b]pyridine-2-sulfonyl)-{2-oxo-1-[4-(2-oxo-2H-pyridin-1-yl)-phenyl]-piperidin-3-yl}-amino)-acetic acid methyl ester Following a procedure analogous to that described in Example 2, the title compound was obtained. MS found: $(M+)^+=587.1$.

Example 24

6-Chloro-naphthalene-2-sulfonic acid methyl-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=522.1$.

Example 25

6-Chloro-thieno[2,3-b]pyridine-2-sulfonic acid methyl-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=529.1$.

Example 26

6-Chloro-naphthalene-2-sulfonic acid ethyl-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=536.2$.

Example 27

6-Chloro-thieno[2,3-b]pyridine-2-sulfonic acid ethyl-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=543.1$.

Example 28

2-((6-Chloro-thieno[2,3-b]pyridine-2-sulfonyl)-{2-oxo-1-[4-(2-oxo-2H-pyridin-1-yl)-phenyl]-piperidin-3-yl}-amino)-acetamide Following a procedure analogous to that described in Examples 2 and 13, the title compound was obtained. MS found: $(M+1)^+=587.16$.

Example 29

6-Chloro-naphthalene-2-sulfonic acid cyanomethyl-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=605.2$.

Example 30

6-Chloro-naphthalene-2-sulfonic acid {2-oxo-1-[4-(2-oxo-2H-pyridin-1-yl)-phenyl]-piperidin-3-yl}-thiazol-4-ylmethyl-amide Following a procedure analogous to that described in Examples 2 and 13, the title compound was obtained. MS found: $(M+1)^+=547.2$.

Example 31

6-Chloro-naphthalene-2-sulfonic acid {2-oxo-1-[4-(2-oxo-2H-pyridin-1-yl)-phenyl]-piperidin-3-yl}-pyridin-3-ylmethyl-amide Following a procedure analogous to that described in Examples 2 and 13, the title compound was obtained. MS found: $(M+1)^+=599.3$.

Example 32

6-Chloro-naphthalene-2-sulfonic acid {2-oxo-1-[4-(2-oxo-2H-pyridin-1-yl)-phenyl]-piperidin-3-yl}-pyridin-2-ylmethyl-amide Following a procedure analogous to that described in Examples 2 and 13, the title compound was obtained. MS found: $(M+1)^+=599.3$.

Example 33

6-Chloro-naphthalene-2-sulfonic acid {2-oxo-1-[4-(2-oxo-2H-pyridin-1-yl)-phenyl]-piperidin-3-yl}-pyridin-4-ylmethyl-amide Following a procedure analogous to that described in Examples 2 and 13, the title compound was obtained. MS found: $(M+1)^+=599.3$.

Example 34

2-((6-Chloro-naphthalene-2-sulfonyl)-{2-oxo-1-[4-(2-oxo-2H-pyridin-1-yl)-phenyl]-piperidin-3-yl}-amino)-N-methyl-acetamide Following a procedure analogous to that described in Examples 2 and 13, the title compound was obtained. MS found: $(M+1)^+=579.2$.

Example 35

2-((6-Chloro-naphthalene-2-sulfonyl)-{2-oxo-1-[4-(2-oxo-2H-pyridin-1-yl)-phenyl]-piperidin-3-yl}-amino)-acetamide Following a procedure analogous to that described in Examples 2 and 13, the title compound was obtained. MS found: $(M+1)^+=565.1$.

Example 36

6-Chloro-naphthalene-2-sulfonic acid (2-methyl-thiazol-4-ylmethyl)-{2-oxo-1-[4-(2-oxo-2H-pyridin-1-yl)-phenyl]-piperidin-3-yl}-amide Following a procedure analogous to that described in Examples 2 and 13, the title compound was obtained. MS found: $(M+1)^+=619.1$.

Example 37

4-Methoxy-N-{2-oxo-1-[4-(2-oxo-2H-pyridin-1-yl)-phenyl]-piperidin-3-yl}-benzenesulfonamide Following a procedure analogous to that described in Example 2, the title compound was obtained. MS found: $(M+1)^+=454.3$.

Example 38

5-Chloro-thiophene-2-sulfonic acid {2-oxo-1-[4-(2-oxo-2H-pyridin-1-yl)-phenyl]-piperidin-3-yl}-amide Following a procedure analogous to that described in Example 2, the title compound was obtained. MS found: $(M+1)^+=464.1$.

Example 39

((5'-Chloro-[2,2']bithiophenyl-5-sulfonyl)-{2-oxo-1-[4-(2-oxo-2H-pyridin-1-yl)-phenyl]-piperidin-3-yl}-amino)-acetic acid methyl ester Following a procedure analogous to that described in Examples 2 and 13, the title compound was obtained. MS found: $(M+1)^+=618.1$.

Example 40

3-Chloro-N-{2-oxo-1-[4-(2-oxo-2H-pyridin-1-yl)-phenyl]-piperidin-3-yl}-benzenesulfonamide Following a procedure analogous to that described in Example 2, the title compound was obtained. MS found: $(M+1)^+=458.2$.

Example 41

((4-Methoxy-benzenesulfonyl)-{2-oxo-1-[4-(2-oxo-2H-pyridin-1-yl)-phenyl]-piperidin-3-yl}-amino)-acetic acid methyl ester Following a procedure analogous to that described in Examples 2 and 13, the title compound was obtained. MS found: $(M+1)^+=526.2$.

Example 42

((5-Chloro-thiophene-2-sulfonyl)-{2-oxo-1-[4-(2-oxo-2H-pyridin-1-yl)-phenyl]-piperidin-3-yl}-amino)-acetic acid methyl ester Following a procedure analogous to that described in Examples 2 and 13, the title compound was obtained. MS found: $(M+1)^+=536.1$.

Example 43

2-((4-Methoxy-benzenesulfonyl)-{2-oxo-1-[4-(2-oxo-2H-pyridin-1-yl)-phenyl]-piperidin-3-yl}-amino)-acetamide Following a procedure analogous to that described in Examples 2 and 13, the title compound was obtained. MS found: $(M+1)^+=511.2$.

Example 44

((6-Chloro-naphthalene-2-sulfonyl)-{2-oxo-1-[4-(2-oxo-2H-pyridin-1-yl)-phenyl]-piperidin-3-yl}-amino)-acetic acid tert-butyl ester Following a procedure analogous to that described in Examples 2 and 13, the title compound was obtained. MS found: $(M+Na)^+=644.1$.

Example 45

2-((5-Chloro-thiophene-2-sulfonyl)-{2-oxo-1-[4-(2-oxo-2H-pyridin-1-yl)-phenyl]-piperidin-3-yl}-amino)-acetamide Following a procedure analogous to that described in Examples 2 and 13, the title compound was obtained. MS found: $(M+1)^+=521.1$.

Example 46

((6-Chloro-naphthalene-2-sulfonyl)-{2-oxo-1-[4-(2-oxo-2H-pyridin-1-yl)-phenyl]-piperidin-3-yl}-amino)-acetic acid Following a procedure analogous to that described in Examples 2 and 13, the title compound was obtained. MS found: $(M+1)^+=566.1$.

Example 47

5-Chloro-thieno[3,2-b]pyridine-2-sulfonic acid {2-oxo-1-[4-(2-oxo-2H-pyridin-1-yl)-phenyl]-piperidin-3-yl}-amide Following a procedure analogous to that described in Example 2, the title compound was obtained. MS found: $(M+1)^+=515.3$.

Example 48

5'-Chloro-[2,2']bithiophenyl-5-sulfonic acid {2-oxo-1-[4-(2-oxo-2H-pyridin-1-yl)-phenyl]-piperidin-3-yl}-amide Following a procedure analogous to that described in Example 2, the title compound was obtained. MS found: $(M+1)^+=546.2$.

Example 49

2-((6-Chloro-naphthalene-2-sulfonyl)-{2-oxo-1-[4-(2-oxo-2H-pyridin-1-yl)-phenyl]-piperidin-3-yl}-amino)-N-(2-hydroxy-ethyl)-acetamide Following a procedure analogous to that described in Examples 2 and 13, the title compound was obtained. MS found: $(M+1)^+=609.3$.

Example 50

N-Carbamoylmethyl-2-((6-chloro-naphthalene-2-sulfonyl)-{2-oxo-1-[4-(2-oxo-2H-pyridin-1-yl)-phenyl]-piperidin-3-yl}-amino)-acetamide Following a procedure analogous to that described in Examples 2 and 13, the title compound was obtained. MS found: $(M+1)^+=622.3$.

Example 51

6-Chloro-naphthalene-2-sulfonic acid {2-oxo-1-[4-(2-oxo-piperidin-1-yl)-phenyl]-pyrrolidin-3-yl}-amide Following a procedure analogous to that described in Example 2, the title compound was obtained. MS found: $(M+)^+=498.2$.

Example 52

6-Chloro-naphthalene-2-sulfonic acid {2-oxo-1-[4-(2-oxo-2H-pyridin-1-yl)-phenyl]-pyrrolidin-3-yl}-amide Following a procedure analogous to that described in Example 2, the title compound was obtained. MS found: $(M+1)^+=494.1$.

Example 53

6-Chloro-thieno[2,3-b]pyridine-2-sulfonic acid {2-oxo-1-[4-(1-pyrrolidin-1-ylmethyl-cyclopropyl)-phenyl]-piperidin-3-yl}-amide Part A. To a mixture of (2-oxo-piperidin-3-yl)-carbamic acid benzyl ester (1.35 g, 5.44 mmol) and 1-(4-iodo-phenyl)-cyclopropanecarboxylic acid (1.56 g, 5.42 mmol, 1.0 eq) in DMSO (5 mL) was added $K_2CO_3$ (3.00 g, 21.73 mmol, 4.0 eq), CuI (0.52 g, 2.74 mmol, 0.5 eq), and 1,10-phenanthroline (0.50 g, 2.74 mmol, 0.5 eq) sequentially. The mixture was heated at 120° C. overnight under $N_2$. After cooling, EtOAc and $H_2O$ was added. The mixture was filtered. The filtrate was washed with 1N NaOH. The aqueous layer was acidified with conc. HCl, and extracted with EtOAc (3×). The organics were washed with brine, dried over $MgSO_4$, filtered, and concentrated to give crude 1-[4-(3-benzyloxycarbonyl-amino-2-oxo-piperidin-1-yl)-phenyl]-cyclopropanecarboxylic acid (0.69 g, slightly contaminated with disubstituted compound). LC/MS (ESI) 409.2 (M+H).

Part B. To a solution of the product from Part A (0.69 g, 1.69 mmol) in THF (10 mL) at 0° C. under $N_2$, was added $Et_3N$ (0.42 mL, 3.01 mmol, 1.8 eq), followed by dropwise addition of ClCOOEt (0.23 mL, 2.40 mmol, 1.5 eq). The mixture was stirred at 0° C. for 20 min. It was filtered and rinsed with THF (2 mL). To the filtrate was added MeOH (2 mL) and $NaBH_4$ (0.64 g, mmol, 5.9 eq) at 0° C. The mixture was stirred at 0° C. for 20 min, sat'd $Na_2SO_4$ was added. It was partitioned between EtOAc and $H_2O$. The organics were washed with brine, dried over $MgSO_4$, filtered, and concentrated. The residue was purified by silica gel chromatography ($CH_2Cl_2$, then $CH_2Cl_2$:EtOAc=1:1 then EtOAc) to give {1-[4-(1-hydroxymethyl-cyclopropyl)-phenyl]-2-oxo-piperidin-3-yl}-carbamic acid benzyl ester (0.29 g, yield 43.6%). LRMS (ESI) 395.4 (M+H).

Part C. The product of Part B (0.29 g, 0.74 mmol) and NaOAc (0.16 g, 1.95 mmol, 2.6 eq) were stirred in $CH_2Cl_2$ (5 mL). 4A Molecular sieves (one spatula tip) was added, followed by the addition of PCC (0.27 g, 1.25 mmol, 1.7 eq). The mixture was stirred at room temperature for 0.5 h. It was filtered through Celite. EtOAc was added and washed with $H_2O$ (2×), brine, dried over $MgSO_4$, filtered, and concentrated to dryness. The residue was stirred in $ClCH_2CH_2Cl$ (2 mL). Pyrolidine (0.2 mL), $NaBH(OAc)_3$ (0.5 g), and one drop of HOAc were added sequentially. The mixture was stirred at rt for 2 h. EtOAc was added. It was washed with brine, dried over $MgSO_4$, filtered, and concentrated. The residue was purified by FCC (EtOAc, then 5% MeOH in EtOAc) to give {2-Oxo-1-[4-(1-pyrrolidin-1-ylmethyl-cyclopropyl)-phenyl]-piperidin-3-yl}-carbamic acid benzyl ester (96 mg, yield 27%). LRMS (ESI) 478.4 (M+H).

Part D. The product from Part C (40.0 mg, 0.089 mmol) was dissolved in MeOH (1.5 mL), and 10% Pd/C (pipette tip) was added. The reaction vessel was purged with $H_2(g)$ (3×) and the reaction was allowed to stir for 1.5 h. The mixture was filtered and purified by prep LC/MS to obtained 3-amino-1-[4-(1-pyrrolidin-1-ylmethyl-cyclopropyl)-phenyl]-piperidin-2-one (15 mg, yield: 54%). LC/MS (ESI$^+$) 314.2 (M+H)$^+$, $t_R$=2.18 min (10–90% $CH_3CN/H_2O$ in a 6-min run)

Part E. To a $CH_2Cl_2$ (0.5 mL) solution of the product from Part D (7 mg, 0.022 mmol) was added 2M $Na_2CO_3$ (aq) (2 drops) and 6-Chloro-thieno[2,3-b]pyridine-2-sulfonyl chloride (11.7 mg, 0.043 mmol, 1.95 eq) sequentially. The resulting mixture was stirred at rt overnight. The residue was purified by prep LC/MS to give the titled compound (2.9 mg, 19%). LC/MS (ESI$^+$) 546.7 (M+H)$^+$, $t_R$=4.07 min (5–98% $CH_3CN/H_2O$ in a 10-min run). $^1$H NMR ($CD_3CO$, 300 MHz) δ 8.25 (d, J=8 Hz, 1H), 7.91 (s, 1H), 7.45 (m, 3H), 7.18 (d, J=8 Hz, 2H), 4.19 (m, 2H), 3.61 (m, 2H), 2.95 (m, 4H), 2.15 (m, 4H), 1.85 (m, 2H) 1.30 (m, 2H), 1.15 (m, 4H) ppm.

Example 54

6-Chloro-naphthalene-2-sulfonic acid {2-oxo-1-[4-(1-pyrrolidin-1-ylmethyl-cyclopropyl)-phenyl]-piperidin-3-yl}-amide Following a procedure analogous to that described in Example 53, the title compound was obtained. MS found: $(M+1)^+=538.7$. $^1$H NMR ($CD_3CO$, 300 MHz) δ 8.55 (s, 1H), 8.10 (m, 4H), 7.61 (d, J=8 Hz, 1H), 7.43 (d, J=6 Hz, 2H), 7.18 (d, J=6 Hz, 2H), 6.65 (bs, 1H), 3.85 (m, 1H), 3.65 (m, 1H), 3.50 (bs, 4H), 2.85 (bs, 6H), 1.83 (bs, 2H), 1.15 (bs, 2H), 0.85 (bs, 2H) ppm.

Example 55

2-((6-Chloro-naphthalene-2-sulfonyl)-{2-oxo-1-[4-(2-oxo-2H-pyridin-1-yl)-phenyl]-piperidin-3-yl}-amino)-acetic acid methyl ester The compound of Example 2 was treated with methyl bromoacetate in the presence of potassium carbonate using the procedure described for the preparation of compound 9, Part A. Purification by flash chromatography provided the title compound. MS(ESI$^+$) (M+H)$^+$. $^1$HNMR (CDCl$_3$) δ 8.48 (s, 1H); 7.85 (m, 4H); 7.53 (m, 2H); 7.37 (m, 3H); 7.27 (m, 2H); 6.85 (m, 1H); 6.45 (m, 1H); 4.60 (m, 1H); 4.30 (m, 1H); 3.80 (m, 1H); 3.74 (m, 3H); 3.60 (m, 1H); 3.40 (m, 1H); 2.55

(m, 1H); 2.15 (m, 3H) ppm. MS m/z 580.0 (M+H)$^+$. HRMS calcd for $C_{29}H_{27}N_3O_6SCl$: 580.1309. Found: 580.1310.

Example 56

2-((6-Chlorothieno[2,3-b]pyridine-2-sulfonyl)-{2-oxo-1-[4-(2-oxo-2H-pyridin-1-yl)-phenyl]-piperidin-3-yl}-amino)-acetic acid methyl ester The compound of Example 3 was treated with methyl bromoacetate in the presence of potassium carbonate using the procedure described for the preparation of compound 9, Part A. Purification by flash chromatography provided the title compound. MS(ESI$^+$) (M+H)$^+$. $^1$HNMR (CDCl$_3$) δ 8.08 (m, 1H); 7.89 (s, 1H); 7.48 (m, 1H); 7.39 (m, 2H); 7.31 (m, 4H); 6.78 (m, 1H); 6.36 (m, 1H); 4.72 (m, 1H); 4.27 (m, aH); 3.83 (m, 1H); 3.78 (s, 3H); 3.74 (m, 1H); 3.66 (m, 1H); 2.60 (m, 1H); 2.16 (m, 3H). MS m/z 586.9 (M+H)$^+$. HRMS calcd for $C_{26}H_{24}N_4O_6S_2Cl$: 587.0826. Found: 587.0813.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Compounds tested in the above assay are considered to be active if they exhibit a $K_i$ of ≦10 μM. Preferred compounds of the present invention have $K_i$'s of ≦1 μM. More preferred compounds of the present invention have $K_i$'s of ≦0.1 μM. Even more preferred compounds of the present invention have $K_i$'s of ≦0.01 μM. Still more preferred compounds of the present invention have $K_i$'s of ≦0.001 μM. Using the methodology described above, a number of compounds of the present invention were found to exhibit $K_i$'s of ≦10 μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID$_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect., Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of a compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of a compound of the present invention and about 50 to 150 milligrams of the anti-platelet agent, preferably about 0.1 to 1 milligrams of a compound of the present invention and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when a compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Numerous modifications and variations of the present invention are possible in light of the above teachings. It is therefore to be understood that within the scope of the appended claims, the invention may be practiced otherwise that as specifically described herein.

What is claimed is:

1. A compound of formula Ib:

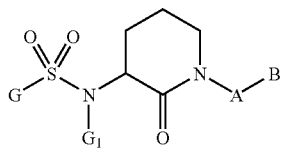

Ib or a stereoisomer or pharmaceutically acceptable salt thereof, wherein;

the central lactam ring is substituted with 0–2 $R^{1a}$;

G is a group of formula IIa or IIb:

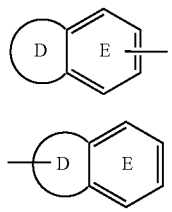

IIa

IIb ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazmyl, and pyridazinyl, and is substituted with 1–3 R;

alternatively, ring D is absent, and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent, ring E is selected from phenyl, phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatorns selected from the group consisting of N, O, and $S(O)_p$, wherein the 5–6 membered heterocycle is substituted with 0–2 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$;

alternatively, when 2 R groups are attached to adjacent atoms, they combine to form methylenedioxy or ethylenedioxy;

$G_1$ is selected from H, $(CR^3R^{3a})_{1-2}C(O)R^2$, $(CR^3R^{3a})_{1-2}NR^2R^{2a}$, $(CR^3R^{3a})_{1-2}OR^2$, $(CR^3R^{3a})_{1-2}S(O)_pR^2$, $(CR^3R^{3a})_{1-2}NR^2C(O)R^2$, $(CR^3R^{3a})_{1-2}NR^2C(O)NR^2R^{2a}$, $(CR^3R^{3a})_{1-2}NR^2C(O)OR^2$, $(CR^3R^{3a})_{1-2}S(O)_2NR^2R^{2a}$, $(CR^3R^{3a})_{1-2}NR^2S(O)_2NR^2R^{2a}$, $(CR^3R^{3a})_{1-2}OC(O)R^2$, $(CR^3R^{3a})_{1-2}C(O)OR^2$, $(CR^3R^{3a})_{1-2}C(O)NR^2R^{2a}$, $(CR^3R^{3a})_{1-2}C(O)NR^2(CR^3R^{3a})(CR^3R^{3a})_{1-2}OR^2$, $(CR^3R^{3a})_{1-2}C(O)NR^2(CR^3R^{3a})(CR^3R^{3a})_{1-2}NR^2R^{2a}$, $(CR^3R^{3a})C(O)NR^2(CR^3R^{3a})_{1-2}C(O)NR^2R^{2a}$, $(CR^3R^{3a})C(O)NR^2(CR^3R^{3a})_{1-2}C(O)OR^2$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $(CR^3R^{3a})_{0-4}$–$C_{3-10}$ carbocycle substituted with 0–3 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–3 $R^{1a}$;

A is selected from:

$C_{3-10}$ carbocycle substituted with 0–2 $R^4$, and

5–12 membered heterocycle consisting of: carbon atoms and 1–4 heteroatoms selected from the group consisting of N, O, and $S(O)_p$ and substituted with 0–2 $R^4$;

B is selected from $X—Y—R^{4a}$, $N(B^1)C(O)C(R^3R^{3g})_{1-4}NB^2B^3$, and

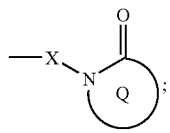

provided that the central lactam ring and B are attached to different atoms on A and that the A-X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

alternatively, $NB^2B^3$ is a 3–8 membered heterocycle consisting of: the shown N, carbon atoms, and 0–3 additional heteroatoms selected from the group consisting of N, O, and $S(O)_p$ and substituted with 0–2 $R^5$;

ring Q is a 4–7 membered lactam consisting of, in addition to the amide group shown, carbon atoms and 0–2 heteroatoms selected from $NR^{4c}$, O, S, S(O), and $S(O)_2$, wherein:
  0–2 double bonds are present within the ring and the ring is substituted with 0–2 $R^{4a}$;

alternatively, ring Q is a 4–7 membered lactam to which another ring is fused, wherein:
  the lactam consists of, in addition to the shown amide group, carbon atoms and 0–2 heteroatoms selected from $NR^{4c}$, O, S, S(O), and $S(O)_2$ and 0–2 double bonds are present within the ring;
  the fusion ring is phenyl or a 5–6 membered heteroaromatic consisting of carbon atoms and 0–2 $NR^{4c}$, O, S, S(O), and $S(O)_2$;
  ring Q, which includes the lactam ring and the fusion ring, is substituted with 0–3 $R^{4a}$;

X is absent or is selected from —$(CR^2R^{2a})_{1-4}$—, —$CR^2(CR^2R^{2b})(CH_2)_t$—, —C(O)—, —C(=$NR^{1b}$)—, —$CR^2(NR^{1b}R^2)$—, —$CR^2(OR^2)$—, —$CR^2(SR^2)$—, —$C(O)CR^2R^{2a}$—, —$CR^2R^{2a}C(O)$—, —S(O)—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$S(O)_2NR^2CR^2R^{2a}$—, —$CR^2R^{2a}S(O)_2NR^2$—, —$NR^2S(O)_2$—, —$CR^2R^{2a}NR^2S(O)_2$—, —$NR^2S(O)_2CR^2R^{2a}$—, —$NR^2C(O)$—, —$C(O)NR^2$—, —$NR^2C(O)CR^2R^{2a}$—, —$C(O)NR^2CR^2R^{2a}$—, —$CR^2R^{2a}NR^2C(O)$—, —$CR^2R^{2a}C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

Y is selected from $CY^1Y^2R^{4a}$, a $C_{3-10}$ carbocycle, and 3–10 membered heterocycle, wherein the carobocycle or heterocycle consists of carbon atoms and 0–4 heteroatoms selected from N, O, and $S(O)_p$, the carbocycle or heterocycle further comprises 0–4 double bonds and 0–2 carbonyl groups, and the carbocycle or heterocycle is substituted with 0–2 $R^4$;

$Y^1$ and $Y^2$ are independently $C_{1-4}$ alkyl substituted with 0–2 $R^4$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—C(=$NR^{1b}$)$NR^3R^{1b}$, $NR^3(CR^3R^{3a})_rR^{1c}$, $O(CR^3R^{3a})_rR^{1c}$, $(CR^3R^{3a})_rSCR^3R^{3a}R^{1c}$, $(CR^3R^{3a})_rNR^3(CR^3R^{3a})_rR^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $(CR^3R^{3a})_rS(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2R^2C(O)NR^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0–2 $R^{4b}$ and 5–10 membered heterocycle consisting of carbon atoms and from 1–4 heteroatoms selected from the group consisting of N, O, and $S(O)_p$ and substituted with 0–2 $R^{4b}$, provided that $R^{1d}$ forms other than an N—S bond;

$R^2$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5–10 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or $C(O)$—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_rOR^2$, $(CR^3R^{3a})_rF$, $(CR^3R^{3a})_rCl$, $(CR^3R^{3a})_rBr$, $(CR^3R^{3a})_rI$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2—C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, —$(CR^3R^{3g})_r$—$C_{5-10}$ membered carbocycle substituted with 0–3 $R^{4c}$, —$(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_rCN$, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$C(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$OC(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2NR^{2d}R^{2d}$, $(CR^3R^{3g})_r$—$C(O)NR^{2d}SO_2R^{2d}$, $(CR^3R^{3g})_r$—$NR^{2d}SO_2R^{2d}$, and $(CR^3R^3g)_r$—$S(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r$—$C(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_pC_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-6}$ alkenyl, $C_{2-6}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR_3R^{3a})_rC(O)NR^2SO_2—C_{1-4}$ alkyl, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

R$^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$—C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl C$_{1-4}$ alkyl-C(O)—;

R$^8$, at each occurrence, is selected from H, C$_{1-6}$ alkyl, and (CH$_2$)$_n$-phenyl;

alternatively, R$^7$ and R$^8$, when attached to the same nitrogen, combine to form a 5–10 membered heterocyclic ring consisting of carbon atoms and 0–2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
r1, at each occurrence, is selected from 1, 2, 3, 4, 5, and 6; and,
t, at each occurrence, is selected from 0, 1, 2, and 3.

2. A compound according to claim 1, wherein:
the central lactam ring is substituted with 0–1 R$^{1a}$;
G is a group of formula IIa or IIb:

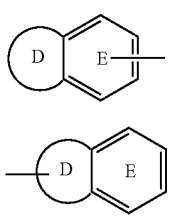

ring D, including the two atoms of ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and S(O)$_p$, wherein the 5 membered heterocycle is substituted with 0–1 carbonyls and 1–2 R and has 0–3 ring double bonds;

R is selected from H, C$_{1-4}$ alkyl, F, Cl, OH, OCH$_3$, OCH$_2$CH$_3$, OCH(CH$_3$)$_2$, CN, C(=NH)NH$_2$, NH$_2$, NH(C$_{1-3}$ alkyl), N(C$_{1-3}$ alkyl)$_2$, C(=NH)NH$_2$, CH$_2$NH$_2$, CH$_2$NH(C$_{1-3}$ alkyl), CH$_2$N(C$_{1-3}$ alkyl)$_2$, (CR$^8$R$^9$)$_r$NR$^7$R$^8$, C(O)NR$^7$R$^8$, CH$_2$C(O)NR$^7$R$^8$, S(O)$_p$NR$^7$R$^8$, CH$_2$S(O)$_p$NR$^7$R$^8$, and OCF$_3$;

alternatively, when 2 R groups are attached to adjacent atoms, they combine to form methylenedioxy or ethylenedioxy;

G$_1$ is selected from H, (CR$^3$R$^{3a}$)C(O)R$^2$, (CR$^3$R$^{3a}$)NR$^2$R$^{2a}$, (CR$^3$R$^{3a}$)OR$^2$, (CR$^3$R$^{3a}$)S(O)$_p$R$^2$, (CR$^3$R$^{3a}$)NR$^2$C(O)R$^2$, (CR$^3$R$^{3a}$)NR$^2$C(O)NR$^2$R$^{2a}$, (CR$^3$R$^{3a}$)NR$^2$C(O)OR$^2$, (CR$^3$R$^{3a}$)S(O)$_2$NR$^2$R$^{2a}$, (CR$^3$R$^{3a}$)NR$^2$S(O)$_2$NR$^2$R$^{2a}$, (CR$^3$R$^{3a}$)OC(O)R$^2$, (CR$^3$R$^{3a}$)C(O)OR$^2$, (CR$^3$R$^{3a}$)C(O)NR$^2$R$^{2a}$, (CR$^3$R$^{3a}$)C(O)NR$^2$(CR$^3$R$^{3a}$)(CR$^3$R$^{3a}$)OR$^2$, (CR$^3$R$^{3a}$)C(O)NR$^2$(CR$^3$R$^{3a}$)(CR$^3$R$^{3a}$)(CR$^3$R$^{3a}$)OR$^2$, (CR$^3$R$^{3a}$)C(O)NR$^2$(CR$^3$R$^{3a}$)(CR$^3$R$^{3a}$)NR$^2$R$^{2a}$, (CR$^3$R$^{3a}$)C(O)NR$^2$(CR$^3$R$^{3a}$)(CR$^3$R$^{3a}$)NR$^2$R$^{2a}$, (CR$^3$R$^{3a}$)C(O)NR$^2$(CR$^3$R$^{3a}$)C(O)NR$^2$R$^{2a}$, (CR$^3$R$^{3a}$)C(O)NR$^2$(CR$^3$R$^{3a}$)C(O)NR$^2$R$^{2a}$, (CR$^3$R$^{3a}$)C(O)NR$^2$(CR$^3$R$^{3a}$)C(O)OR$^2$, (CR$^3$R$^{3a}$)C(O)NR$^2$(CR$^3$R$^{3a}$)(CR$^3$R$^{3a}$)C(O)OR$^2$, C$_{1-6}$ alkyl substituted with 0–1 R$^{1a}$, C$_{2-6}$ alkenyl substituted with 0–1 R$^{1a}$, C$_{2-6}$ alkynyl substituted with 0–1 R$^{1a}$, (CR$^3$R$^{3a}$)$_{0-4}$—C$_{3-10}$ carbocycle substituted with 0–1 R$^{1a}$, and (CR$^3$R$^{3a}$)$_{0-4}$-5–12 membered heterocycle consisting of: carbon atoms and 1–4 heteroatoms selected from the group consisting of N, O, and S(O)$_p$ and substituted with 0–1 R$^{1a}$;

A is selected from:
C$_{5-10}$ carbocycle substituted with 0–2 R$^4$, and
5–10 membered heterocycle consisting of: carbon atoms and 1–4 heteroatoms selected from the group consisting of N, O, and S(O)$_p$ and substituted with 0–2 R$^4$;
provided that A is other than a dihydro-benzopyran;

B is selected from N(B$^1$)C(O)C(R$^3$R$^{3g}$)NB$^2$B$^3$, N(B$^1$)C(O)C(R$^3$R$^{3g}$)C(R$^3$R$^{3g}$)NB$^2$B$^3$,

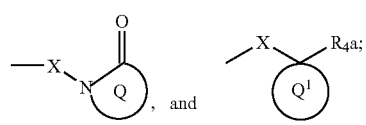 and provided that the central lactam ring and B are attached to different atoms on A and that the A-X—N moiety forms other than a N—N—N group;

B$^1$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —(CH$_2$)$_{0-1}$—C$_{3-7}$ carbocycle substituted with 0–2 R$^{4b}$, and —(CH$_2$)$_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

ring Q is a 4–7 membered lactam consisting of, in addition to the amide group shown, carbon atoms and 0–2 heteroatoms selected from $NR^{4c}$, O, S, S(O), and $S(O)_2$, wherein:
  0–2 double bonds are present within the ring and the ring is substituted with 0–2 $R^{4a}$;

alternatively, ring Q is a 4–7 membered lactam to which another ring is fused, wherein:
  the lactam consists of, in addition to the shown amide group, carbon atoms and 0–2 heteroatoms selected from $NR^{4c}$, O, S, S(O), and $S(O)_2$ and 0–1 double bonds are present within the ring;
  the fusion ring is phenyl or a 5–6 membered heteroaromatic consisting of carbon atoms and 0–2 $NR^{4c}$, O, and S;
  ring Q, which includes the lactam ring and the fusion ring, is substituted with 0–3 $R^{4a}$;

ring $Q^1$ is selected from $CY^1Y^2$, a $C_{3-7}$ monocyclic carbocycle, and a 3–7 membered monocyclic heterocycle, wherein the carbocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

X is absent or is selected from —$(CR^2R^{2a})_{1-4}$—, —C(O)—, —$C(O)CR^2R^{2a}$—, —$CR^2R^{2a}C(O)$, —$S(O)_2$—, —$S(O)_2CR^2R^{2a}$—, —$CR^2R^{2a}S(O)_2$—, —$S(O)_2NR^2$—, —$NR^2S(O)_2$—, —$NR^2C(O)$—, —$C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

$Y^1$ and $Y^2$ are independently $C_{1-3}$ alkyl substituted with 0–1 $R^4$;

$R^{1a}$, at each occurrence, is selected from H, —$(CR^3CR^{3a})_r$—$R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—$C(=NR^{1b})NR^3R^{1b}$, $NR^3(CR^3R^{3a})_rR^{1c}$, $O(CR^3R^{3a})_rR^{1c}$, —$(CR^3R^{3a})_r$—$SCR^3R^{3a}R^{1c}$, $(CR^3R^{3a})_rNR^3(CR^3R^{3a})_rR^{1b}$, $(CR^3R^{3a})_rC(O)NR^2$ $(CR^3R^{3a})_rR^{1b}$, $CO_2(CR^3R^{3a})_rR^{1b}$, $O(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $(CR^3R^{3a})_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, a $C_{5-6}$ carbocyclic-$CH_2$ group substituted with 0–2 $R^{4b}$, a 5–6 membered heterocycle consisting of: carbon atoms and 1–4 heteroatoms selected from the group consisting of N, O, and $S(O)_p$ and substituted with 0–2 $R^{4b}$, and a 5–6 membered heterocycle-$CH_2$ group consisting of: carbon atoms and 1–4 heteroatoms selected from the group consisting of N, O, and $S(O)_p$ and substituted with 0–2 $R^{4b}$ $R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two R$^{2d}$'s are attached to the same nitrogen atom, then R$^{2d}$ and R$^{2d}$, together with the nitrogen atom to which they are attached, combine to form a 5 or 6 membered ring saturated, partially saturated or unsaturated ring substituted with 0–2 R$^{4b}$ and consisting of: 0–1 additional heteroatoms selected from the group consisting of N, O, and S(O)$_p$;

R$^{2e}$, at each occurrence, is selected from H, R$^{4c}$, C$_{1-4}$ alkyl substituted with 0–2 R$^{4c}$, —(CR$^3$R$^{3a}$)$_r$—C$_{3-6}$ carbocycle substituted with 0–2 R$^{4c}$, and —(CR$^3$R$^{3a}$)$_r$-5–6 membered heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms and the nitrogen atom to which R$^3$ and R$^{3a}$ are attached;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, S(O)$_p$R$^5$, CF$_3$, CF$_2$CF$_3$, 5–6 membered carbocycle substituted with 0–1 R$^5$, and a 5–6 membered heterocycle consisting of: carbon atoms and 1–4 heteroatoms selected from the group consisting of N, O, and S(O)$_p$ and substituted with 0–1 R$^5$;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, NR$^2$SO$_2$NR$^2$R$^{2a}$, S(O)$_p$R$^{5a}$, NR$^2$SO$_2$—C$_{1-4}$ alkyl, NR$^2$SO$_2$R$^5$, CF$_3$, CF$_2$CF$_3$, 5–6 membered carbocycle substituted with 0–1 R$^5$, and a 5–6 membered heterocycle consisting of: carbon atoms and 1–4 heteroatoms selected from the group consisting of N, O, and S(O)$_p$, and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$—CF$_3$;

R$^{4c}$, at each occurrence, is selected from =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-3}$ alkenyl, C$_{2-3}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^3$a)$_r$C$_{3-10}$ carbocycle substituted with 0–2 R$^{4b}$, and (CR$^3$R$^{3a}$)$_r$5–10 membered heterocycle consisting of carbon atoms and from 1–4 heteroatoms selected from the group consisting of N, O, and S(O)$_p$ and substituted with 0–2 R$^{4b}$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$_3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^{5a}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, C(CH$_3$)$_3$, OR$^3$, CH$_2$OR$^3$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, CF$_3$, CF$_2$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond;

R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

3. A compound according to claim 2, wherein the compound is of formula Ib:

G is selected from the group:

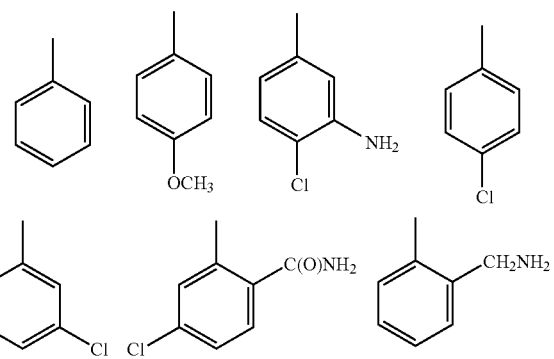

-continued
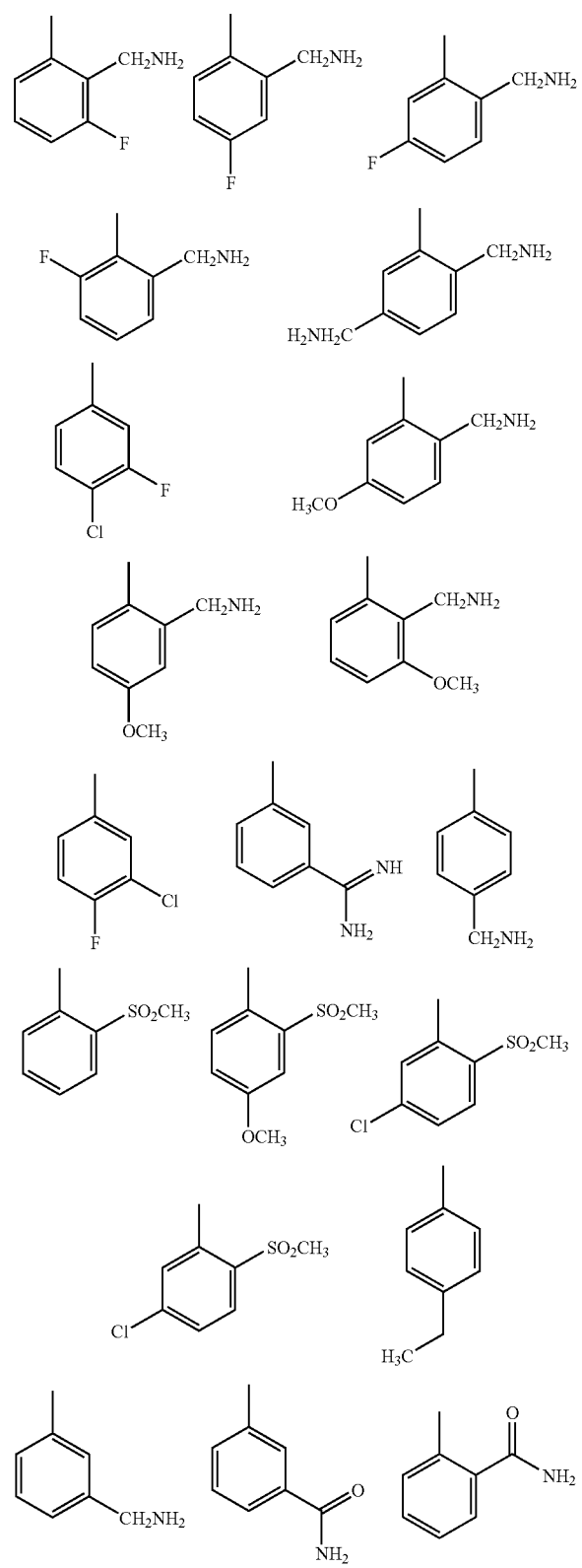
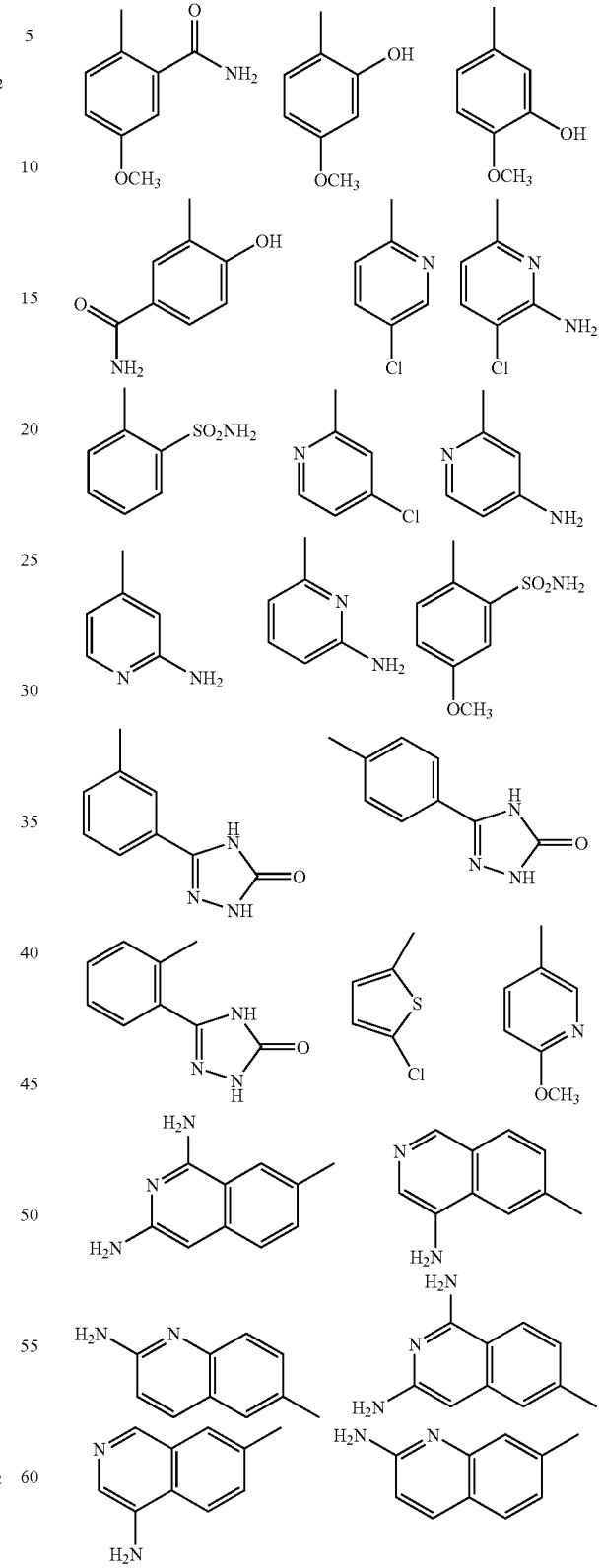

-continued
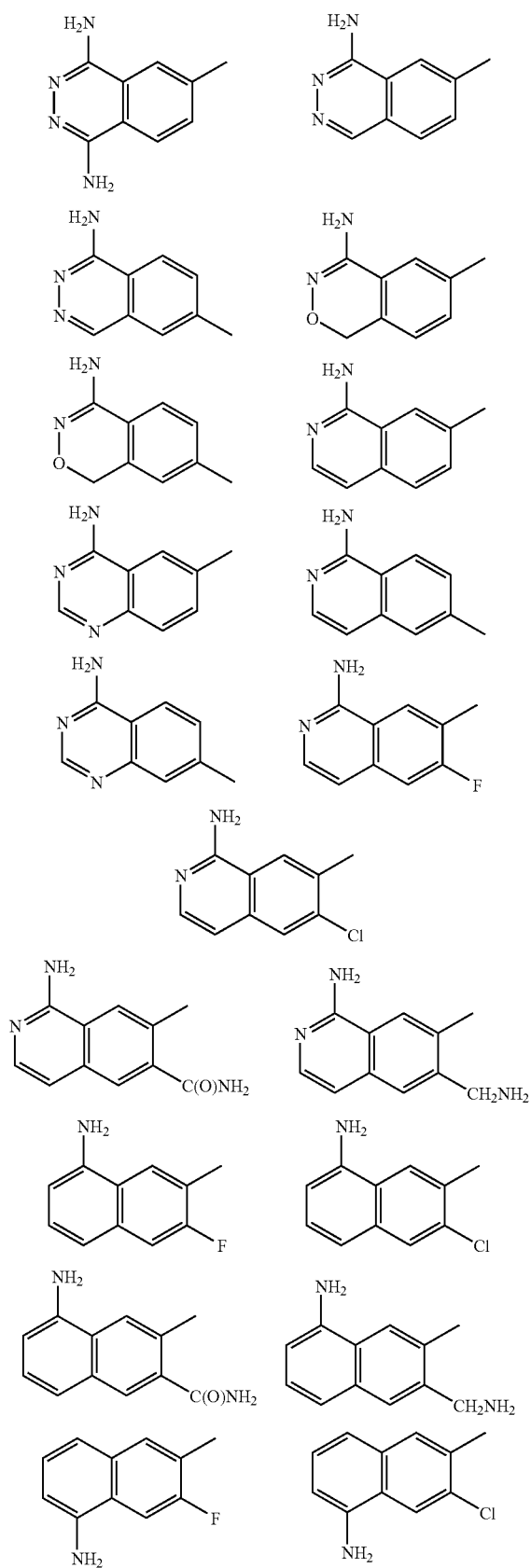
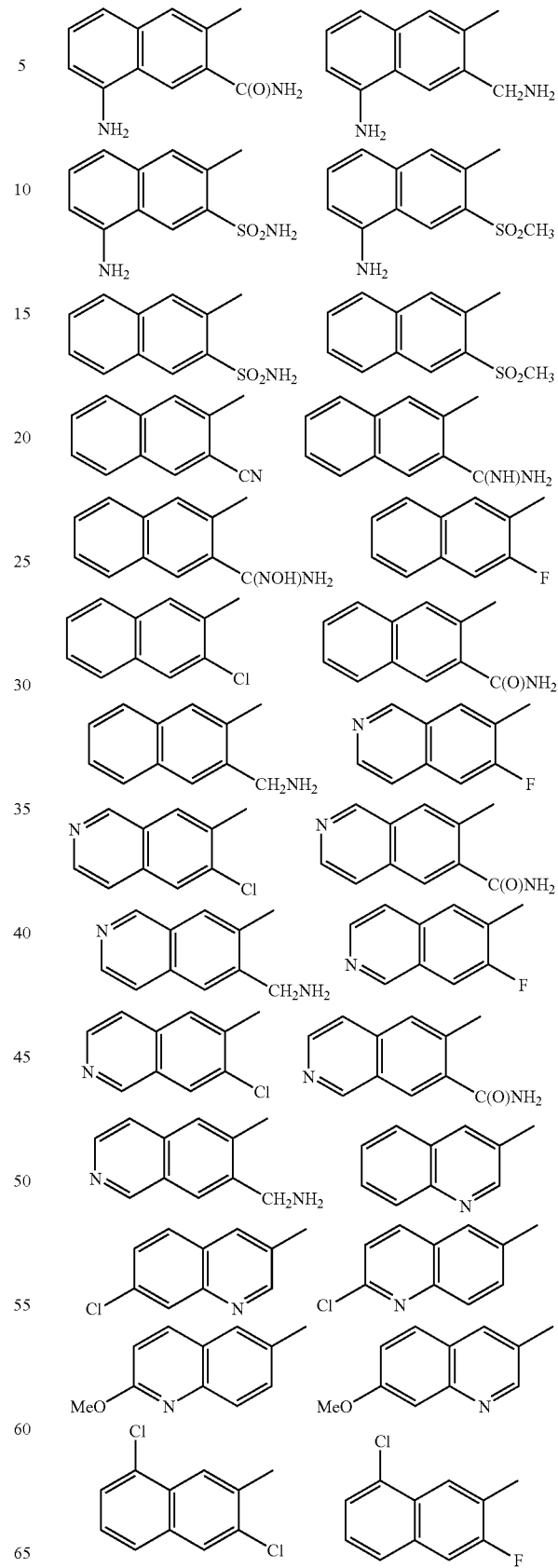

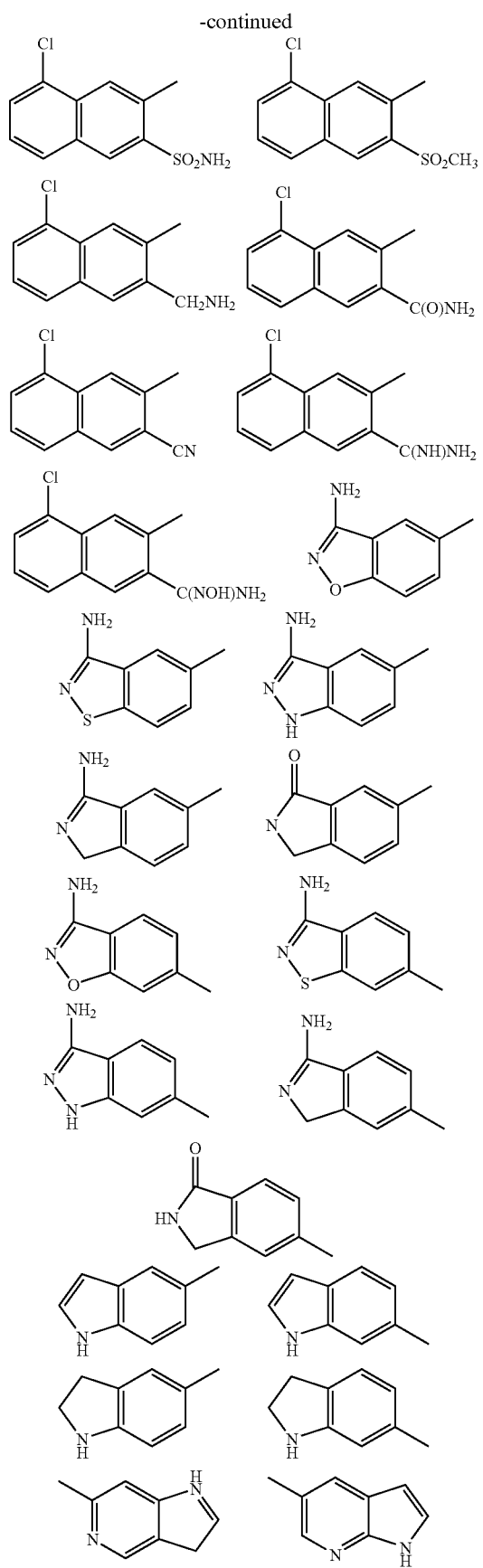
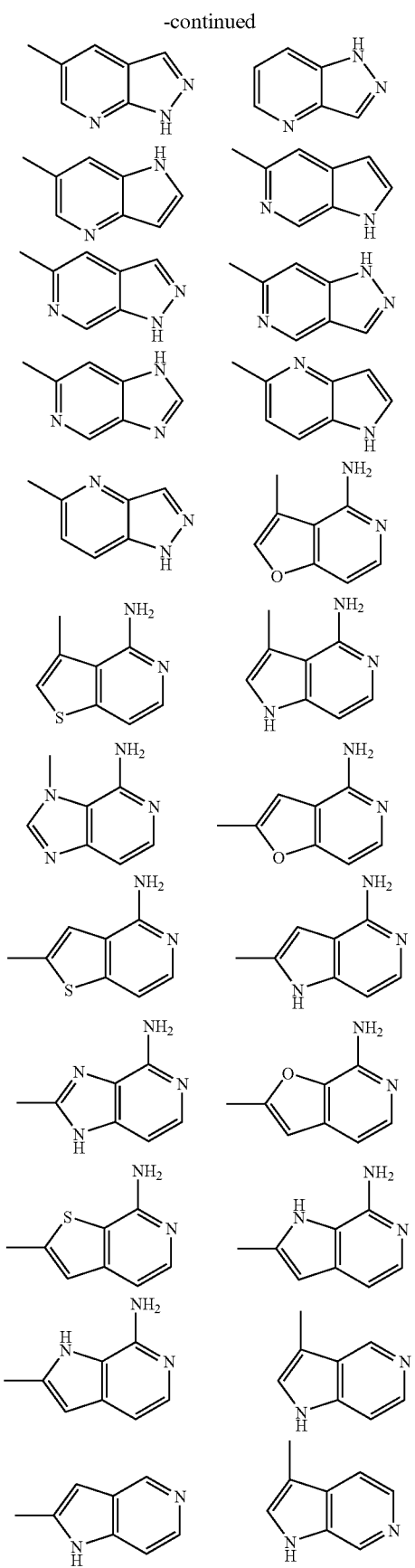

-continued
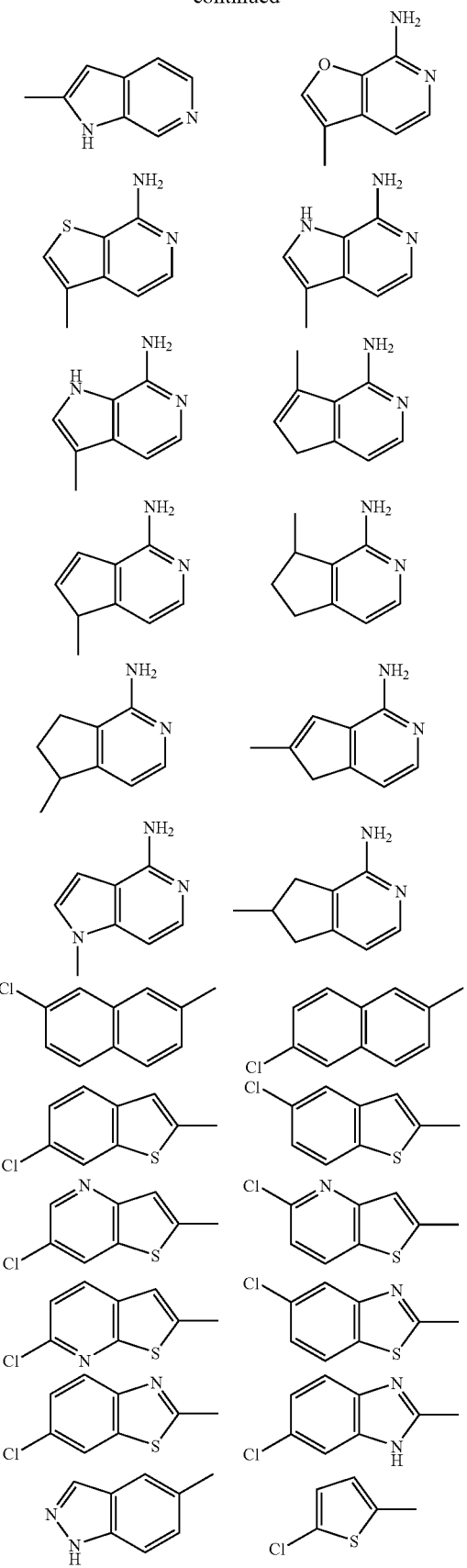
-continued
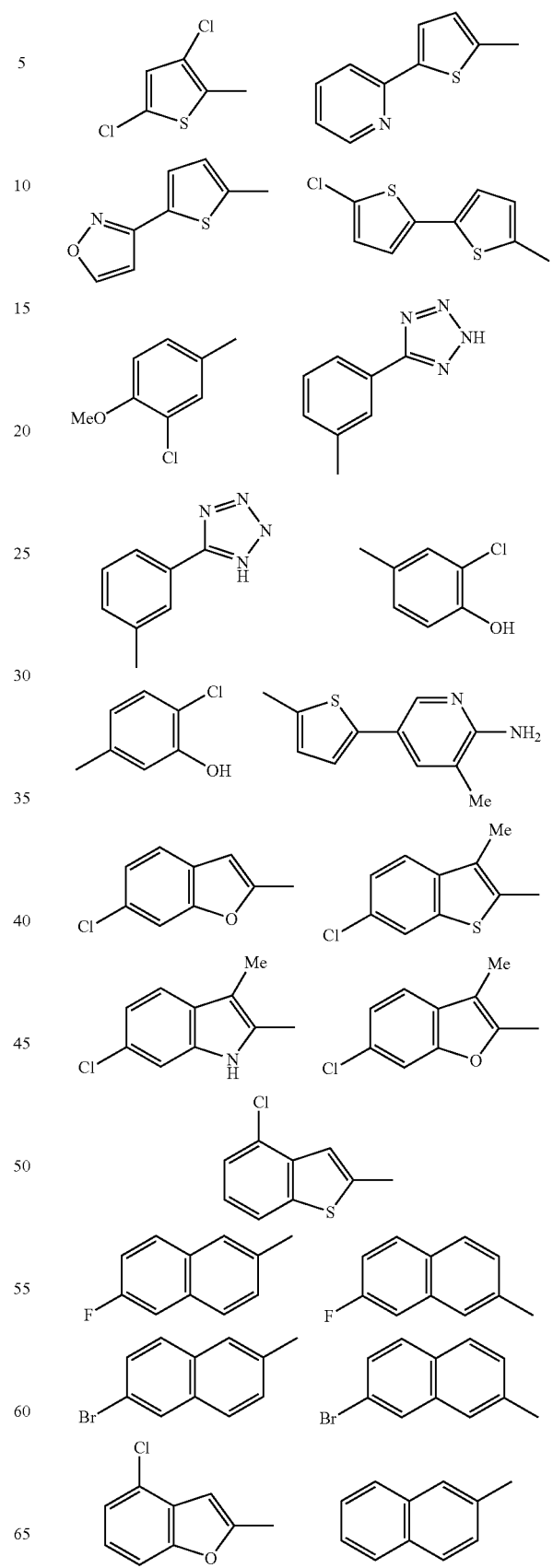

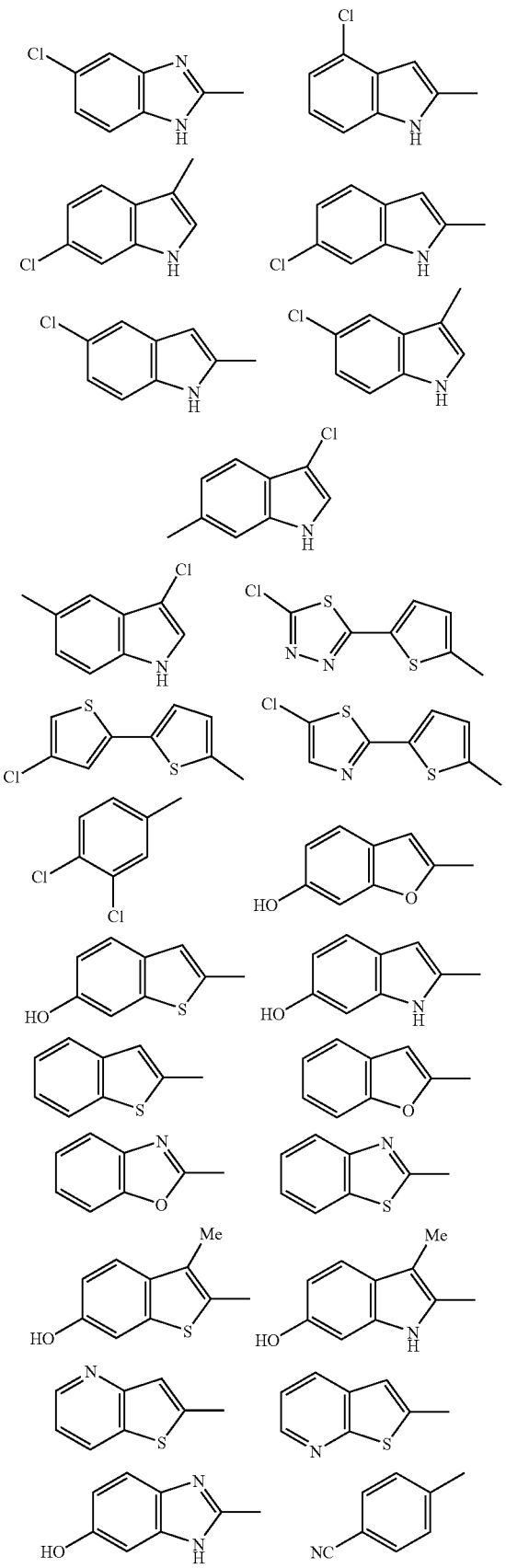

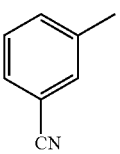

$G_1$ is selected from H, $C_{1-6}$ alkyl substituted with 0–1 $R^{1a}$, $CH_2C(O)OR^2$, $CH_2C(O)NR^2R^{2a}$, $CH_2C(O)NR^2CH_2CH_2OR^2$, $CH_2C(O)NR^2CH_2CH_2NR^2R^{2a}$, $CH_2C(O)NR^2CH_2C(O)NR^2R^{2a}$, $CH_2C(O)NR^2CH_2CH_2C(O)NR^2R^{2a}$, $CH_2C(O)NR^2CH_2C(O)OR^2$, and $CH_2C(O)NR^2CH_2CH_2C(O)OR^2$;

A is selected from one of the following carbocyclic and heterocyclic groups which are substituted with 0–2 $R^4$;

cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, $-(CH_2)_{0-1}-C_{5-6}$ carbocycle substituted with 0–2 $R^{4b}$, and $-(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, $-(CH_2)_{0-1}$-3–6 membered carbocycle substituted with 0–1 $R^5$, and a $-(CH_2)_{0-1}$-5–6 membered heterocycle consisting of: carbon atoms and 1–4 heteroatoms selected from the group consisting of N, O, and $S(O)_p$ and substituted with 0–1 $R^5$;

ring Q is a 5–7 membered lactam consisting of, in addition to the amide group shown, carbon atoms and 0–2 heteroatoms selected from $NR^{4c}$, O, S, S(O), and $S(O)_2$, wherein:

0–2 double bonds are present within the ring and the ring is substituted with 0–2 $R^{4a}$;

alternatively, ring Q is a 5–7 membered lactam to which another ring is fused, wherein:

the lactam consists of, in addition to the shown amide group, carbon atoms and 0–2 heteroatoms selected from $NR^{4c}$, O, S, S(O), and $S(O)_2$ and 0–1 double bonds are present within the ring;

the fusion ring is phenyl or a 5–6 membered heteroaromatic consisting of carbon atoms and 0–2 $NR^{4c}$, O, and S;

ring Q, which includes the lactam ring and the fusion ring, is substituted with 0–3 $R^{4a}$;

ring $Q^1$ is selected from $CY^1Y^2$, a $C_{3-6}$ monocyclic carbocycle, and 5–6 membered monocyclic heterocycle, wherein the carobocycle or heterocycle consists of carbon atoms and 0–2 heteroatoms selected from N, O, and S(O)p, the carbocycle or heterocycle further comprises 0–1 double bonds and 0–1 carbonyl groups, and the carbocycle or heterocycle is substituted with 0–2 $R^4$;

X is absent or is selected from $-(CR^2R^{2a})_{1-2}-$, $-C(O)-$, $-S(O)_2-$, $-S(O)_2NR^2-$, $-NR^2S(O)_2-$, $-NR^2C(O)-$, $-C(O)NR^2-$, $NR^2$, $-NR^2CR^2R^{2a}-$, $-CR^2R^{2a}NR^2-$, O, $-OCR^2R^{2a}-$, and $-CR^2R^{2a}O-$;

$Y^1$ and $Y^2$ are independently $C_{1-2}$ alkyl substituted with 0–1 $R^4$;

$R^{1a}$, at each occurrence, is selected from H, $-(CH_2)_r-R^{1b}$, $(-CH_2)_r-O-(CH_2)_r-R^{1b}$, $-(CH_2)_r-C(=NR^{1b})NR^3R^{1b}$, $NR^3(CR^3R^{3a})_rR^{1c}$, $O(CR^3R^{3a})_rR^{1c}$, $(CH_2)_rNR^3(CH_2)_rR^{1b}$, $(CH_2)_rC(O)NR^2(CH_2)_rR^{1b}$, $CO_2(CH_2)_rR^{1b}$, $O(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–6 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

$R^{1b}$ is selected from H, $CH_3$, $CH_2CH_3$, F, Cl, Br, —CN, CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2d}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–2 $R^{4b}$, a benzyl substituted with 0–2 $R^{4b}$, a 5–6 membered heterocycle-$CH_2$ group wherein said heterocycle consists of: carbon atoms and 1–4 heteroatoms selected from the group consisting of N, O, and $S(O)_p$ and substituted with 0–2 $R^{4b}$, and a 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, benzyl, phenyl substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and $-(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and $-(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or $C(O)-S(O)_p$ moiety;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from $-(CR^3R^{3g})_r$-5–6 membered carbocycle substituted with 0–3 $R^{4c}$, $-(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r-NR^{2d}C(O)R^{2e}$, $(CR^3R^{3g})_r-C(O)R^{2e}$, $(CR^3R^{3g})_r-OC(O)R^{2e}$, $(CR^3R^{3g})_r-C(O)NR^{2d}R^{2d}$, $(CR^3R^{3g})_r-C(O)OR^{2d}$, $(CR^3R^{3g})_r-NR^{2d}C(O)NR^{2d}R^{2d}$, $(CR^3R^{3g})_r-NR^{2d}C(O)OR^{2d}$, $(CR^3R^{3g})_r-SO_2NR^{2d}R^{2d}$, $(CR^3R^{3g})_r-NR^{2d}SO_2R^{2d}$, and $(CR^3R^{3g})_r-S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2-C(O)R^3$, $C(O)OR^{3c}$, $CH_2-C(O)OR^{3c}$, $NR^3C(O)R^{3a}$, $CH_2NR^3C(O)R^{3a}$, $C(O)NR^3R^{3a}$, $CH_2-C(O)NR^3R^{3a}$, $SO_2NR^3R^{3a}$, $CH_2SO_2NR^3R^{3a}$, $NR^3SO_2-C_{1-4}$ alkyl, $CH_2NR^3SO_2-C_{1-4}$ alkyl, $NR^3SO_2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{2-3}$ alkenyl, $C_{2-3}$ alkynyl, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C$ (O)R$^{2c}$, NR$^2$C(O)R$^{2b}$, (CR$^3$R$^{3a}$)NR$^2$C(O)R$^{2b}$, C(O)NR$^2$R$^{2a}$, (CR$^3$R$^{3a}$)C(O)NR$^2$R$^{2a}$, NR$^2$C(O)NR$^2$R$^{2a}$, (CR$^3$R$^{3a}$)NR$^2$C(O)NR$^2$R$^{2a}$, SO$_2$NR$^2$R$^{2a}$, (CR$^3$R$^{3a}$)SO$_2$NR$^2$R$^{2a}$, NR$^2$SO$_2$NR$^2$R$^{2a}$, (CR$^3$R$^{3a}$)NR$^2$SO$_2$NR$^2$R$^{2a}$, NR$^2$SO$_2$R$^{5a}$, (CR$^3$R$^{3a}$)NR$^2$SO$_2$R$^{5a}$, S(O)$_p$R$^{5a}$, (CR$^3$R$^{3a}$)S(O)$_p$R$^{5a}$, CF$_3$, CF$_2$CF$_3$, C$_{3-10}$ carbocycle substituted with 0–2 R$^{4b}$, (CR$^3$R$^{3a}$)C$_{3-10}$ carbocycle substituted with 0–2 R$^{4b}$, 5–10 membered heterocycle consisting of carbon atoms and from 1–4 heteroatoms selected from the group consisting of N, O, and S(O)$_p$ and substituted with 0–2 R$^{4b}$, and (CR$^3$R$^{3a}$)-5–10 membered heterocycle consisting of carbon atoms and from 1–4 heteroatoms selected from the group consisting of N, O, and S(O)$_p$ and substituted with 0–2 R$^{4b}$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, SO$_2$NR$^2$R$^{2a}$, and NR$^2$SO$_2$C$_{1-4}$ alkyl.

4. A compound according to claim 3, wherein:

G is selected from the group:

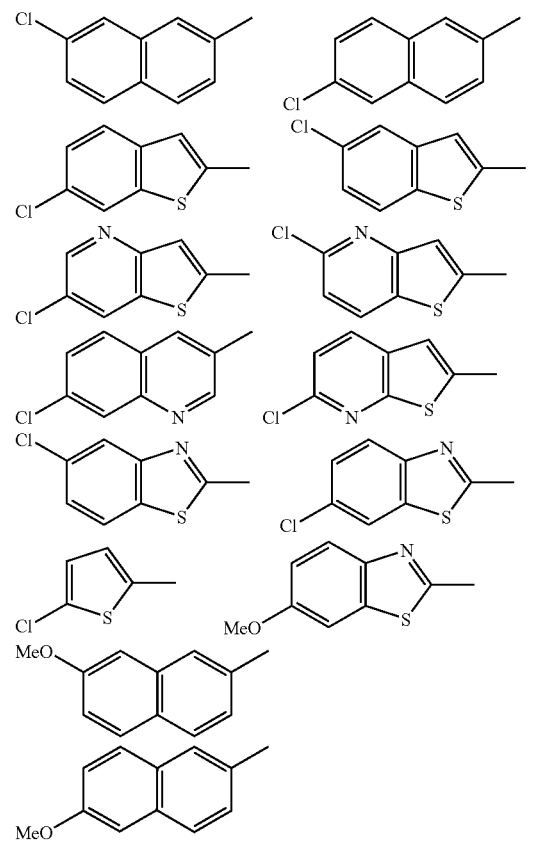

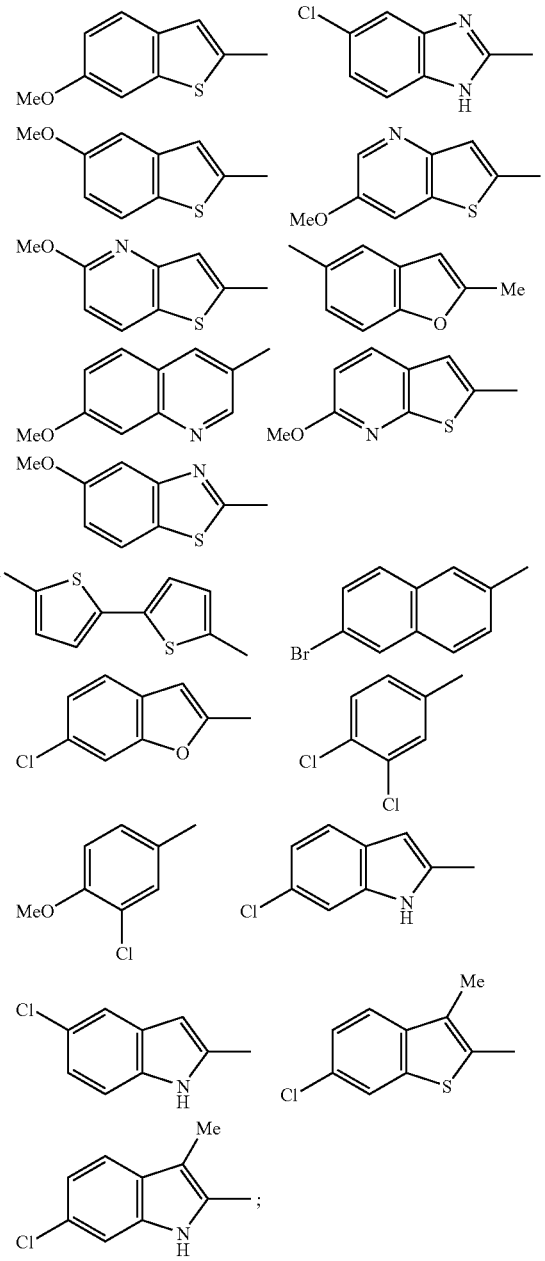

G$_1$ is selected from H, C$_{1-4}$ alkyl substituted with 0–1 R$^{1a}$, CH$_2$C(O)OR$^2$, CH$_2$C(O)NR$^2$R$^{2a}$, CH$_2$C(O)NHCH$_2$CH$_2$OR$^2$, and CH$_2$C(O)NHCH$_2$CH$_2$NR$^2$R$^{2a}$, CH$_2$C(O)OR$^2$, CH$_2$C(O)NR$^2$R$^{2a}$, CH$_2$C(O)N(CH$_3$)CH$_2$CH$_2$OR$^2$, CH$_2$C(O)N(CH$_3$)CH$_2$CH$_2$NR$^2$R$^{2a}$, CH$_2$C(O)NR$^2$CH$_2$C(O)NR$^2$R$^{2a}$, CH$_2$C(O)NR$^2$CH$_2$CH$_2$C(O)NR$^2$R$^{2a}$, CH$_2$C(O)NR$^2$CH$_2$C(O)OR$^2$, and CH$_2$C(O)NR$^2$CH$_2$CH$_2$C(O)OR$^2$;

A is selected from one of the following carbocyclic and heterocyclic groups which are substituted with 0–2 R$^4$;

cyclohexyl, phenyl, piperidinyl, piperazinyl, pyridyl, pyrimidyl, thienyl, pyrrolyl, pyrrolidinyl, oxazolyl, isoxazolyl, thiazolyl, isothiazolyl, pyrazolyl, and imidazolyl;

B is selected from $N(B^1)C(O)C(R^3R^{3g})NB^2B^3$,

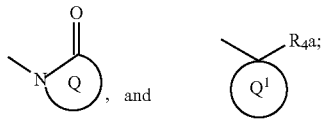, and provided that the central lactam ring and B are attached to different atoms on A;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

ring Q is a 6–7 membered lactam consisting of, in addition to the amide group shown, carbon atoms and 0–1 heteroatoms selected from $NR^{4c}$, O, S, S(O), and $S(O)_2$, wherein:
0–2 double bonds are present within the ring and the ring is substituted with 0–2 $R^{4a}$;

alternatively, ring Q is a 5–7 membered lactam to which another ring is fused, wherein:
the lactam consists of, in addition to the shown amide group, carbon atoms and 0–1 heteroatoms selected from $NR^{4c}$, O, S, S(O), and $S(O)_2$ and 0–1 double bonds are present within the ring;
the fusion ring is phenyl;
ring Q, which includes the lactam ring and the fusion ring, is substituted with 0–2$R^{4a}$;

ring $Q^1$ is selected from $C(CH_3)_2$, $C(CH_2CH_3)_2$, cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and, when Y is a ring, Y is substituted with 0–1 $R^4$;

$R^{1a}$ is selected from H, $R^{1b}$, $C(CH_3)_2R^{1b}$, $CH(CH_3)R^{1b}$, $CH_2R^{1b}$, $CH_2CH_2R^{1b}$, $CH_2OCH_2CH_2R^{1b}$, $OCH_2CH_2R^{1b}$, $(CH_2)_rNR^3CH_2CH_2R^{1b}$, $NR^3(CR^3R^{3a})_rR^{1c}$, $O(CR^3R^{3a})_rR^{1c}$, $(CH_2)_rC(O)NR^2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–2 ring double bonds;

$R^{1b}$ is selected from H, $CH_3$, $CH_2CH_3$, F, Cl, Br, —CN, —CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2d}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-6}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{2a}$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, and benzyl;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or $C(O)$—$S(O)_p$ moiety;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3a})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3a})_rN(→O)R^{2d}R^{2d}$, $(CR^3R^{3g})_rOR^{2d}$, $(CR^3R^{3g})_r$—$C(O)NR^{2d}R^{2d}$, $CR^3R^{3g})_r$—$NR^{2d}C(O)R^{2e}$, $(CR^3R^{3g})_r$—$C(O)R^{2e}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

5. A compound according to claim 4, wherein:
G is selected from:

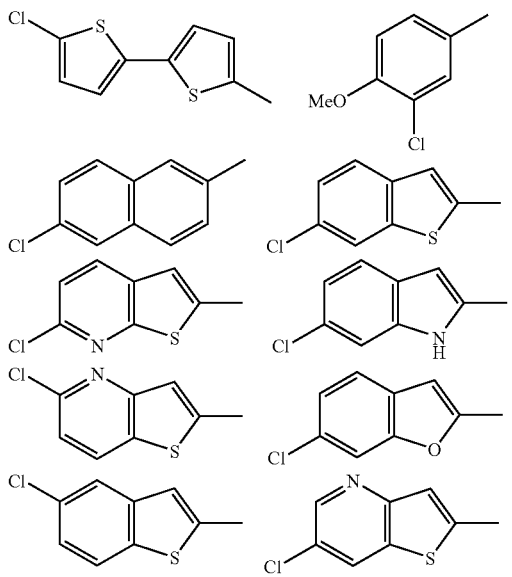

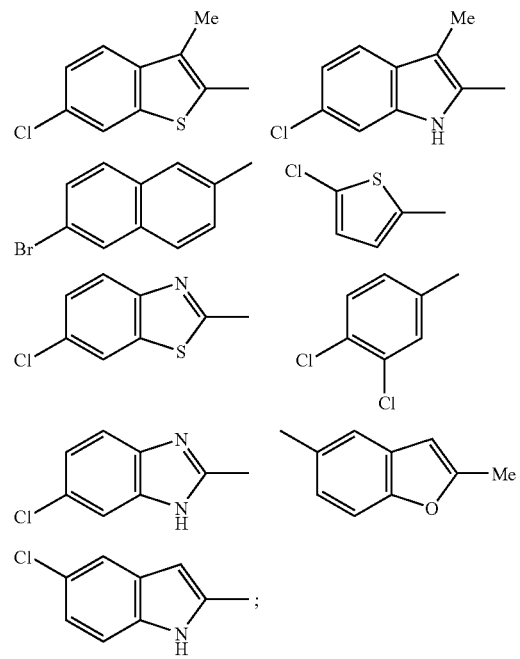

A is selected from one of the following carbocyclic and heterocyclic groups which are substituted with 0–2 $R^4$;
cyclohexyl, phenyl, pyridyl, and pyrimidyl;

B is selected from the group:

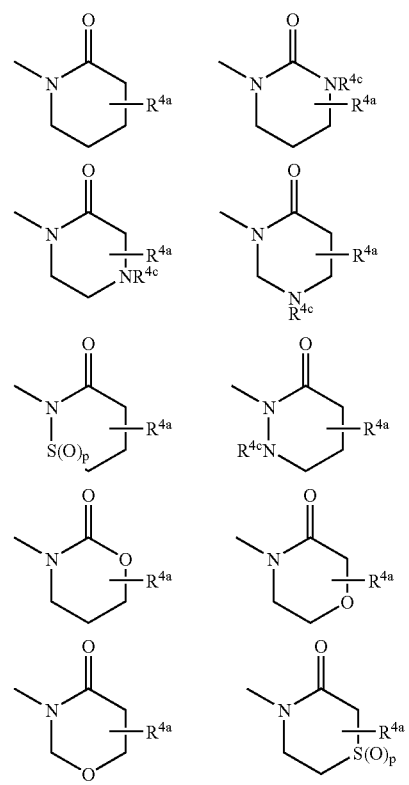

-continued

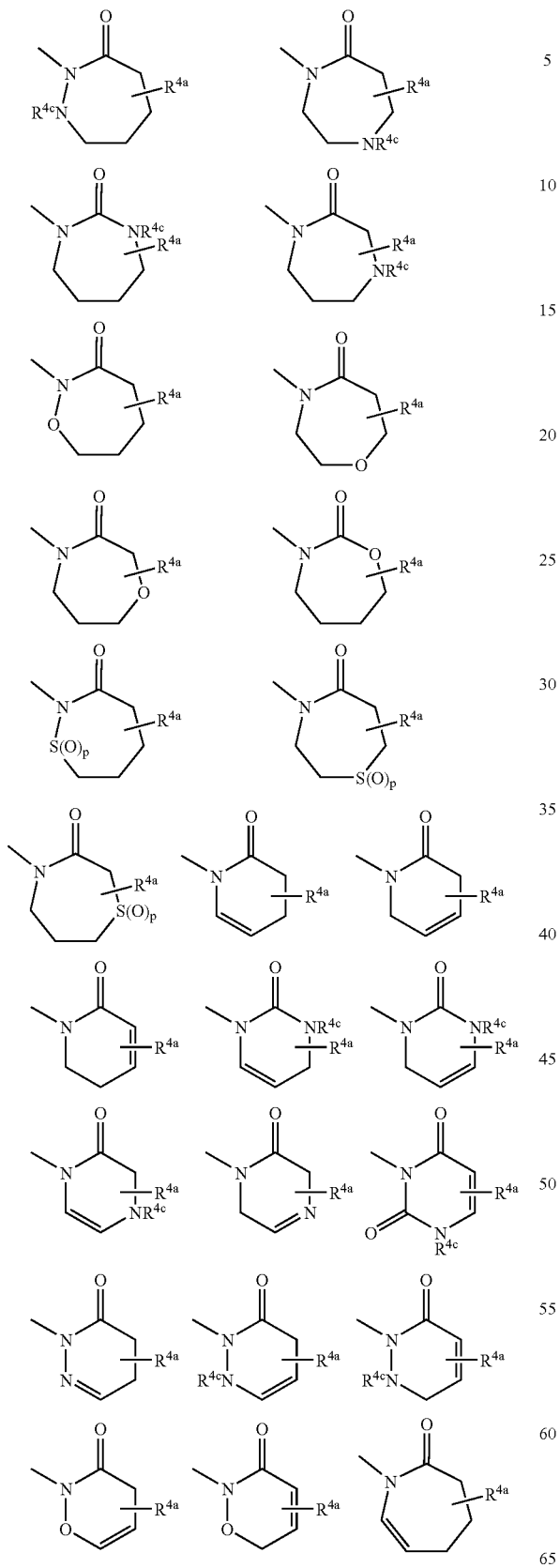

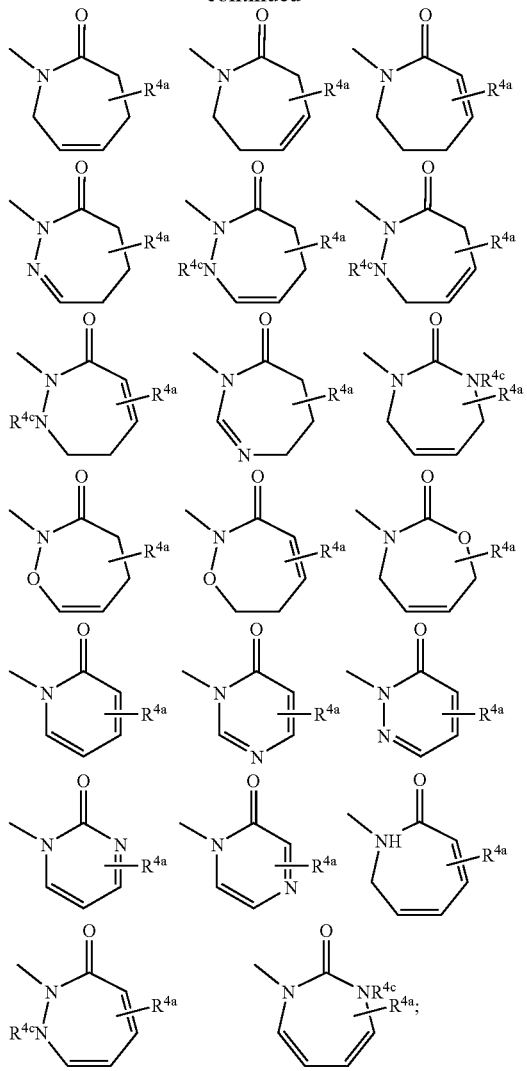

alternatively, B is selected from
N(B¹)C(O)C(R³R³ᵍ)NB²B³ and

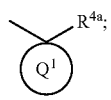

$B^1$ is selected from H, $CH_3$, $CH_2CH_3$, and $CH_2CH_2CH_3$;
$B^2$ is selected from H, $CH_3$, and $CH_2CH_3$;
$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, and $CH_2$-cyclopropyl;
ring $Q^1$ is selected from $C(CH_3)_2$, $C(CH_2CH_3)_2$, cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position) 4-piperdinonyl (attached to A and $R^{4a}$ at the 3-position), tetrahydrofuranyl, and tetrahydropyranyl (attached to A and $R^{4a}$ at the 4-position);

$R^{1a}$ is selected from H, $CH_3$, $CH_2CH_3$, $CH_2CH_2CH_3$, $CH_2(CH_3)_2$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $NHCOCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, $NHSO_2NHCH_3$, $NHSO_2N(CH_3)_2$, $NHCO_2R^{2a}$, $NHC(O)NHR^{2a}$, $CH_2OCH_2CH_2NR^2R^{2a}$, $C(O)NR^2R^{2a}$, $CH_2CH_2OR^2$, $CH_2C(O)NR^2CH_2CH_2OR^2$, $C(O)NHCH_2CH_2NR^2R^{2a}$, $CH_2C(O)NHCH_2CH_2NR^2R^{2a}$, $C(O)NCH_3CH_2CH_2NR^2R^{2a}$, $CH_2C(O)NCH_3CH_2CH_2NR^2R^{2a}$, $CH_2NHCH_2CH_2NR^2R^{2a}$, $CH_2N(CH_3)CH_2CH_2NR^2R^{2a}$, phenyl substituted with 0–2 $R^{4b}$, —$CH_2$-phenyl substituted with 0–2 $R^{4b}$, 5–10 membered aromatic heterocycle consisting of carbon atoms and from 1–4 heteroatoms selected from the group consisting of N, O, and $S(O)_p$ and substituted with 0–2 $R^{4b}$, and —$CH_2$-5–10 membered aromatic heterocycle consisting of carbon atoms and from 1–4 heteroatoms selected from the group consisting of N, O, and $S(O)_p$ and substituted with 0–2 $R^{4b}$, provided that $R^{1a}$ forms other than an N-halo, N—S, O—O, or N—CN bond;

$R^2$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–1 $R^{4b}$, benzyl substituted with 0–1 $R^{4b}$, 5 membered aromatic heterocycle-$CH_2$ group wherein the heterocycle consists of: carbon atoms and 1–4 heteroatoms selected from the group consisting of N, O, and $S(O)_p$ and substituted with 0–1 $R^{4b}$ and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$, $CH_2CH_2OH$, $CH_2CH_2CH_2OH$, $CH_2CH_2NMe_2$, and $CH_2CH_2CH_2NMe_2$, alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2c}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —$(CH_2)$-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or S(O)H; and, $R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_p$-phenyl, and $CF_3$; and, $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, CH=$CH_2$, CH≡CH, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

6. A compound according to claim 5, wherein the compound is selected from:

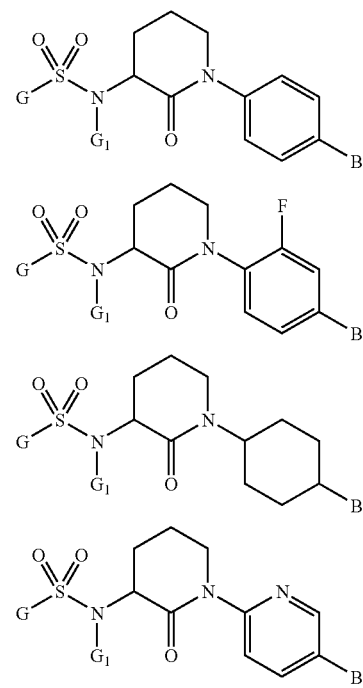

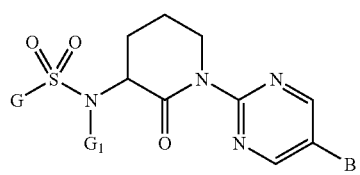
B is selected from:
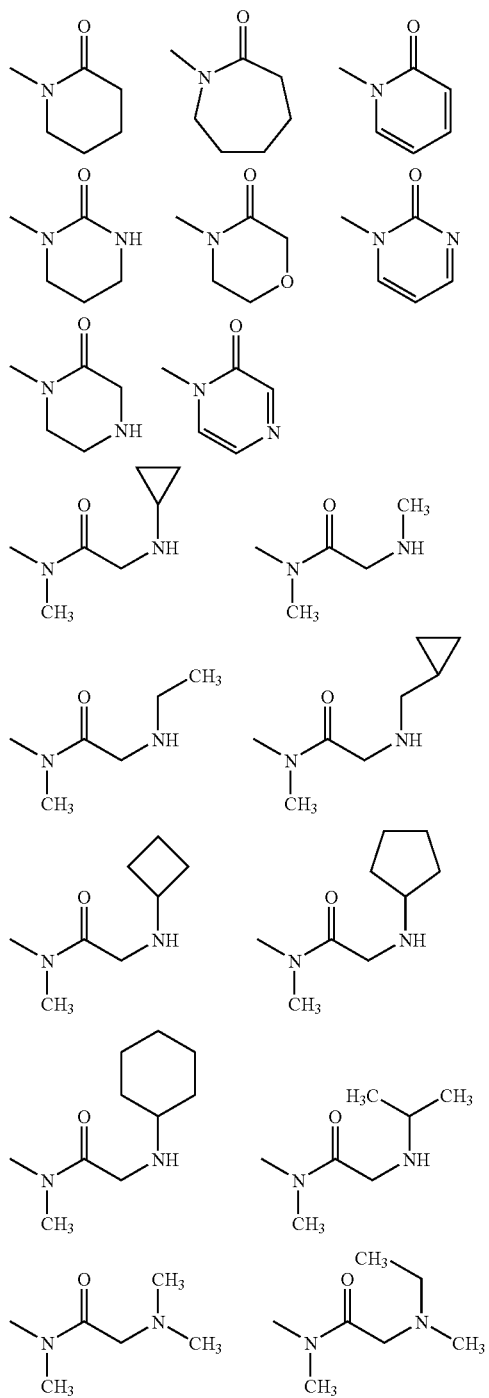
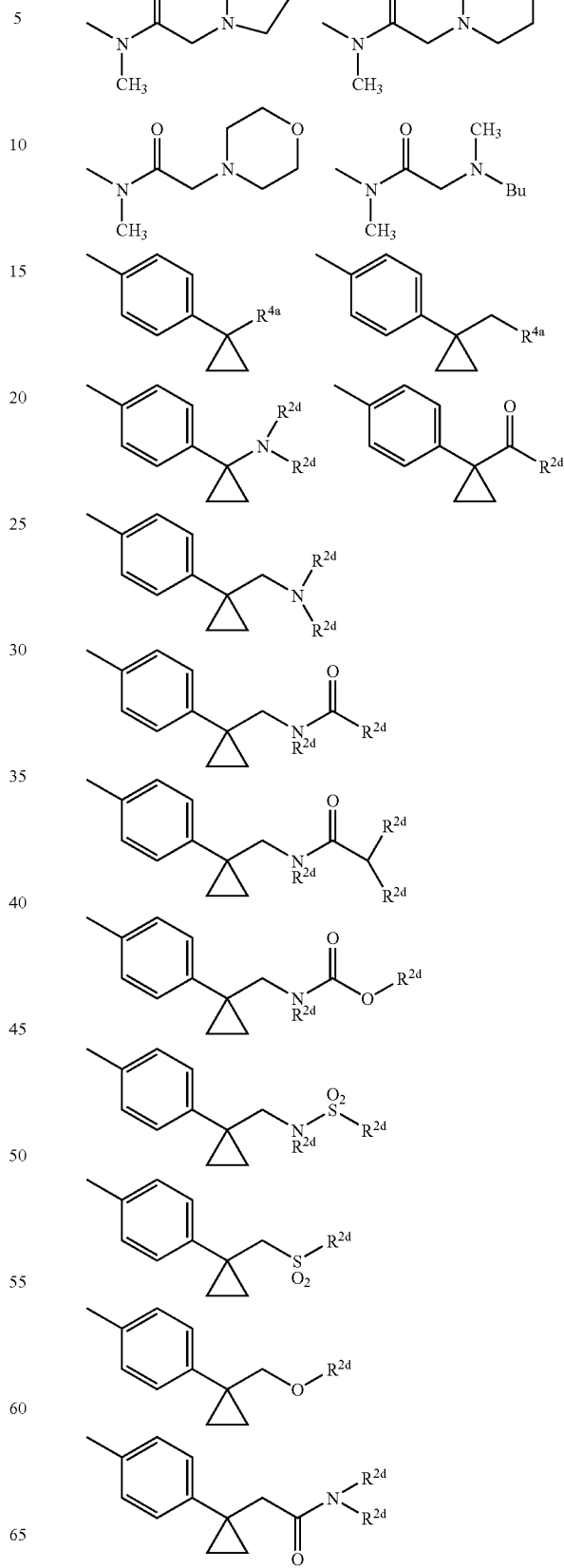

-continued
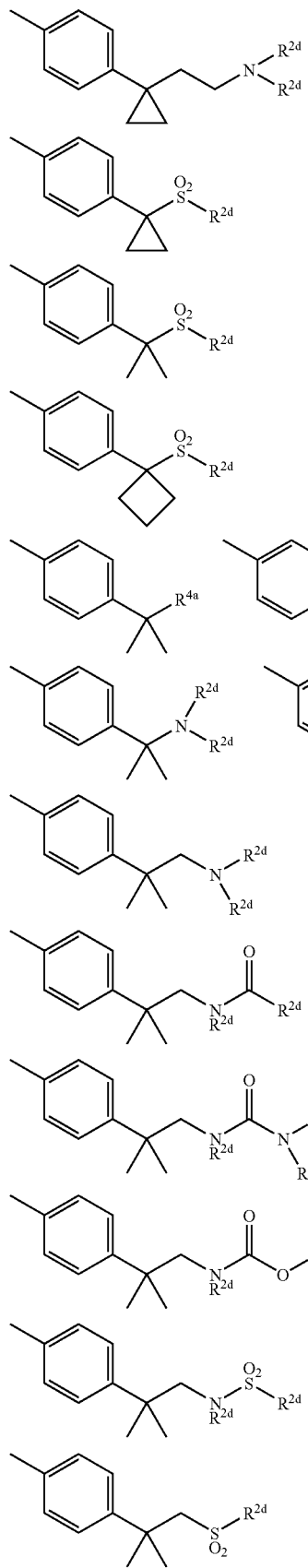
-continued
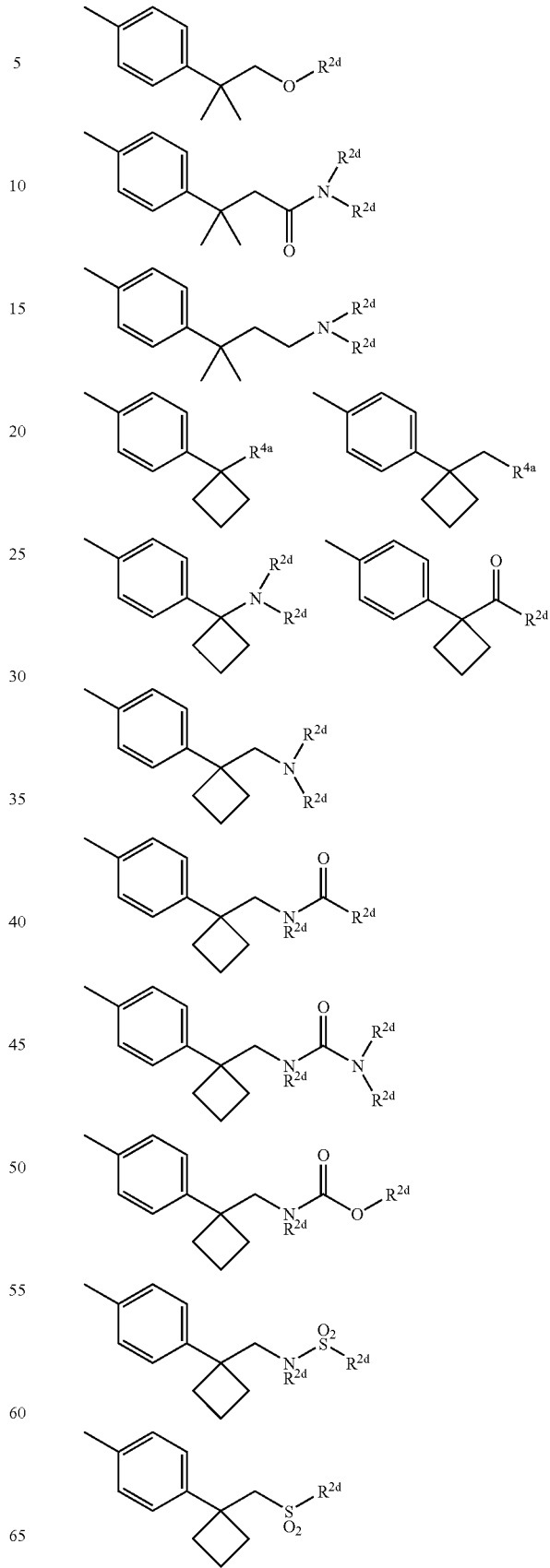

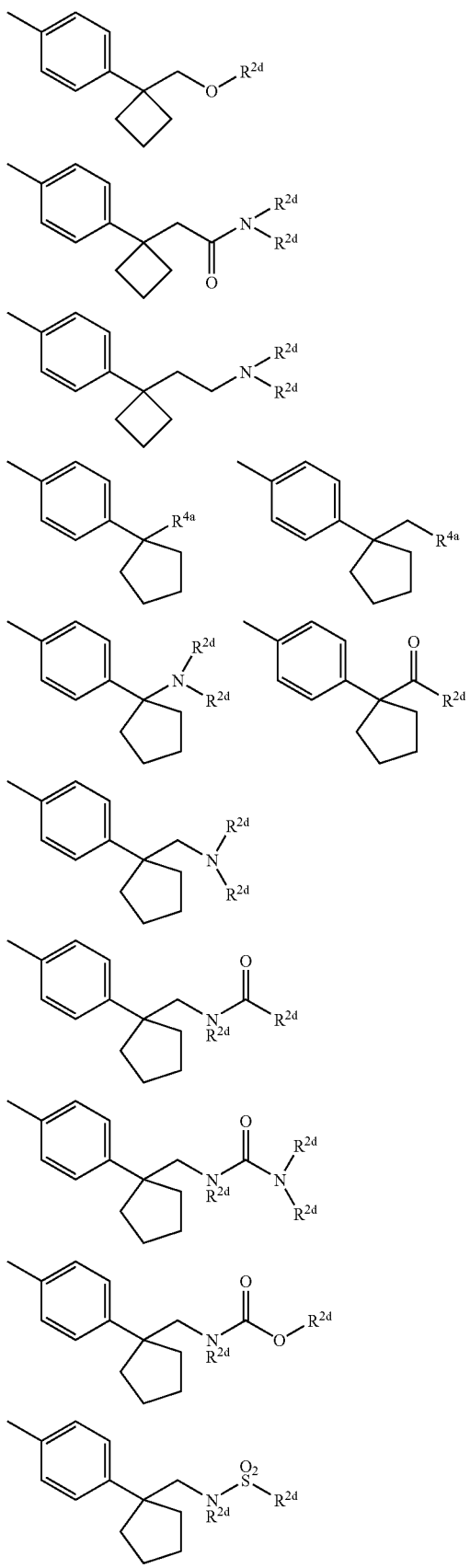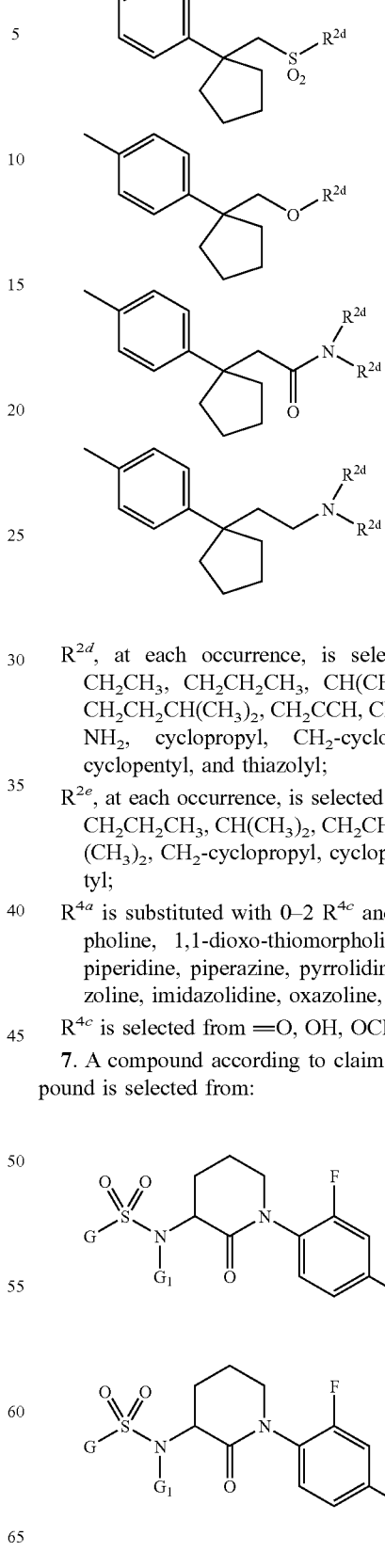

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2CCH$, $CH_2CH_2OH$, $CH_2C(O)NH_2$, cyclopropyl, $CH_2$-cyclopropyl, cyclobutyl, cyclopentyl, and thiazolyl;

$R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, irnidazole, imidazoline, imidazolidine, oxazoline, and thiazoline; and, $R^{4c}$ is selected from =O, OH, $OCH_3$, and $CH_3$.

7. A compound according to claim 6, wherein the compound is selected from:

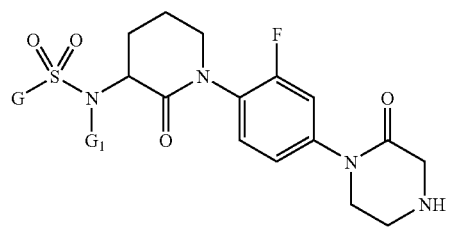
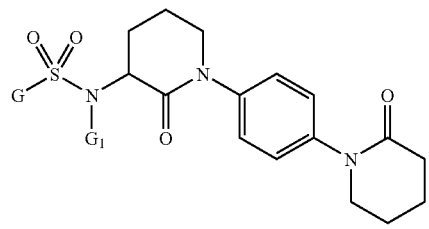
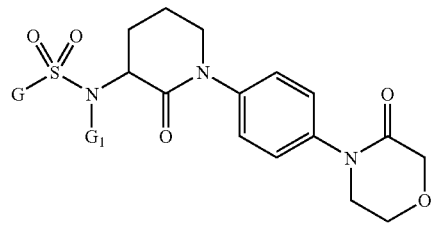
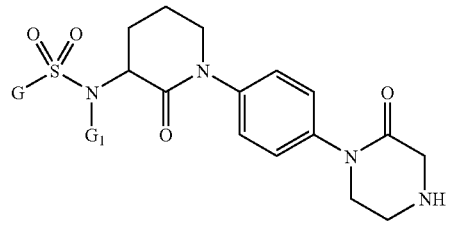
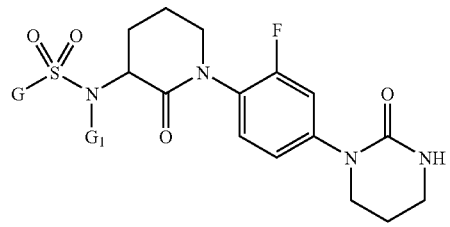
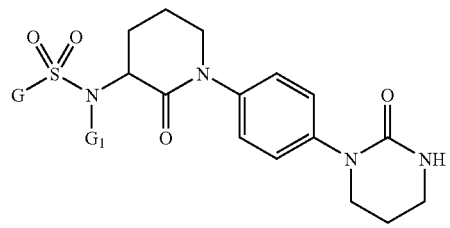
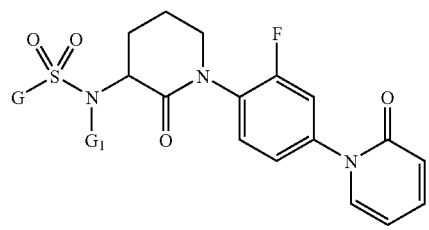
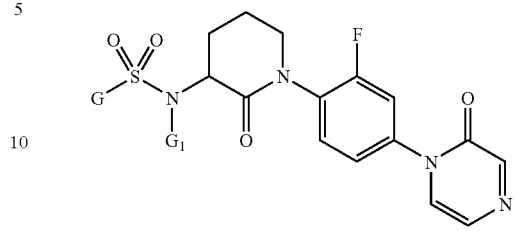
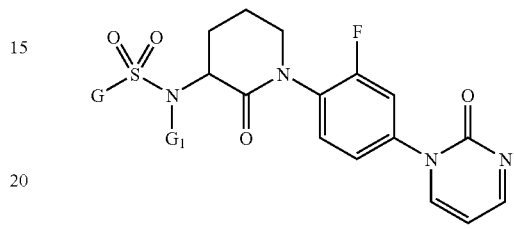
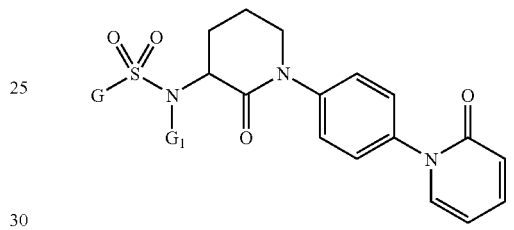
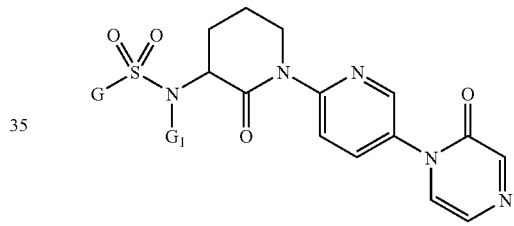
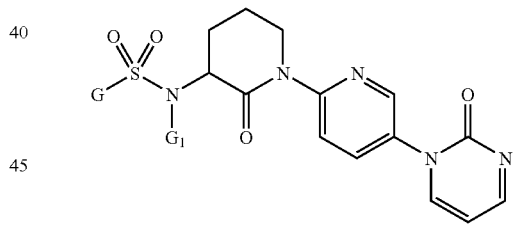
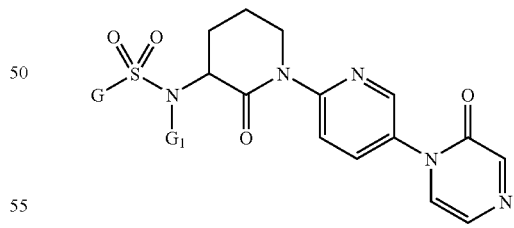
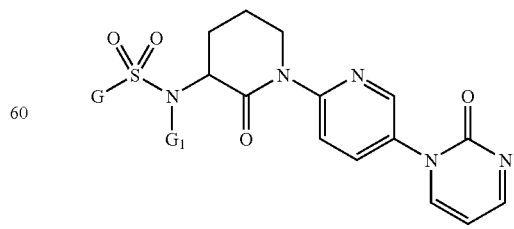

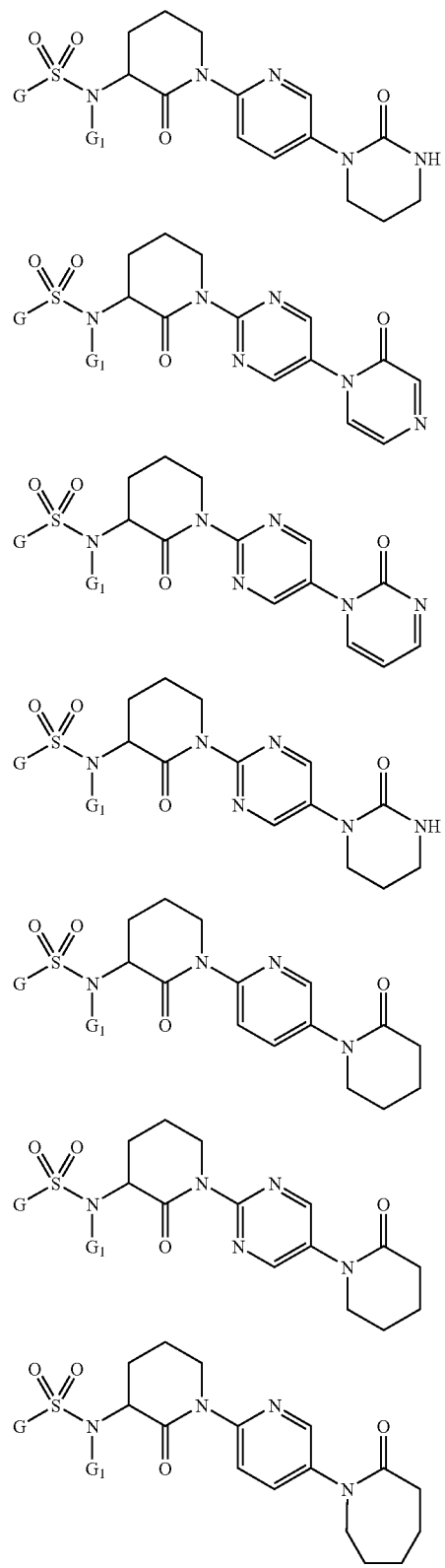
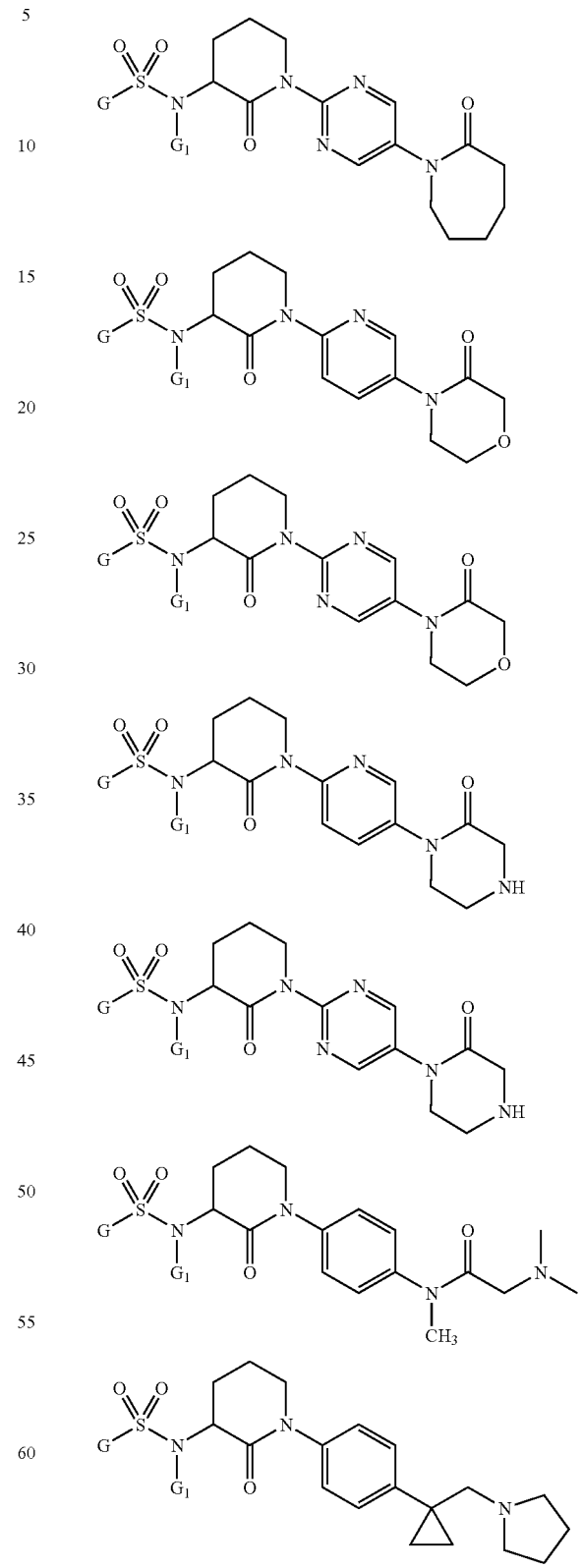

151 152
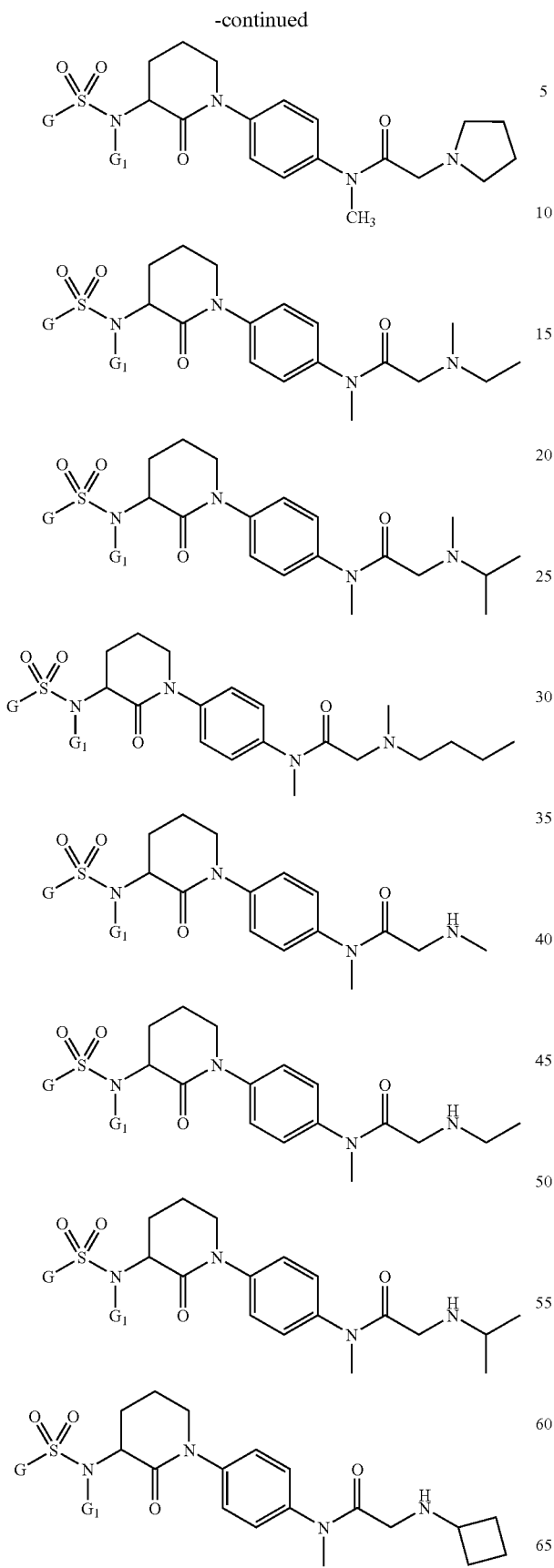
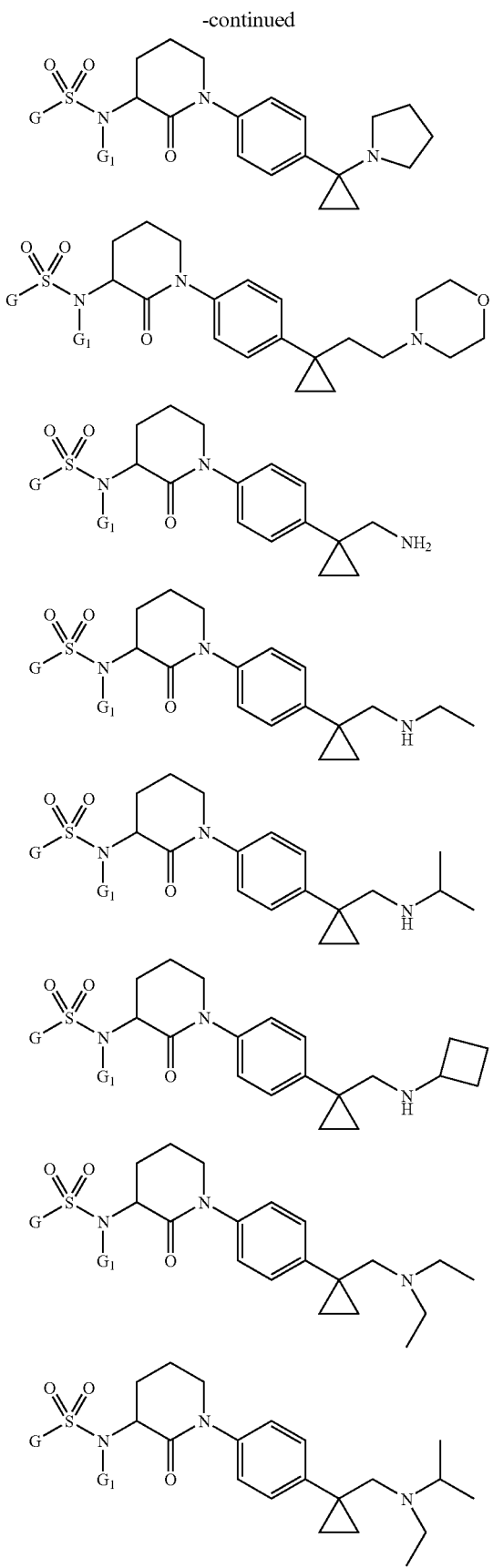

-continued

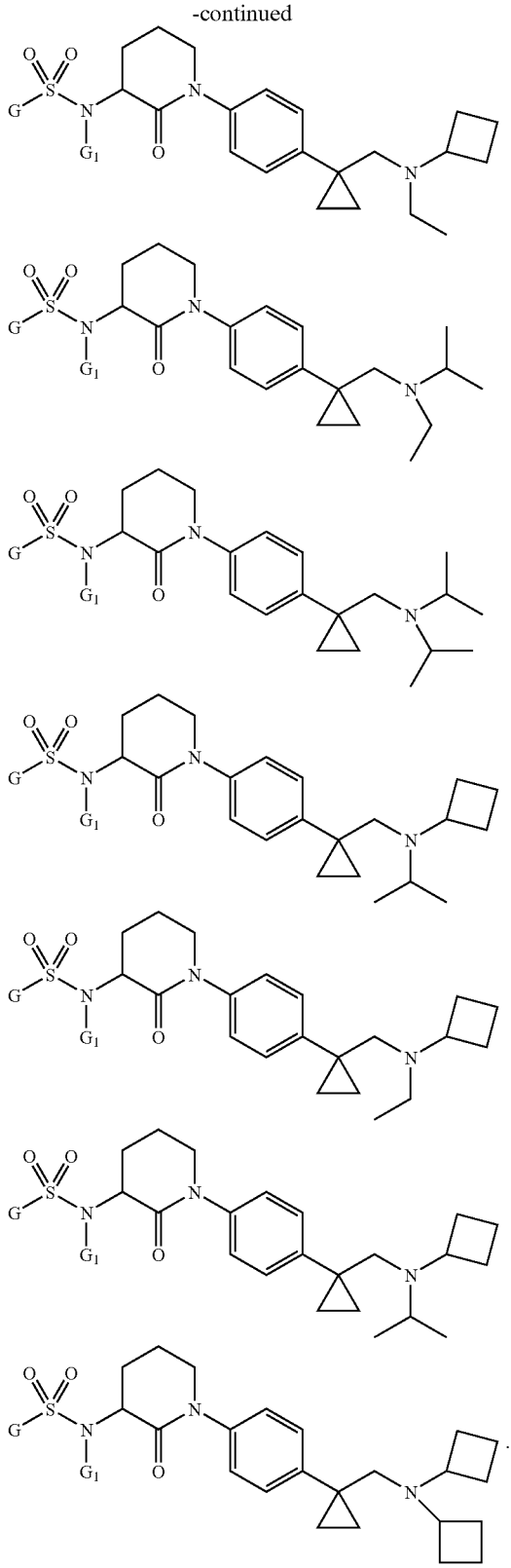

8. A pharmaceutical composition, comprising: a pharmaceutically acceptable carrier and a therapeutically effective amount of a compound of claim 1 or a pharmaceutically acceptable salt thereof.

9. A method for treating a thromboembolic disorder, comprising: administering to a patient in need thereof a therapeutically effective amount of a compound of claim 1 or a pharmaceutically acceptable salt form thereof.

10. A method according to claim 9, wherein the thromboembolic disorder is selected from the group consisting of arterial cardiovascular thromboembolic disorders, venous cardiovascular thromboembolic disorders, and thromboembolic disorders in the chambers of the heart.

11. A method according to claim 9, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

12. A method for treating a thromboembolic disorder, comprising: administering to a patient in need thereof a therapeutically effective amount of a first and second therapeutic agent, wherein the first therapeutic agent is compound of claim 1 or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

13. A method according to claim 12, wherein the second therapeutic agent is at least one agent selected from warfarin, unfractionated heparm, low molecular weight heparin, synthetic pentasaccharide, hirudin, argatrobanas, aspirin, ibuprofen, naproxen, sulindac, indomethacin, mefenamate, droxicam, diclofenac, sulfmpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

14. The method according to claim 12, wherein the second therapeutic agent is at least one anti-platelet agent.

15. The method according to claim 14, wherein the anti-platelet agent is aspirin and clopidogrel.

16. The method according to claim 14, wherein the anti-platelet agent is clopidogrel.

17. A compound is selected from the group:

6-chloronaphthalene-2-sulfonic acid {1-[2-fluoro-4-(2-oxo-piperidin-1-yl)-phenyl]-2-oxopiperidin-3-yl}-amide;

6-chloronaphthalene-2-sulfonic acid {1-[2-fluoro-4-(2-oxo-2H-pyridin-1-yl)phenyl]-2-oxopiperidin-3-yl}amide;

6-chlorothieno[2,3-b]pyridine-2-sulfonic acid {1-[2-fluoro-4-(2-oxo-2H-pyridin-1-yl)phenyl]-2-oxopiperidin-3-yl}amide;

2-((6-chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

(R)-2-((6-chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

(S)-2-((6-Chloronaphthalene-2-sulfonyl)-{1-[2-fluoro-4-(2-oxo-2H-pyridin-1-yl)phenyl]-2-oxo-piperidin-3-yl}amino)-N-(2-dimethylaminoethyl)-N-methylacetamide;

2-((6-chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-N-methylacetamide;

2-((6-chlorothieno[2,3-b]pyridine-2-sulfonyl)-{1-[2-fluoro-4-(2-oxo-2H-pyridin-1-yl)phenyl]-2-oxo-piperidin-3-yl}-amino)-N-(2-dimethylaminoethyl)-N-methylacetamide;

6-chloronaphthalene-2-sulfonic acid {1-[4-(2-oxo-2H-pyridin-1-yl)-phenyl]-2-oxo-piperidin-3-yl}amide;

6-chlorothieno[2,3-b]pyridine-2-sulfonic acid {1-[4-(2-oxo-2H-pyridin-1-yl)phenyl]-2-oxopiperidin-3-yl}amide;

2-((6-chloronaphthalene-2-sulfonyl)-{1-[2-fluoro-4-(2-oxo-piperidin-1-yl)-phenyl]-2-oxo-piperidin-3-yl}amino)-N-(2-dimethylaminoethyl)-N-methylacetamide;

2-{(6-chloronaphthalene-2-sulfonyl)-{1-[2-fluoro-4-(2-oxo-piperidin-1-yl)-phenyl]-2-oxopiperidin-3-yl]-amino}-N-methyl-N-(1-methylpiperidin-4-yl)-acetamide;

6-chloro-naphthalene-2-sulfonic acid {1-[2-fluoro-4-(2-oxo-piperidin-1-yl)-phenyl]-2-oxo-piperidin-3-yl}-[2-(4-methyl-piperazin-1-yl)-2-oxo-ethyl]-amide 6-chloronaphthalene-2-sulfonic acid {1-[2-fluoro-4-(2-oxo-piperidin-1-yl)-phenyl]-2-oxopiperidin-3-yl}-(2-morpholin-4-yl-2-oxoethyl)amide;

2-{(6-chlorothieno[2,3-b]pyridine-2-sulfonyl)-{1-[2-fluoro-4-(2-oxo-piperidin-1-yl)-phenyl]-2-oxopiperidin-3-yl]-amino}-N-methyl-N-(1-methylpiperidin-4-yl)-acetamide;

6-chlorothieno[2,3-b]pyridine-2-sulfonic acid {1-[2-fluoro-4-(2-oxo-piperidin-1-yl)-phenyl]-2-oxo-piperidin-3-yl}-[2-(4-methyl-piperazin-1-yl)-2-oxo-ethyl]-amide;

6-chlorothieno[2,3-b]pyridine-2-sulfonic acid {1-[2-fluoro-4-(2-oxo-piperidin-1-yl)-phenyl]-2-oxopiperidin-3-yl}-(2-morpholin-4-yl-2-oxoethyl)amide; 2-((6-Chloro-thieno[2,3-b]pyridine-2-sulfonyl)-{1-[2-fluoro-4-(2-oxo-2H-pyridin-1-yl)-phenyl]-2-oxo-piperidin-3-yl}-amino)-N,N-dimethylacetamide;

N-{4-[3-(6-chloro-naphthalene-2-sulfonylamino)-2-oxo-piperidin-1-yl]-phenyl}-2-dimethylamino-N-methyl-acetamide;

N-{4-[3-(6-chloro-naphthalene-2-sulfonylamino)-2-oxo-piperidin-1-yl]-phenyl}-N-methyl-2-pyrrolidin-1-yl-acetamide;

N-{4-[3-(6-chloro-naphthalene-2-sulfonylamino)-2-oxo-piperidin-1-yl]-phenyl}-2-dimethylamino-N-methylacetamide;

N-{4-[3-(6-chloro-thieno [2,3-b]pyridine-2-sulfonylamino)-2-oxo-piperidin-1-yl]-phenyl}-2-dimethylamino-N-methyl-acetamide;

6-chloro-naphthalene-2-sulfonic acid methyl-{2-oxo-1-[4-(2-oxo-2H-pyridin-1-yl)-phenyl]-piperidin-3-yl}-amide;

6-chloro-thieno[2,3-b]pyridine-2-sulfonic acid methyl-{2-oxo-1-[4-(2-oxo-2H-pyridin-1-yl)-phenyl]-piperidin-3-yl}-amide;

6-chloro-naphthalene-2-sulfonic acid ethyl-{2-oxo-1-[4-(2-oxo-2H-pyridin-1-yl)-phenyl]-piperidin-3-yl}-amide;

6-chloro-thieno[2,3-b]pyridine-2-sulfonic acid ethyl-{2-oxo-1-[4-(2-oxo-2H-pyridin-1-yl)-phenyl]-piperidin-3-yl}-amide;

2-((6-chloro-thieno[2,3-b]pyridine-2-sulfonyl)-{2-oxo-1-[4-(2-oxo-2H-pyridin-1-yl)-phenyl]-piperidin-3-yl}-amino)-acetamide;

6-chloro-naphthalene-2-sulfonic acid cyanomethyl-{2-oxo-1-[4-(2-oxo-2H-pyridin-1-yl)-phenyl]-piperidin-3-yl}-amide;

6-chloro-naphthalene-2-sulfonic acid {2-oxo-1-[4-(2-oxo-2H-pyridin-1-yl)-phenyl]-piperidin-3-yl}-thiazol-4-ylmethyl-amide;

6-chloro-naphthalene-2-sulfonic acid {2-oxo-1-[4-(2-oxo-2H-pyridin-1-yl)-phenyl]-piperidin-3-yl}-pyridin-3-ylmethyl-amide;

6-chloro-naphthalene-2-sulfonic acid {2-oxo-1-[4-(2-oxo-2H-pyridin-1-yl)-phenyl]-piperidin-3-yl}-pyridin-2-ylmethyl-amide;

6-chloro-naphthalene-2-sulfonic acid {2-oxo-1-[4-(2-oxo-2H-pyridin-1-yl)-phenyl]-piperidin-3-yl}-pyridin-4-ylmethyl-amide;

2-((6-chloro-naphthalene-2-sulfonyl)-{2-oxo-1-[4-(2-oxo-2H-pyridin-1-yl)-phenyl]-piperidin-3-yl}-amino)-N-methyl-acetamide;

2-((6-chloro-naphthalene-2-sulfonyl)-{2-oxo-1-[4-(2-oxo-2H-pyridin-1-yl)-phenyl]-piperidin-3-yl}-amino)-acetamide;

6-chloro-naphthalene-2-sulfonic acid (2-methyl-thiazol-4-ylmethyl)-{2-oxo-1-[4-(2-oxo-2H-pyridin-1-yl)-phenyl]-piperidin-3-yl}-amide;

4-methoxy-N-{2-oxo-1-[4-(2-oxo-2H-pyridin-1-yl)-phenyl]-piperidin-3-yl}-benzenesulfonamide;

5-chloro-thiophene-2-sulfonic acid {2-oxo-1-[4-(2-oxo-2H-pyridin-1-yl)-phenyl]-piperidin-3-yl}-amide;

3-chloro-N-{2-oxo-1-[4-(2-oxo-2H-pyridin-1-yl)-phenyl]-piperidin-3-yl}-benzenesulfonamide;

((4-methoxy-benzenesulfonyl)-{2-oxo-1-[4-(2-oxo-2H-pyridin-1-yl)-phenyl]-piperidin-3-yl}-amino)-acetic acid methyl ester;

((5-chloro-thiophene-2-sulfonyl)-{2-oxo-1-[4-(2-oxo-2H-pyridin-1-yl)-phenyl]-piperidin-3-yl}-amino)-acetic acid methyl ester;

2-((4-methoxy-benzenesulfonyl)-{2-oxo-1-[4-(2-oxo-2H-pyridin-1-yl)-phenyl]-piperidin-3-yl}-amino)-acetamide;

((6-chloro-naphthalene-2-sulfonyl)-{2-oxo-1-[4-(2-oxo-2H-pyridin-1-yl)-phenyl]-piperidin-3-yl}-amino)-acetic acid tert-butyl ester;

2-((5-chloro-thiophene-2-sulfonyl)-{2-oxo-1-[4-(2-oxo-2H-pyridin-1-yl)-phenyl]-piperidin-3-yl}-amino)-acetamide;

((6-chloro-naphthalene-2-sulfonyl)-{2-oxo-1-[4-(2-oxo-2H-pyridin-1-yl)-phenyl]-piperidin-3-yl}-amino)-acetic acid;

5-chloro-thieno[3,2-b]pyridine-2-sulfonic acid {2-oxo-1-[4-(2-oxo-2H-pyridin-1-yl)-phenyl]-piperidin-3-yl}-amide;

5'-chloro-[2,2']bithiophenyl-5-sulfonic acid {2-oxo-1-[4-(2-oxo-2H-pyridin-1-yl)-phenyl]-piperidin-3-yl}-amide;

2-((6-chloro-naphthalene-2-sulfonyl)-{2-oxo-1-[4-(2-oxo-2H-pyridin-1-yl)-phenyl]-piperidin-3-yl}-amino)-N-(2-hydroxy-ethyl)-acetamide;

N-carbamoylmethyl-2-((6-chloro-naphthalene-2-sulfonyl)-{2-oxo-1-[4-(2-oxo-2H-pyridin-1-yl)-phenyl]-piperidin-3-yl}-amino)-acetamide;

6-chloro-naphthalene-2-sulfonic acid {2-oxo-1-[4-(1-pyrrolidin-1-ylmethyl-cyclopropyl)-phenyl]-piperidin-3-yl}-amide;
6-chloro-thieno[2,3-b]pyridine-2-sulfonic acid {2-oxo-1-[4-(1-pyrrolidin-1-ylmethyl-cyclopropyl)-phenyl]-piperidin-3-yl}-amide;
((5'-chloro-[2,2']bithiophenyl-5-sulfonyl)-{2-oxo-1-[4-(2-oxo-2H-pyridin-1-yl)-phenyl]-piperidin-3-yl}-amino)-acetic acid methyl ester;
((5-chloro-thieno[3,2-b]pyridine-2-sulfonyl)-{2-oxo-1-[4-(2-oxo-2H-pyridin-1-yl)-phenyl]-piperidin-3-yl}-amino)-acetic acid methyl ester;
2-((6-chloro-naphthalene-2-sulfonyl)-{2-oxo-1-[4-(2-oxo-2H-pyridin-1-yl)-phenyl]-piperidin-3-yl}-amino)-acetic acid methyl ester;
2-((6-chlorothieno[2,3-b]pyridine-2-sulfonyl)-{2-oxo-1-[4-(2-oxo-2H-pyridin-1-yl)-phenyl]-piperidin-3-yl}-amino)-acetic acid methyl ester;
2-{(6-chloronaphthalene-2-sulfonyl)-[1-(3-fluoro-2'-methanesulfonylbiphenyl-4-yl)-2-oxopiperidin-3-yl]-amino}-N-methyl-N-(1-methylpiperidin-4-yl)-acetamide;
6-chloro-naphthalene-2-sulfonic acid [1-(3-fluoro-2'-methanesulfonyl-biphenyl-4-yl)-2-oxo-piperidin-3-yl]-[2-(4-methyl-piperazin-1-yl)-2-oxo-ethyl]-amide;
6-chloronaphthalene-2-sulfonic acid [1-(3-fluoro-2'-methanesulfonylbiphenyl-4-yl)-2-oxopiperidin-3-yl]-(2-morpholin-4-yl-2-oxoethyl)amide;
2-{(6-chloronaphthalene-2-sulfonyl)-[1-(3-fluoro-2'-methanesulfonylbiphenyl-4-yl)-2-oxopiperidin-3-yl]-amino}-N-(2-hydroxyethyl)-N-methylacetamide;
6-chloro-naphthalene-2-sulfonic acid [1-(3-fluoro-2'-methanesulfonylbiphenyl-4-yl)-2-oxopiperidin-3-yl]-(3-hydroxy-propyl)amide;
6-chloronaphthalene-2-sulfonic acid {1-[4-(2-dimethylaminomethylimidazol-1-yl)-2-fluorophenyl]-2-oxopiperidin-3-yl}amide;
6-chlorothieno[2,3-b]pyridine-2-sulfonic acid {1-[4-(2-dimethylaminomethylimidazol-1-yl)-2-fluorophenyl]-2-oxopiperidin-3-yl}amide;
5-chlorothieno[3,2-b]pyridine-2-sulfonic acid {1-[4-(2-dimethylaminomethylimidazol-1-yl)-2-fluorophenyl]-2-oxopiperidin-3-yl}amide;
5-chlorobenzothienyl-2-sulfonic acid {1-[4-(2-dimethylaminomethylimidazol-1-yl)-2-fluorophenyl]-2-oxopiperidin-3-yl}amide;
6-chlorothieno[2,3-b]pyridine-2-sulfonic acid {1-[4-(2-methylaminomethylimidazol-1-yl)-2-fluoro-phenyl]-2-oxo-piperidin-3-yl}amide; and
((6-chlorothieno[2,3-b]pyridine-2-sulfonyl)-{1-[2-fluoro-4-(2-methylaminomethylimidazol-1-yl)phenyl]-2-oxo-piperidin-3-yl}amino)acetic acid methyl ester; or a pharmaceutically acceptable salt form thereof.

18. A pharmaceutical composition, comprising: a pharmaceutically acceptable carrier and a therapeutically effective amount of a compound of claim 2 or a pharmaceutically acceptable salt thereof.

19. A pharmaceutical composition, comprising: a pharmaceutically acceptable carrier and a therapeutically effective amount of a compound of claim 3 or a pharmaceutically acceptable salt thereof.

20. A pharmaceutical composition, comprising: a pharmaceutically acceptable carrier and a therapeutically effective amount of a compound of claim 4 or a pharmaceutically acceptable salt thereof.

21. A pharmaceutical composition, comprising: a pharmaceutically acceptable carrier and a therapeutically effective amount of a compound of claim 5 or a pharmaceutically acceptable salt thereof.

22. A pharmaceutical composition, comprising: a pharmaceutically acceptable carrier and a therapeutically effective amount of a compound of claim 6 or a pharmaceutically acceptable salt thereof.

23. A pharmaceutical composition, comprising: a pharmaceutically acceptable carrier and a therapeutically effective amount of a compound of claim 7 or a pharmaceutically acceptable salt thereof.

24. A pharmaceutical composition, comprising: a pharmaceutically acceptable carrier and a therapeutically effective amount of a compound of claim 17 or a pharmaceutically acceptable salt thereof.

* * * * *